US008753865B2

(12) United States Patent
Hendrickson et al.

(10) Patent No.: US 8,753,865 B2
(45) Date of Patent: Jun. 17, 2014

(54) STEADY STATE ANAEROBIC DENITRIFYING CONSORTIUM FOR APPLICATION IN IN-SITU BIOREMEDIATION OF HYDROCARBON-CONTAMINATED SITES AND ENHANCED OIL RECOVERY

(75) Inventors: Edwin R. Hendrickson, Hockessin, DE (US); Abigail K. Luckring, West Chester, PA (US); Sharon Jo Keeler, Bear, DE (US); Michael P. Perry, Landenberg, PA (US); Eric R. Choban, Williamstown, NJ (US)

(73) Assignee: E I du Pont de Nemours and Company, Wilmington, DE (US)

( * ) Notice: Subject to any disclaimer, the term of this patent is extended or adjusted under 35 U.S.C. 154(b) by 319 days.

(21) Appl. No.: 12/704,609

(22) Filed: Feb. 12, 2010

(65) Prior Publication Data

US 2010/0216217 A1 Aug. 26, 2010

Related U.S. Application Data

(60) Provisional application No. 61/154,542, filed on Feb. 23, 2009.

(51) Int. Cl.
*C12N 1/20* (2006.01)
(52) U.S. Cl.
USPC ...................................................... 435/252.4
(58) Field of Classification Search
None
See application file for complete search history.

(56) References Cited

U.S. PATENT DOCUMENTS

| | | | |
|---|---|---|---|
| 5,044,435 | A | 9/1991 | Sperl et al. |
| 6,543,535 | B2 | 4/2003 | Converse et al. |
| 6,852,234 | B2 | 2/2005 | Breitenbeck |
| 7,172,688 | B2 | 2/2007 | Petersen |
| 7,201,804 | B2 | 4/2007 | Tunnicliffe et al. |
| 7,442,313 | B2 | 10/2008 | Kerfoot |
| 7,449,429 | B2 | 11/2008 | Goldman |
| 7,465,395 | B2 | 12/2008 | Carbonell et al. |
| 7,473,672 | B2 | 1/2009 | Kotlar et al. |
| 7,708,065 | B2 | 5/2010 | Hendrickson et al. |
| 2007/0092930 | A1 | 4/2007 | Lal et al. |
| 2009/0082227 | A1 | 3/2009 | Hnatow et al. |

FOREIGN PATENT DOCUMENTS

WO 2010037000 A1 4/2010

OTHER PUBLICATIONS

Liu et al. (FEMS Microbiol. Ecol., 55:274-286, 2006).*
Roling, Wilfred et al., Bacterial Community Dynamics and Hydrocarbon Degradation during a Field-Scale Evaluation of Bioremediation on a Mudflat Beach Contaminated with Buried Oil, Applied and Environmental Microbiology, May 2004, pp. 2603-2613, vol. 70, No. 5.
Vazquez, S. et al., Bacterial Community Dynamics during Bioremediation of Diesel Oil-Contaminated Antarctic Soil, Microbial Ecology, 2009, pp. 598-610, vol. 57, No. 4.
Watanabe, Kazuya, Microorganisms relevant to bioremediation, Current Opinion in Biotechnology, Jun. 2001, pp. 237-241, vol. 12, No. 3.
Almeida, P. F. et al., Selection and Application of Microorganisms to Improve Oil Recovery, Engineering in Life Sciences, 2004, pp. 319-325, vol. 4, No. 4.
Beristain-Cardoso, Ricardo et al., Phenol and sulfide oxidation in a denitrifying biofilm reactor and its microbial community analysis, Process Biochemistry, 2009, pp. 23-28, vol. 44.
Breinig, Sabine et al., Genes Involved in Anaerobic Metabolism of Phenol in the Bacterium *Thauera aromatica*, Journal of Bacteriology, Oct. 2000, pp. 5849-5863, vol. 182, No. 20.
Chen, Chuan et al., Functional consortium for denitrifying sulfide removal process, Applied Microbiology Biotechnology, 2010, pp. 353-358, vol. 86.
Farhadian, Mehrdad et al., In situ bioremediation of monoaromatic pollutants in groundwater: A review, Bioresource Technology, 2008, pp. 5296-5308, vol. 99.
Foght, Julia, Anaerobic Biodegradation of Aromatic Hydrocarbons: Pathways and Prospects, Journal of Molecular Microbiology and Biotechnology, Jul. 28, 2008, pp. 93-120, vol. 15.
Jiang, Xin et al., Bacterial Diversity of Active Sludge in Wastewater Treatment Plant, Earth Science Frontiers, 2008, pp. 163-168, vol. 15, No. 6.
Mechichi, Tahar et al., Anaerobic degradation of methoxylated aromatic compounds by *Clostridium* methoxybenzovorans and a nitrate-reducing bacterium *Thauera* sp. Strain Cin3,4, International Biodeterioration & Biodegradation, 2005, pp. 224-230, vol. 56.
Song, Bongkeun et al., Characterization of halobenzoate-degrading, denitrifying *Azoarcus* and *Thauera* isolates and description of *Thauera chlorobenzoica* sp. nov., International Journal of Systematic and Evolutionary Microbiology, 2001, pp. 589-602, vol. 51.
Song, Bongkeun et al., Characterization of bacterial consortia capable of degrading 4-chlorobenzoate and 4-bromobenzoate under denitrifying conditions, FEMS Microbiology Letters, 2002, pp. 183-188, vol. 213.
Song, Bongkeun et al., Nitrite reductase genes in halobenzoate degrading denitrifying bacteria, FEMS Microbiology Ecology, 2003, pp. 349-357, vol. 43.
Thomsen, Trine Rolighed et al., Ecophysiology of abundant denitrifying bacteria in activated sludge, FEMS Microbiology Ecology, 2007, pp. 370-382, vol. 60.
Kianipey, S. A. et al., Mechanisms of Oil Displacement by Microorganisms, 61st Annual Technical Conference and Exhibition of the Society of Petroleum Engineers, SPE 15601, Oct. 5-8, 1986, New Orleans, LA, pp. 1-13.
Brown, L. R. et al., Slowing Production Decline and Extending the Economic Life of an Oil Field: New MEOR Technology, SPE/DOE Improved Oil Recovery Symposium, SPE 59306, Apr. 3-5, 2000, Tulsa, OK, pp. 1-16.

(Continued)

Primary Examiner — Brian J Gangle

(57) ABSTRACT

Enriched steady state microbial consortiums for microbial enhanced oil recovery and in situ bioremediation of hydrocarbon-contaminated sites, under anaerobic denitrifying conditions, are disclosed.

6 Claims, 6 Drawing Sheets

(56) References Cited

OTHER PUBLICATIONS

Figure 1:
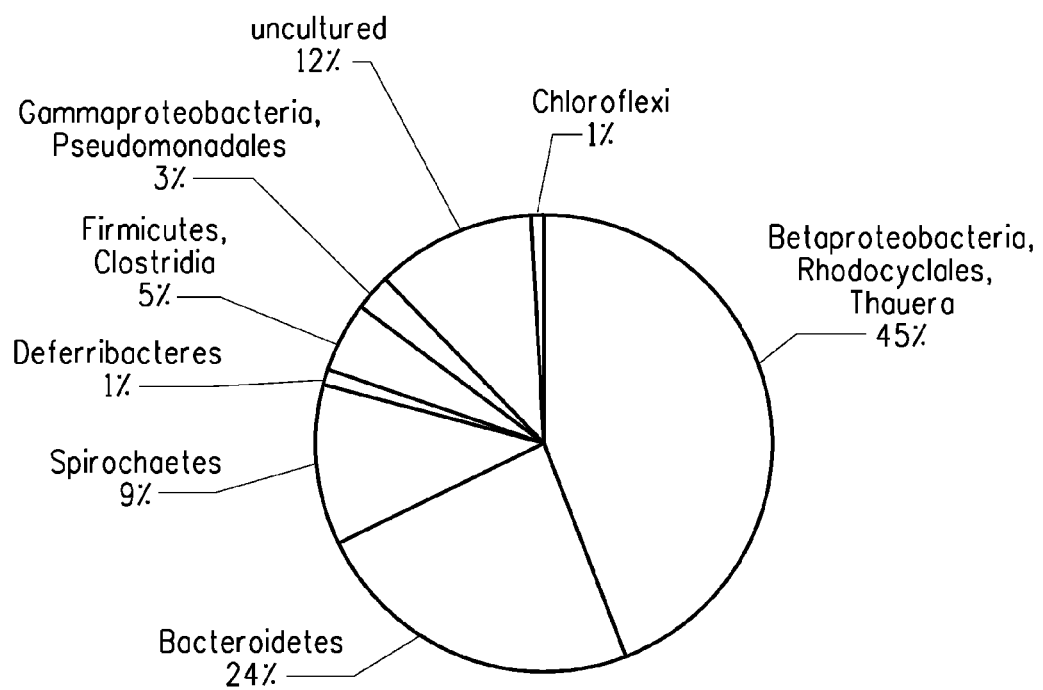

Sunde, Egil et al., Aerobic Microbial Enhanced Oil Recovery for Offshore Use, SPE/DOE Symposium on Enhanced Oil Recovery, SPE/DOE 24204, Apr. 22-24, 1992, Tulsa, OK, pp. 497-502.

Kowalewski, E. et al., Microbial improved oil recovery—bacterial induced wettability and interfacial tension effects on oil production, Journal of Petroleum Science & Engineering, 2006, pp. 275-286, vol. 52.

Office Action mailed Sep. 15, 2009, in co-pending U.S. Appl. No. 12/194,749.

Office Action mailed Mar. 9, 2009, in co-pending U.S. Appl. No. 12/204,205.

* cited by examiner

SEQUENCE LISTING

```
<160> NUMBER OF SEQ ID NOS: 87

<210> SEQ ID NO 1
<211> LENGTH: 20
<212> TYPE: DNA
<213> ORGANISM: artificial sequence
<220> FEATURE:
<223> OTHER INFORMATION: primer - 8F

<400> SEQUENCE: 1
agagtttgat ymtggctcag                                              20

<210> SEQ ID NO 2
<211> LENGTH: 19
<212> TYPE: DNA
<213> ORGANISM: artificial sequence
<220> FEATURE:
<223> OTHER INFORMATION: primer 1492R

<400> SEQUENCE: 2
ggwtaccttg ttacgactt                                               19

<210> SEQ ID NO 3
<211> LENGTH: 17
<212> TYPE: DNA
<213> ORGANISM: artificial sequence
<220> FEATURE:
<223> OTHER INFORMATION: primer 1407R

<400> SEQUENCE: 3 gacggggtg wgtrcaa                                                  17

<210> SEQ ID NO 4
<211> LENGTH: 17
<212> TYPE: DNA
<213> ORGANISM: artificial sequence
<220> FEATURE:
<223> OTHER INFORMATION: primer U518R
```

-continued

```
<400> SEQUENCE: 4
attaccgcgg ctgctgg                                                        17

<210> SEQ ID NO 5
<211> LENGTH: 17
<212> TYPE: DNA
<213> ORGANISM: artificial sequence
<220> FEATURE:
<223> OTHER INFORMATION: primer UB357F

<400> SEQUENCE: 5
cctacgggag gcagcag                                                        17

<210> SEQ ID NO 6
<211> LENGTH: 57
<212> TYPE: DNA
<213> ORGANISM: artificial sequence
<220> FEATURE:
<223> OTHER INFORMATION: primer dG UB 357F

<400> SEQUENCE: 6
cgcccgccgc gccccgcgcc cgtcccgccg ccccccgcccg cctacgggag gcagcag           57

<210> SEQ ID NO 7
<211> LENGTH: 16
<212> TYPE: DNA
<213> ORGANISM: artificial sequence
<220> FEATURE:
<223> OTHER INFORMATION: primer UA 341F1

<400> SEQUENCE: 7 taygggcgc agcagg                                                          16

<210> SEQ ID NO 8
<211> LENGTH: 58
<212> TYPE: DNA
<213> ORGANISM: artificial sequence
<220> FEATURE:
<223> OTHER INFORMATION: primer dG UA341F1

<400> SEQUENCE: 8
cgcccgccgc gccccgcgcc cgtcccgccg ccccccgcccg cctaygggc gcagcagg          58

<210> SEQ ID NO 9
<211> LENGTH: 18
<212> TYPE: DNA
<213> ORGANISM: artificial sequence
<220> FEATURE:
<223> OTHER INFORMATION: primer UA 341F2

<400> SEQUENCE: 9 cctacgggc gcagaggg                                                        18

<210> SEQ ID NO 10
<211> LENGTH: 58
<212> TYPE: DNA
<213> ORGANISM: artificial sequence
<220> FEATURE:
<223> OTHER INFORMATION: primer dG UA341F2

<400> SEQUENCE: 10
cgcccgccgc gccccgcgcc cgtcccgccg ccccccgcccg cctacgggc gcagaggg          58

<210> SEQ ID NO 11
<211> LENGTH: 18
```

```
<212> TYPE: DNA
<213> ORGANISM: artificial sequence
<220> FEATURE:
<223> OTHER INFORMATION: primer U519F

<400> SEQUENCE: 11
cagcmgccgc ggtaatwc                                                18

<210> SEQ ID NO 12
<211> LENGTH: 58
<212> TYPE: DNA
<213> ORGANISM: artificial sequence
<220> FEATURE:
<223> OTHER INFORMATION: primer U519F with 40 bp

<400> SEQUENCE: 12
cgcccgccgc gccccgcgcc cgtcccgccg ccccgcccg cagcmgccgc ggtaatwc       58

<210> SEQ ID NO 13
<211> LENGTH: 19
<212> TYPE: DNA
<213> ORGANISM: artificial sequence
<220> FEATURE:
<223> OTHER INFORMATION: primer UA958R

<400> SEQUENCE: 13
yccggcgttg amtccaatt                                               19

<210> SEQ ID NO 14
<211> LENGTH: 23
<212> TYPE: DNA
<213> ORGANISM: artificial sequence
<220> FEATURE:
<223> OTHER INFORMATION: primer UB 939R

<400> SEQUENCE: 14
cttgtgcggg ccccgtcat ttc                                           23

<210> SEQ ID NO 15
<211> LENGTH: 1510
<212> TYPE: DNA
<213> ORGANISM: unknown
<220> FEATURE:
<223> OTHER INFORMATION: Unknown clone from enriched environmental
      sample that by rDNA sequence analysis has highest identity to the
      genus Thauera

<400> SEQUENCE: 15
tggctcagat tgaacgctgg cggcatgctt tacacatgca agtcgaacgg cagcgggggc    60
ttcggcctgc cggcgagtgg cgaacgggtg agtaatgcat cggaacgtgc ccatgtcgtg   120
ggggataacg tatcgaaagg tacgctaata ccgcatacgt cctgagggag aaagcggggg   180
atcttcggac ctcgcgcgat tggagcggcc gatgtcggat tagctagtag gtgaggtaaa   240
ggctcaccta ggcgacgatc cgtagcgggt ctgagaggat gatccgccac actgggactg   300
agacacggcc cagactccta cgggaggcag cagtggggaa ttttggacaa tgggcgcaag   360
cctgatccag ccatgccgcg tgagtgaaga aggccttcgg gttgtaaagc tctttcggcc   420
gggaagaaat cgtggtctct aacataggcc atggatgacg gtaccggact aagaagcacc   480
ggctaactac gtgccagcag ccgcggtaat acgtagggtg cgagcgttaa tcggaattac   540
tgggcgtaaa gcgtgcgcag gcggttttgt aagacagatg tgaaatcccc gggctcaacc   600
tgggaactgc gtttgtgact gcaaggctag agtacgcagc aggggggtgg aattcctggt   660
gtagcagtga aatgcgtaga gatcaggagg aacaccgatg gcgaaggcag cccctggc    720
```

```
ctgtactgac gctcatgcac gaaagcgtgg ggagcaaaca ggattagata ccctggtagt    780
ccacgcccta aacgatgtcg actagtcgtt cggagcagca atgcactgag tgacgcagct    840
aacgcgtgaa gtcgaccgcc tgggagtac ggccgcaagg ttaaaactca aaggaattga    900
cggggacccg cacaagcggt ggatgatgtg gattaattcg atgcaacgcg aaaaacctta    960
cctacccttg acatgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccgaag gcgaattcg     1500 cggccgctaa                                                          1510

<210> SEQ ID NO 16
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      tThauera sp.R26885

<400> SEQUENCE: 16
tggctcagat tgaacgctgg cggcatgctt tacacatgca agtcgaacgg cagcgggggc    60
ttcggcctgc cggcgagtgg cgaacggtg agtaatgcat cggaacgtgc ccatgtcgtg    120
ggggataacg tatcgaaagg tacgctaata ccgcatacgc cctgaggggg aaagcggggg    180
attcttcgga acctcgcgcg attggagcgg ccgatgtcgg attagctagt aggtgaggta    240
aaggctcacc taggcgacga tccgtagcgg gtctgagagg atgatccgcc acactgggac    300
tgagacacgg cccagactcc tacgggaggc agcagtgggg aattttggac aatgggcgca    360
agcctgatcc agccatgccg cgtgagtgaa gaaggccttc gggttgtaaa gctctttcgg    420 ccggaagaa atcgcattct ctaatatagg atgtggatga cggtaccgga ctaagaagca    480
ccggctaact acgtgccagc agccgcggta atacgtaggg tgcgagcgtt aatctgaatt    540
actgggcgta aagcgtgcgc aggcggtttt gtaagacaga tgtgaaatcc ccgggcttaa    600
cctgggaact gcgtttgtga ctgcaaggct agagtacggc agagggggt ggaattcctg    660 gtgtagcagt gaaatgcgta gatatcggga ggatcaccta ggcgagggc agccccctgg    720 gcttgtactg acgctcatgc acgaaagcgt ggggagcaaa caggattaga tacccctggta    780 gtccacgccc taaacgatgt cgactagtcg ttcggagcag caatgcactg agtgacgcag    840
ctaacgcgtg aagtcgaccg cctggggagt acggccgcaa ggttaaaact caaaggaatt    900 gacgggggacc cgcacaagcg gtggatgatg tggattaatt cgatgcaacg cgaaaaacct    960
tacctaccct tgacatgtct ggaaccttgg tgagagccga gggtgccttc gggagccaga    1020
acacaggtgc tgcatggctg tcgtcagctc gtgtcgtgag atgttgggtt aagtcccgca    1080
acgagcgcaa cccttgtcat tagttgccat catttagttg gcactctaa tgagactgcc    1140 ggtgacaaac cggaggaagg tggggatgac gtcaagtcct catggcccctt atgggtaggg    1200
```

| cttcacacgt catacaatgg tcggtacaga gggttgccaa gccgcgaggt ggagccaatc | 1260 |
| ccttaaagcc gatcgtagtc cggatcgtag tctgcaactc gactacgtga agtcggaatc | 1320 |
| gctagtaatc gcagatcagc atgctgcggt gaatacgttc ccgggtcttg tacacaccgc | 1380 |
| ccgtcacacc atgggagtgg gtttcaccag aagtaggtag cttaaccttc gggagggcgc | 1440 |
| ttaccacggt gagattcatg actggggtga agtcgtaaca aggtaaccg | 1489 |

<210> SEQ ID NO 17
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. mXyN1
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t

<400> SEQUENCE: 17

| tggctcagat taaacgctgg cggcatgctt tacacatgca agtcgaacgg cagcggggc | 60 |
| ttcggcctgc cggcgagtgg cgaacggtg agtaatgcat cggaacgtgc ccatgtcgtg | 120 |
| ggggataacg tatcgaaagg tacgctaata ccgcatacgc cctgaggggg aaagcggggg | 180 |
| attcttcgga acctcgcgcg attggagcgg ccgatgtcgg attagctagt aggtgaggta | 240 |
| aaggctcacc taggcgacga tccgtagcgg gtctgagagg atgatccgcc acactgggac | 300 |
| tgagacacgg cccagactcc tacgggaggc agcagtgggg aattttggac aatgggcgca | 360 |
| agcctgatcc agccatgccg cgtgagtgaa gaaggccttc gggttgtaaa gctctttcgg | 420 |
| ccgggaagaa atcgcattct ctaatatagg atgtggatga cggtaccgga ctaagaagca | 480 |
| ccggctaact acgtgccagc agccgcggta atacgtaggg tgcgagcgtt aatcggaatt | 540 |
| actgggcgta aagcgtgcgc aggcggtttt gtaagacaga tgtgaaatcc ccgggcttaa | 600 |
| cctgggaact gcgtttgtga ctgcaaggct agagtacggc agaggggggt ggaattcctg | 660 |
| gtgtancant gaaatgcgta aatatcagga ggaacaccga tggcgaaggc agccccctgg | 720 |
| gcctgtactg acgctcatgc acgaaagggt ggggagcaaa caggattaga tacccctggta | 780 |
| gtccacgccc taaacgatgt cgactagtcg ttcggagcag caatgcactg agtgacgcag | 840 |
| ctaacgcgtg aagtcgaccg cctggggagt acggccgcaa ggttaaaact caaaggaatt | 900 |
| gacgggggacc cgcacaagcg gtggatgatg tggattaatt cgatgcaacg cgaaaaacct | 960 |
| tacctacccct tgacatgcca ggaaccttgc cgagaggcga gggtgccttc gggagcctgg | 1020 |
| acacaggtgc tgcatggctg tcgtcagctc gtgtcgtgag atgttgggtt aagtcccgca | 1080 |
| acgagcgcaa cccttgtcac tagttgccat catttggttg ggcactctag tgagactgcc | 1140 |
| ggtgacaaac cggaggaagg tggggatgac gtcaagtcct catggccctt atgggtaggg | 1200 |
| cttcacacgt catacaatgg tcggtacaga gggttgccaa gccgcgaggt ggagccaatc | 1260 |
| ccttaaagcc gatcgtagtc cggatcgtag tctgcaactc gactacgtga agtcggaatc | 1320 |
| gctagtaatc gcagatcagc atgctgcggt gaatacgttc ccgggtcttg tacacaccgc | 1380 |
| ccgtcacacc atgggagtgg gtttcaccag aagtaggtag cttaaccttc gggagggcgc | 1440 |
| ttaccacggt gagattcatg actggggtga agtcgtaaca aggtaaccg | 1489 |

<210> SEQ ID NO 18
<211> LENGTH: 1487
<212> TYPE: DNA
<213> ORGANISM: unknown
<220> FEATURE:
<223> OTHER INFORMATION: unkown clone
<220> FEATURE:
<221> NAME/KEY: misc_feature
<222> LOCATION: (939)..(939)
<223> OTHER INFORMATION: n is a, c, g, or t

<400> SEQUENCE: 18

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgc cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttgtaaagc tctttcggcc     420
gggaagaaat cgcattctct aatataggat gtggatgacg gtaccggact aagaagcacc     480
ggctaactac gtgccagcag ccgcggtaat acgtagggtg cgagcgttaa tcggaattac     540
tgggcgtaaa gcgtgcgcag gcggttttgt aagacagatg tgaaatcccc gggcttaacc     600
tgggaactgc gtttgtgact gcaaggctag agtacggcag agggggggtgg aattcctggt     660
gtaccagtga aatgcgtaaa gatcaagacg aacaccgatg gcgaaggcag ccccctgggc     720
ctgtactgac gctcatgcac aaaagcgtgg ggagcaaaca ggattagata ccctggtagt     780
ccacgcccta aacgatttcg actagtcgtt tggagcagca atgcactgag tgacgcagct     840
aacgcgtgaa gtcgaccgcc tggggagtac ggccgcaagg ttaaaactca aaggaattga     900
cggggacccg cacaagcggt ggatgatgtg gattaattng atgcaacgcg aaaaacctta     960
cctacccttg acatgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttgtcatta gttgccatca tttagttggg cactctaatg agactgccgg    1140
tgacaaaccg gaggaaggtg gggatgacgt caagtcatca tggcccttac ggcctgggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                  1487
```

<210> SEQ ID NO 19
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera sp. R26885

<400> SEQUENCE: 19

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
```

```
ggggataacg tatcgaaagg tacgctaata ccgcatacgt cctgaggag  aaagcggggg      180 attcttcgga acctcgcgcg attggagcgg ccgatgtcgg attagctagt aggtgaggta      240
aaggctcacc taggcgacga tccgtagcgg gtctgagagg atgatccgcc acactgggac      300
tgagacacgg cccagactcc tacgggaggc agcagtgggg aattttggac aatgggggca      360
accctgatcc agccatgccg cgtgagtgaa gaaggccttc gggttgtaaa gctctttcgg      420
ccgggaagaa atcgcgcact ctaacatagt gtgtggatga cggtaccgga ctaagaagca      480
ccggctaact acgtgccagc agccgcggta atacgtaggg tgcgagcgtt aatcggaatt      540
actgggcgta aagcgtgcgc aggcggtttt gtaagacgga tgtgaaatcc ccgggctcaa      600
cctgggaact gcgtttgtga ctgcaaggct agagtacggc agaggggggt ggaattcctg      660
gtgtagcagt gaaatgcgta gatatcagga ggaacaccga tggcgaaggc agcccctgg       720 gcctgtactg acgctcatgc acgaaagcgt ggggagcaaa caggattaga taccctggta      780
gtccacgccc taaacgatgt cgactagtcg ttcggagcag caatgcactg agtgacgcag      840
ctaacgcgtg aagtcgaccg cctggggagt acggccgcaa ggttaaaact caaaggaatt      900
gacggggacc cgcacaagcg gtggatgatg tggattaatt cgatgcaacg cgaaaaacct      960
tacctaccct tgacatgtct ggaaccttgg tgagagccga gggtgccttc gggagccaga     1020
acacaggtgc tgcatggctg tcgtcagctc gtgtcgtgag atgttgggtt aagtcccgca     1080
acgagcgcaa cccttgtcac tagttgccat catttggttg ggcactctag tgagactgcc     1140
ggtgacaaac cggaggaagg tggggatgac gtcaagtcct catggccctt atgggtaggg     1200
cttcacacgt catacaatgg tcggtacaga gggttgccaa gccgcgaggt ggagccaatc     1260
ccttaaagcc gatcgtagtc cggatcgtag tctgcaactc gactacgtga agtcggaatc     1320
gctagtaatc gcagatcagc atgctgcggt gaatacgttc ccgggtcttg tacacaccgc     1380
ccgtcacacc atgggagtgg gtttcaccag aagtaggtag cttaaccttc gggagggcgc     1440
ttaccacggt gagattcatg actggggtga agtcgtaaca aggtaaccg               1489
```

<210> SEQ ID NO 20
<211> LENGTH: 894
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 20

```
cttaacctgg gaactgcgtt tgtgactgca aggctagagt acggcagagg ggggtggaat       60
tccacgtgta acagtgaaat gcgtagagat gtggaggaac accgatggcg aaggcagccc      120
cctgggcctg tactgacgct catgcacgaa agcgtgggga gcaaacagga ttagataccc      180
tggtagtcca cgccctaaac gatgtcgact agtcgttcgg agcagcaatg cactgagtga      240
cgcagctaac gcgtgaagtc gaccgcctgg ggagtacggc cgcaaggtta aaactcaaag      300
gaattgacgg ggacccgcac aagcggtgga tgatgtggat taattcgatg caacgcgaaa      360
aaccttacct acccttgaca tgtctggaac cttggtgaga gccgagggtg ccttcgggag      420
ccagaacaca ggtgctgcat ggctgtcgtc agctcgtgtc gtgagatgtt gggttaagtc      480
ccgcaacgag cgcaacccct tgtcactagt tgccatcattt ggttgggcac tctagtgaga      540
ctgccggtga caaccggag gaaggtgggg atgacgtcaa gtcctcatgg cccttatggg       600
tagggcttca cacgtcatac aatggtcggt acagagggtt gccaagccgc gaggtggagc      660
```

```
caatcccttc aagccgatcg tagtccggat cgtagtctgc aactcgacta cgtgaagtcg    720
gaatcgctag taatcgcaga tcagcatgct gcggtgaata cgttcccggg tcttgtacac    780
accgcccgtc acaccatggg agtgggtttc accagaagta ggtagcttaa ccttcgggag    840
ggcgcttacc acggtgagat tcatgactgg ggtgaagtcg taacaaggta accg          894
```

<210> SEQ ID NO 21
<211> LENGTH: 1486
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera sp. R26885

<400> SEQUENCE: 21

```
tggctcagat tgaacgctgg cggcatgctt tacacatgca agtcgaacgg cagcggggc    60 ttcggcctgc cggcgagtgg cgaacgggtg agtaatgcat cggaacgtgc ccatgtcgtg   120
ggggataacg tatcgaaagg tacgctaata ccgcatacgt cctgagggag aaagcggggg   180
atcttcggac ctcgcgcgat tggagcggcc gatgtcggat tagctagtag gtgaggtaaa   240
ggctcaccta ggcgacgatc cgtagcgggt ctgagaggat gatccgccac actgggactg   300
agacacggcc cagactccta cgggaggcag cagtggggaa ttttggacaa tgggcgcaag   360
cctgatccag ccatgccgcg tgagtgaaga aggccttcgg gttgtaaagc tctttcggcc   420
gggaagaaat cgtggtctct aacatgggcc atggatgacg gtaccggact aagaagcacc   480
ggctaactac gtgccagcag ccgcggtaat acgtagggtg cgagcgttaa tcggaattac   540
tgggcgtaaa gcgtgcgcag gcggttttgt aagacagatg tgaaatcccc gggctcaacc   600
tgggaactgc gtttgtgact gcaaggctag agtacggcag agggggtgg aattcctggt   660 gtagcagtga aatgcgtaaa gatcaggagg aacaccgagg ggaaggcagc cccctgggcc   720
tgtatgaagg ctcaggcagg aaagcgtggg gagcaaacag gaatagatac cctggtagtc   780
cacgccctaa acgatgtcga ctagtcgttc ggagcagcaa tgcactgagt gacgcagcta   840
acgcgtgaag tcgaccgcct ggggagtacg gccgcaaggt taaaactcaa aggaattgac   900
ggggacccgc acaagcggtg gatgatgtgg attaattcga tgcaacgcga aaaaccttac   960 ctaccccttga catgtctgga accttggtga gagccgaggg tgccttcggg agccagaaca  1020
caggtgctgc atggctgtcg tcagctcgtg tcgtgagatg ttgggttaag tcccgcaacg  1080
agcgcaaccc ttgtcactag ttgccatcat ttggttgggc actctagtga gactgccggt  1140
gacaaaccgg aggaaggtgg ggatgacgtc aagtcctcat ggcccttatg ggtagggctt  1200
cacacgtcat acaatggtcg gtacagaggg ttgccaagcc gcgaggtgga gccaatccca  1260
aaaagccgat cgtagtccgg atcgtagtct gcaactcgac tacgtgaagt cggaatcgct  1320
agtaatcgca gatcagcatg ctgcggtgaa tacgttcccg ggtcttgtac acaccgcccg  1380
tcacaccatg ggagtgggtt tcaccagaag taggtagctt aaccttcggg agggcgctta  1440
ccacggtgag attcatgact ggggtgaagt cgtaacaagg taaccg                   1486
```

<210> SEQ ID NO 22
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. mXyN1

<400> SEQUENCE: 22

```
tggctcagat tgaacgctgg cggcatgctt tacacatgca agtcgaacgg cagcggggc       60 ttcggcctgc cggcgagtgg cgaacgggtg agtaatgcat cggaacgtgc ccatgtcgtg      120
ggggataacg tatcgaaagg tacgctaata ccgcatacgt cctgagggag aaagcggggg     180
attcttcgga acctcgcgcg attggagcgg ccgatgtcgg attagctagt aggtgaggta      240
aaggctcacc taggcgacga tccgtagcgg gtctgagagg atgatccgcc acactgggac      300
tgaggcacgg cccagactcc tacgggaggc agcagtgggg aattttggac aatgggggca      360
accctgatcc agccatgccg cgtgagtgaa gaaggccttc gggttgtaaa gctctttcgg      420
ccgggaagaa atcgcgcact ctaacatagt gtgtggatga cggtaccgga ctaagaagca      480
ccggctaact acgtgccagc agccgcggta atacgtaggg tgcgagcgtt aatcggaatt      540
actgggcgta aagcgtgcgc aggcggtttt gtaagacaga tgtgaaatcc ccgggctcaa      600
cctgggaact gcgtttgtga ctgcaaggct agagtacggc agaggggggt ggaattcctg      660
gtgtagcagt gaaatgcgta gatatcagga ggaacaccga tggcgaaggc agccccctgg      720
gcctgtactg acgctcatgc acgaaagcgt ggggagcaaa caggattaga taccctggta      780
gtccacgccc taaacgatgt cgactagtcg ttcggagcag caatgcactg agtgacgcag      840
ctaacgcgtg aagtcgaccg cctggggagt acggccgcaa ggttaaaact caaaggaatt      900
gacggggacc cgcacaagcg gtggatgatg tggattaatt cgatgcaacg cgaaaaacct      960
tacctaccct tgacatgcca ggaaccttgc cagaggcga gggtgccttc gggagcctgg     1020
acacaggtgc tgcatggctg tcgtcagctc gtgtcgtgag atgttgggtt aagtcccgca     1080
acgagcgcaa cccttgtcac tagttgccat catttggttg ggcactctag tgagactgcc     1140
ggtgacaaac cggaggaagg tggggatgac gtcaagtcct catggccttt atgggtaggg     1200
cttcacacgt catacaatgg tcggtacaga ggttgccaa ccgcgaggt ggagccaatc      1260 ccttaaagcc gattgtagtc cggatcgtag tctgcaactc gactacgtga agtcggaatc     1320
gctagtaatc gcagatcagc atgctgcggt gaatacgttc ccgggtcttg cacacaccgc     1380
ccgtcacacc atgggagtgg gtttcaccag aagtaggtag cttaaccttc gggagggcgc     1440
ttaccacggt gagattcatg actggggtga agtcgtaaca aggtaaccg               1489
```

```
<210> SEQ ID NO 23
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica
```

<400> SEQUENCE: 23

```
tggctcagat tgaacgctgg cggcatgctt tacacatgca agtcgaacgg cagcggggc       60 ttcggcctgc cggcgagtgg cgaacgggtg agtaatgcat cggaacgtgc ccatgtcgtg      120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa      240
ggctcaccta ggcgacgatc cgtagcgggt ctgagaggat gatccgccac actgggactg      300
agacacggcc cagactccta cgggaggcag cagtggggaa ttttggacaa tgggcgcaag      360
cctgatccag ccatgccgcg tgagtgaaga aggccttcgg gttataaagc tctttcggcc      420
gggaagaaat cgtggtctct aacataggcc atggatgacg gtaccggact aagaagcacc      480
```

```
ggctaactac gtgccagcag ccgcggtaat acgtagggtg cgagcgttaa tcggagttac    540
tgggcgtaaa gcgtgcgcag gcggttttgt aagacagatg tgaaatcccc gggctcaacc    600
tgggaactgc gtttgtgact gcaaggctag agtacggcag aggggggtgg aattcctggt    660
gtaacagtga aatgcgtaga gatcaggagg aacaccgatg gcgaaggcag ccccctgggc    720
ctgtactgac gctcatgcac gaaagcgtgg ggagcaaaaa ggattaaata ccctggtagt    780
ccacgcccta aacgatgtcg actagtcgtt cggagcagca atgcactgag tgacgcagct    840
aacgcgtgaa gtcgaccgcc tggggagtac ggccgcaagg ttaaaactca aaggaattga    900
cggggacccg cacaagcggt ggatgatgtg gattaattcg atgcaacgcg aaaaacctta    960 cctaccctttg acatgccagg aaccttgccg agaggcgagg gtgccttcgg gagcctggac   1020
acaggtgctg catggctgtc gtcagctcgt gtcgtgagat gttgggttaa gtcccgcaac   1080
gagcgcaacc cttgtcacta gttgccatca tttggttggg cactctagtg agactgccgg   1140
tgacaaaccg gaggaaggtg gggatgacgt caagtcctca tggcccttat ggtagggct    1200 tcacacgtca tacaatggtc ggtacagagg gttgccaagc cgcgaggtgg agccaatccc   1260
ttaaagccga tcgtagtccg gatcgtagtc tgcaactcga ctacgtgaag tcggaatcgc   1320
tagtaatcgc agatcagcat gctgcggtga atacgttccc gggtcttgta cacaccgccc   1380
gtcacaccat gggagtgggt ttcaccagaa gtaggtagct taaccttcgg gagggcgctt   1440
accacggtga gattcatgac tggggtgaag tcgtaacaag gtaaccg                 1487
```

<210> SEQ ID NO 24
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 24

```
tggctcagat tgaacgctgg cggcatgctt tgcacatgca agtcgaacgg cagcgggggc     60
ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcagcc    600
tgggaactgc gtttgtgact gcaaggctag agtacggcag aggggggtgg aattcctggt    660
gtagcagtga aatgcgttga gatcaggagg aacaccgatg gcgaaggcag ccccctgggc    720
ctgtactgac gctcatgtac aaaagcgtgg ggagcaaaca ggattagata ccctggtagt    780
ccacgcccta aacgatgtcg actagtcgtt cggagcagca atgcactgag tgacgcagct    840
aacgcgtgaa gtcgaccgcc tggggagtac ggccgcaagg ttaaaactca aaggaattga    900
cggggacccg cacaagcggt ggatgatgtg gattaattcg atgcaacgcg aaaaacctta    960
cctacccttg acatgccagg aaccttgccg agaggcgagg gtgccttcgg gagcctggac   1020
```

```
acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                  1487
```

<210> SEQ ID NO 25
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 25

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttgtaaagc tctttcggcc     420
gggaagaaat cgtggtctct aacataggcc atggatgacg gtaccggact aagaagcacc     480
ggctaactac gtgccagcag ccgcggtaat acgtagggtg cgagcgttaa tcggaattac     540
tgggcgtaaa gcgtgcgcag gcggttttgt aagacagatg tgaaatcccc gggctcaacc     600
tgggaactgc gtttgtgact gcaaggctag agtacggcag agggggggtgg aattcctggt     660 ttagcagtga aatgcgtaga gatcaagagg aacaccgatg gcgaaggcag ccccctgggc     720
ctgtactgac gctcatgcac gaaagcgtgg ggagcaaaca ggattagata ccctggtagt     780
ccacgcccta aacgatgtcg actagtcgtt cggagcagca atgcactgag tgacgcagct     840
aacgcgtgaa gtcgaccgcc tggggagtac ggccgcaagg ttaaaactca aaggaattga     900
cggggacccg cacaagcggt ggatgatgtg gattaattcg atgcaacgcg aaaaacctta     960
cctacccttg acatgccagg aaccttgccg agaggcgagg gtgccttcgg agcctggac    1020 acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                  1487
```

```
<210> SEQ ID NO 26
<211> LENGTH: 1487
<212> TYPE: DNA
<213> ORGANISM: unknown
<220> FEATURE:
<223> OTHER INFORMATION: unknown clone

<400> SEQUENCE: 26
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttgtaaagc tctttcggcc     420
gggaagaaat cgtggtctct aacataggcc atggatgacg gtaccggact aagaagcacc     480
ggctaactac gtgccagcag ccgcggtaat acgtagggtg cgagcgttaa tcggaattac     540
tgggcgtaaa gcgtgcgcag gcggttttgt aagacagatg tgaaatcccc gggctcaacc     600
tgggaactgc gtttgtgact gcaaggctag agtacggcag agggggtgg aattcctggt      660 gtagcagtga aatgcgtaga gatcaagagg aacaccgatg gcgaaggcag ccccctgggc     720
ctgtactgac gctcatgcac gaaagcgtgg ggagcaaaca ggattagata ccctggtagt     780
ccacgcccta aacgatgtcg actagtcgtt cggagcagca atgcactgag tgacgcagct     840
aacgcgtgaa gtcgaccgcc tggggagtac ggccgcaagg ttaaaactca aaggaattga     900
cggggacccg cacaagcggt ggatgatgtg gattaattcg atgcaacgcg aaaaacctta     960
cctacccttg acctgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttatcacta gttgccatca tttggttggg cactctagtg agactgccgg    1140
tgacaaaccg gaggaaggtg gggatgacgt caagtcctca tggcccttat ggtagggct     1200 tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                  1487

<210> SEQ ID NO 27
<211> LENGTH: 1488
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 27
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
```

```
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag agggggtgg aattcctggt       660 gtagcagtga aatgcgtaga gatcaagagg aacaccgatg gcggaagcag ccccctggg       720 cctgtactga cgttcatgca cgaaagcgtg gggagcaaac aggattagat acctggtaag      780
tccacgccct aaacgatgtc gactagtcgt tcggagcagc aatgcactga gtgacgcagc      840
taacgcgtga agtcgaccgc ctggggagta cggccgcaag gttaaaactc aaaggaattg      900
acggggaccc gcacaagcgg tggatgatgt ggattaattc gatgcaacgc gaaaaacctt      960 acctacccctt gacatgccag gaaccttgcc gagaggcgag ggtgcttcg ggagcctgga     1020 cacaggtgct gcatggctat cgtcagctcg tgtcgtgaga tgttgggtta agtcccgcaa     1080
cgagcgcaac ccttgtcact agttgccatc atttggttgg gcactctagt gagactgccg     1140
gtgacaaacc ggaggaaggt ggggatgacg tcaagtcctc atggcccttaa tgggtagggc     1200 ttcacacgtc atacaatggt cggtacagag ggttgccaag ccgcgaggtg gagccaatcc     1260
cttaaagccg atcgtagtcc ggatcgtagt ctgcaactcg actacgtgaa gtcggaatcg     1320
ctagtaatcg cagatcagca tgctgcggtg aatacgttcc cgggtcttgt acacaccgcc     1380
cgtcacacca tgggagtggg tttcaccaga agtaggtagc ttaaccttcg ggagggcgct     1440
taccacggtg agattcatga ctggggtgaa gtcgtaacaa ggtaaccg                   1488

<210> SEQ ID NO 28
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 28
tggctcagat tgaacgctgg cggcatgctt tacacatgca agtcgaacgg cagcggggc       60 ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag agggggtgg aatttctggt       660 gtagcagtaa aatgcgtaga gatcaagagg aacaccgtat ggcgaagcca gcccctgggg     720
cttgtactga cgttcatgca cgaaagggtg gggagcaaac aggattagat accctggta     780 gtccacgccc taaacgatgt cgactagtcg ttcggagcag caatgcactg agtgacgcag    840
```

```
ctaacgcgtg aagtcgaccg cctggggagt acggccgcaa ggttaaaact caaaggaatt    900
gacggggacc cgcacaagcg gtggatgatg tggattaatt cgatgcaacg cgaaaaacct    960
tacctaccct tgacatgcca ggaaccttgc cgagaggcga gggtgccttc gggagcctgg   1020
acacaggtgc tgcatggctg tcgtcagctc gtgtcgtgag atgttgggtt aagtcccgca   1080
acgagcgcaa cccttgtcac tagttgccat catttggttg ggcactctag tgagactgcc   1140
ggtgacaaac cggaggaagg tggggatgac gtcaagtcct catggccctt atgggtaggg   1200
cttcacacgt catacaatgg tcggtacaga gggttgccaa gccgcgaggt ggagccaatc   1260
ccttaaagcc gatcgtagtc cggatcgtag tctgcaactc gactacgtga agtcggaatc   1320
gctagtaatc gcagatcagc atgctgcggt gaatacgttc ccgggtcttg tacacaccgc   1380
ccgtcacacc atgggagtgg gttttaccag aagtaggtag cttaaccttc gggagggcgc   1440
ttaccacggt gagattcatg actggggtga agtcgtaaca aggtaaccg               1489
```

<210> SEQ ID NO 29
<211> LENGTH: 749
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus ap. EH10

<400> SEQUENCE: 29

```
tggctcagat cgaacgctgg cggcatgctt tacacatgca agtcgaacgg cagcggggc    60 ttcggcctgc cggcgagtgg cgaacgggtg agtaatgcat cggaacgtgc ccatgtcgtg   120
ggggataacg tatcgaaagg tacgctaata ccgcatacgc cctgagggg aaagcggggg    180 attcttcgga acctcgcgcg attggagcgg ccgatgtcgg attagctagt aggtgaggta   240
aaggctcacc taggcgacga tccgtagcgg gtctgagagg atgatccgcc acactgggac   300
tgagacacgg cccagactcc tacgggaggc agcagtgggg aattttggac aatggggca   360 accctgatcc agccatgccg cgtgagtgaa gaaggccttc gggttgtaaa gctctttcgg   420
ccgggaagaa atcgcgcact ctaacatagt gtgtggatga cggtaccgga ctaagaagca   480
ccggctaact acgtgccagc agccgcggta atacgtaggg tgcgagcgtt aatcggaatt   540
actgggcgta aagcgtgcgc aggcggtttt gtaagacaga tgtgaaatcc ccgggctcaa   600
cctgggaact gcgtttgtga ctgcaaggct agagtacggc agaggggggt ggaattcctg   660
gtgtagcagt gaaatgcgta aatatcagga ggaacaccga tggcgaaggc agcccctgg    720 gcctgtactg acgctcatgc acgaaagcg                                    749
```

<210> SEQ ID NO 30
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera sp. R26885

<400> SEQUENCE: 30

```
tggctcagat tgaacgctgg cggcatgctt tacacatgca agtcgaacgg cagcggggc    60 ttcggcctgc cggcgagtgg cgaacgggtg agtaatgcat cggaacgtgc ccatgtcgtg   120
ggggataacg tatcgaaagg tacgctaata ccgcatacgt cctgagggag aaagcggggg   180
atcttcggac ctcgcgcgat tggagcggcc gatgtcggat tagctagtag gtgaggtaaa   240
```

```
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gtggttttgt aagacagatg tgaaatcccc gggctcaacc    600
tgggaactgc gtttgtgact gcaaggctag agtacggcag agggggtgg aattcctggt    660 gtagcagtga aatgcgtaaa gatcaagagg aacaccgatg gcgaaggcag ccccctgggc    720
ctgtactgac gttcatgcac gaaagcgtgg ggagcaaaca ggattagata ccctggtagt    780
ccacgcccta aacgatgtcg actagtcgtt cggagcagca atgcactgag tgacgcagct    840
aacgcgtgaa gtcgaccgcc tggggagtac ggccgcaagg ttaaaactca aaggaattga    900
cggggacccg cacaagcggt ggatgatgtg gattaattcg atgcaacgcg aaaaacctta    960 cctaccttg acatgtctgg aaccttggtg agagccgagg gtgccttcgg gagccagaac   1020
acaggtgctg catggctgtc gtcagctcgt gtcgtgagat gttgggttaa gtcccgcaac   1080
gagcgcaacc cttgtcatta gttgccatca tttagttggg cactctaatg agactgccgg   1140
tgacaaaccg gaggaaggtg gggatgacgt caagtcctca tggcccttat gggtagggct   1200
tcacacgtca tacaatggtc ggtacagagg gttgccaagc cgcgaggtgg agccaatccc   1260
ttaaagccga tcgtagtccg gatcgtagtc tgcaactcga ctacgtgaag tcggaatcgc   1320
tagtaatcgc agatcagcat gctgcggtga atacgttccc gggtcttgta cacaccgccc   1380
gtcacaccat gggagtgggt ttcaccagaa gtaggtagct taaccttcgg gagggcgctt   1440
accacggtga gattcatgac tggggtgaag tcgtaacaag gtaaccg                 1487
```

<210> SEQ ID NO 31
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 31

```
tggctcagat tgaacgctgg cggcatgctt tacacatgca agtcgaacgg cagcgggggc     60
ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat taactagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagagtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggtgg aattcctggt    660 gtagcagtga aatgcgtaaa gatcaagagg aacaccgatg gcgaatgcaa ccccctgggc    720
ctgtactgac gctcatgcac gaaagcgtgg ggagcaaaca ggattagata ccctggtagt    780
```

```
ccacgccta  aacgatgtcg  actagtcgtt  cggagcagca  atgcactgag  tgacgcagct   840
aacgcgtgaa  gtcgaccgcc  tggggagtac  ggccgcaagg  ttaaaactca  aaggaattga   900
cggggacccg  cacaagcggt  ggatgatgtg  gattaattcg  atgcaacgcg  aaaaacctta   960
cctacccttg  acatgccagg  aaccttgccg  agaggcgagg  gtgccttcgg  gagcctggac  1020
acaggtgctg  catggctgtc  gtcagctcgt  gtcgtgagat  gttgggttaa  gtcccgcaac  1080
gagcgcaacc  cttgtcacta  gttgccatca  tttggttggg  cactctagtg  agactgccgg  1140
tgacaaaccg  gaggaaggtg  gggatgacgt  caagtcctca  tggcccttat  gggtagggct  1200
tcacacgtca  tacaatggtc  ggtacagagg  gttgccaagc  cgcgaggtgg  agccaatccc  1260
ttaaagccga  tcgtagtccg  gatcgtagtc  tgcaactcga  ctacgtgaag  tcggaatcgc  1320
tagtaatcgc  agatcagcat  gctgcggtga  atacgttccc  gggtcttgta  cacaccgccc  1380
gtcacaccat  gggagtgggt  ttcaccagaa  gtaggtagct  taaccttcgg  gagggcgctt  1440
accacggtga  gattcatgac  tggggtgaag  tcgtaacaag  gtaaccg                 1487
```

<210> SEQ ID NO 32
<211> LENGTH: 1499
<212> TYPE: DNA
<213> ORGANISM: unknown
<220> FEATURE:
<223> OTHER INFORMATION: Unknown clone from enriched environmental sample that by rDNA sequence analysis has highest identity to Thauera aromatica

<400> SEQUENCE: 32

```
cggttacctt  gttacgactt  cacccagtc   atgaatctca  ccgtggtaag  cgccctcccg    60
aaggttaagc  tacctacttc  tggtgaaacc  caccccatg   gtgtgacggg  cggtgtgtac   120
aagacccggg  aacgtattca  ccgcagcatg  ctgatctgcg  attactagcg  attccgactt   180
cacgtagtcg  agttgcagac  tacgatccgg  actacgatcg  gctttaaggg  attggctcca   240
cctcgcggct  tggcaaccct  ctgtaccgac  cattgtatga  cgtgtgaagc  cctacccata   300
agggccatga  ggacttgacg  tcatccccac  cttcctccgg  tttgtcaccg  gcagtctcac   360
tagagtgccc  aaccaaatga  tggcaactag  tgacaagggt  tgcgctcgtt  gcgggactta   420
acccaacatc  tcacgacacg  agctgacgac  agccatgcag  cacctgtgtc  caggctcccg   480
aaggcaccct  cgcctctcgg  caaggttcct  ggcatgtcaa  gggtaggtaa  ggttttttcgc   540 gttgcatcga  attaatccac  atcatccacc  gcttgtgcgg  gtccccgtca  attcctttga   600 gtttaacct   tgcggccgta  ctccccaggc  ggtcgacttc  acgcgttagc  tgcgtcactc   660
agtgcattgc  tgctccgaac  gactagtcga  catcgtttag  ggcgtggact  accagggtat   720
ctaatcctgt  ttgctcccca  cgctttcgtg  catgagcgtc  agtacaggcc  caggggggctg   780 ccttcgccat  cggtgttcct  cctgatctct  gcgcatttca  ctgctacacc  aggaattcca   840 ccccctctg   ccgtactcta  gccttgcagt  cacaaacgca  gttcccaggt  tgagcccggg   900
gatttcacat  ctgtcttaca  aaaccgcctg  cgcacgcttt  acgccagta   attccgatta   960 acgctcgcac  cctacgtatt  accgcggctg  ctggcacgta  gttagccggt  gcttcttagt  1020
ccggtaccgt  catccatggc  ctatgttaga  gaccacgatt  tcttcccggc  cgaaagagct  1080
ttacaacccg  aaggccttct  tcactcacgc  ggcatggctg  gatcaggctt  gcgcccattg  1140
tccaaaattc  cccactgctg  cctcccgtag  gagtctgggc  cgtgtctcag  tcccagtgtg  1200
gcggatcatc  ctctcagacc  cgctacggat  cgtcgcctag  gtgagccttt  acctcaccta  1260
ctagctaatc  cgacatcggc  cgctccaatc  gcgcgaggtc  cgaagatccc  ccgctttctc  1320
```

```
cctcaggacg tatgcggtat tagcgtacct ttcgatacgt tatcccccac gacatgggca   1380
cgttccgatg cattactcac ccgttcgcca ctcgccggca ggccgaagcc cccgctgccg   1440
ttcgacttgc atgtgtaaag catgccgcca gcgttcaatc tgagccatga tcaaactct    1499

<210> SEQ ID NO 33
<211> LENGTH: 1429
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 33
tgaacgctgg cggcatgctt tacacatgca agtcgaacgg cagcgggggc ttcggcctgc     60
cggcgagtgg cgaacgggtg agtaatgcat cggaacgtgc ccatgtcgtg gggataacg    120 tatcgaaagg tacgctaata ccgcatacgt cctgagggag aaagcggggg attttcggac   180
ctcgcgcgat tggagcggcc gatgtcggat tagctagtag gtgaggtaaa ggctcaccta   240
ggcgacgatc cgtagcgggt ctgagaggat gatccgccac actgggactg agacacggcc   300
cagactccta cgggaggcag cagtgggaa ttttggacaa tgggcgcaag cctgatccag    360
ccatgccgcg tgagtgaaga aggccttcgg gttgtaaagc tctttcggcc gggaagaaat   420
cgtggtctct aacataggcc atggatgacg gtaccggact aagaagcacc ggctaactac   480
gtgccagcag ccgcggtaat atgtaggtgt cgagcgttaa tcggaattac tgggcgtaaa   540
gcgtgcgcag gcggttttgt aagacagatg tgaaatcccc gggctcaacc tgggaactgc   600
gtttgtgact gcaaggctag agtacggcgg aggggggtgg aattcctggt gtagcagtga   660
aatgcgtaga gatcaggagg aacaccgatg gcgaaggcag ccccctgggc ctgtactgac   720
gctcatgcac gaaagcgtgg ggagcaaaca ggattagata ccctggtagt ccacgcccta   780
aacgatgtcg actagtcgtt cggagcagca atgcactgag tgacgcagct aacgcgtgaa   840
gtcgaccgcc tggggagtac ggccgcaagg ttaaaactca aaggaattga cggggacccg   900
cacaagcggt ggatgatgtg gattaattcg atgcaacgcg aaaaacctta cctacccttg   960
acatgccagg aaccttgccg agaggcgagg gtgccttcgg gagcctggac acaggtgctg  1020
catggctgtc gtcagctcgt gtcgtgagat gttgggttaa gtcccgcaac gagcgcaacc  1080
cttgtcacta gttgccatca tttggttggg cactctagtg agactgccgg tgacaaaccg  1140
gaggaaggtg gggatgacgt caagtcctca tggcccttat gggtagggct tcacacgtca  1200
tacaatggtc ggtacagagg gttgccaagc cgcgaggtgg agccaatccc ttaaagccga  1260
tcgtagtccg gatcgtagtc tgcaactcga ctacgtgaag tcggaatcgc tagtaatcgc  1320
agatcagcat gctgcggtga atacgttccc gggtcttgta cacaccgccc gtcacaccat  1380
gggagtgggt tcaccagaa gtaggtagct aaccttcgg gagggcgct                1429

<210> SEQ ID NO 34
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 34
tggctcagat tgaacgctgg cggcatgctt tacacatgca agtcgaacgg cagcgggggc     60
```

```
ttcggcctgc cggcgagtgg cgaacgggtg agtaatgcat cggaacgtgc ccatgtcgtg    120
ggggataacg tatcgaaagg tacgctaata ccgcatacgc cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggtgg aattcctggt     660 gtagcagtga aatgcgtaaa gatcaggagg aacaccgatg gcgaaggcag cccctgggc      720 ctgtactgac gctcatgcac gaaagcgtgg ggagcaaaca ggattagata ccctggtagt    780
ccacgcccta aacgatgtcg actagtcgtt cggagcagca atgcactgag tgacgcagct    840
aacgcgtgaa gtcgaccgcc tggggagtac ggccgcaagg ttaaaactca aaggaattga    900
cggggacccg cacaagcggt ggatgatgtg gattaatttg atgcaacgcg aaaaacctta    960
cctacccttg acatgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgct    1439
```

<210> SEQ ID NO 35
<211> LENGTH: 1440
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 35

```
tggctcagat tgaacgctgg cggcatgctt tacacatgca agtcgaacgg cagcggggc     60 ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggtgg aattcctggt     660
```

-continued

```
gtagcagtga aatgcgtaga gatcaggagg aacaccgatg gcgaaggcag ccccctgggc    720
ctgtactgac gctcatgcac gaaagcctgg gggagcaaca ggattagata ccctggtaag    780
tccacgccct aaacgatgtc gactagtcgt tcggagcagc aatgcactga gtgacgcagc    840
taacgcgtga agtcgaccgc ctggggagta cggccgcaag gttaaaactc aaaggaattg    900
acggggaccc gcacaagcgg tggatgatgt ggattaattc gatgcaacgc gaaaaacctt    960
acctacccct gacatgccag gaaccttgcc gagaggcgag ggtgccttcg ggagcctgga   1020
cacaggtgct gcatggctgt cgtcagctcg tgtcgtgaaa tgttgggtta agtcccgcaa   1080
cgagcgcaac ccttgtcact agttgccatc atttggttgg gcactctagt gagactgccg   1140
gtgacaaacc ggaggaaggt ggggatgacg tcaagtcctc atggccctta tgggtagggc   1200
ttcacacgtc atacaatggt cggtacagag ggttgccaag ccgcgaggtg gagccaatcc   1260
cttaaagccg atcgtagtcc ggatcgtagt ctgcaactcg actacgtgaa gtcggaatcg   1320
ctagtaatcg cagatcagca tgctgcggtg aatacgttcc cgggtcttgt acacaccgcc   1380
cgtcacacca tgggagtggg tttcaccaga gtaggtagc ttaaccttcg ggagggcgct   1440
```

```
<210> SEQ ID NO 36
<211> LENGTH: 1440
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 36
```

```
tggctcagat tgaacgctgg cggcatgctt tacacatgca agtcgaacgg cagcggggc     60 ttcggcctgc cggcgagtgg cgaacgggtg agtaatgcat cggaacgtgc ccatgtcgtg   120
ggggataacg tatcgaaagg tacgctaata ccgcatacgt cctgagggag aaagcggggg   180
atcttcggac ctcgcgcgat tggagcggcc gatgtcggat tagctagtag gtgaggtaaa   240
ggctcaccta ggcgacgatc cgtagcgggt ctgagaggat gatccgccac actgggactg   300
agacacggcc cagactccta cgggaggcag cagtggggaa ttttggacaa tgggcgcaag   360
cctgatccag ccatgccgcg tgagtgaaga aggccttcgg gttgtaaagt tctttcggcc   420
gggaagaaat cgtggtctct aacataggcc atggatgacg gtaccggact aagaagcacc   480
ggctaactac gtgccagcag ccgcggtaat acgtagggtg cgagcgttaa tcggaattac   540
tgggcgtaaa gcgtgcgcag gcggttttgt aagacagatg tgaaatcccc gggctcaacc   600
tgggaactgc gtttgtgact gcaaggctag agtacggcag aagggggtgg aattcctggt   660
gtagcagtga aatgcgtaga gatcaggagg aacaccgatg gcgaaggcag ccccctttggg   720 cctgtactga cgctcatgca cgaaagcgtg gggagcaaac aggattagat accctggtag   780
tccacgccct aaacgatgtc gactagtcgt tcggagcagc aatgcactga gtgacgcagc    840
taacgcgtga agtcgaccgc ctggggagta cggccgcaag gttaaaactc aaaggaattg    900
acggggaccc gcacaagcgg tggatgatgt ggattaattc gatgcaacgc gaaaaacctt    960
acctacccct gacatgccag gaaccttgcc gagaggcgag ggtgccttcg ggagcctgga   1020
cacaggtgct gcatggctgt cgtcagctcg tgtcgtgaga tgttgggtta agtcccgcaa   1080
cgagcgcaac ccttgtcact agttgccatc atttggttgg gcactctagt gagactgccg   1140
gtgacaaacc ggaggaaggt ggggatgacg tcaagtcctc atggccctta tgggtagggc   1200
ttcacacgtc atacaatggt cggtacagag ggttgccaag ccgcgaggtg gagccaatcc   1260
```

```
cttaaagccg atcgtagtcc ggatcgtagt ctgcaactcg actacgtgaa gtcggaatcg    1320
ctagtaatcg cagatcagca tgccgcggtg aatacgttcc cgggtcttgt acacaccgcc    1380
cgtcacacca tgggagtggg tttcaccaga agtaggtagc ttaaccttcg ggagggcgct    1440
```

<210> SEQ ID NO 37
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 37

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg ttgtaaagc tctttcggcc     420 gggaagaaat cgtggtctct aacataggcc atggatgacg gtaccggact aagaagcacc     480
ggctaactac gtgccagcag ccgcggtaat acgtagggtg cgagcgttaa tcggaattac     540
tgggcgtaaa gcgtgcgcag gcggttttgt aagacagatg tgaaatcccc gggctcaacc     600
tgggaactgc gtttgtgact gcaaggctag agtacggcag agggggtgg aattcctggt      660 gtagcagtga aatgcgtaga gatcaagagg aacaccgatg gcgaaggcag ccccctgggc     720
ctgtactgac gttcatgcac gaaagcgtgg ggagcaaaca ggattagata ccctggtagt     780
ccacgcccta aacgatgtcg actagtcgtt cggagcagca atgcactgag tgacgcagct     840
aacgcgtgaa gtcgaccgcc tggggagtac ggccgcaagg ttaaaactca aaggaattga     900
cggggacccg cacaagcggt ggatgatgtg gattaattcg atgcaacgcg aaaaacctta     960
cctacccttg acatgccagg aaccttgccg agaggcgagg gtgccttcgg agcctggac     1020 acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgct    1439
```

<210> SEQ ID NO 38
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 38

```
tggctcagat tgaacgctgg cggcatgctt tacacatgca agtcgaacgg cagcgggggc      60
```

```
ttcggcctgc cggcgagtgg cgaacgggtg agtaatgcat cggaacgtgc ccatgtcgtg      120
ggggataacg tatcgaaagg tacgctaata ccgcatacgt cctgagggag agagcggggg      180
atcttcggac ctcgcgcgat tggagcggcc gatgtcggat tagctagtag gtgaggtaaa      240
ggctcaccta ggcgacgatc cgtagcgggt ctgagaggat gatccgccac actgggactg      300
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacgcag aggggggtgg aattcctggt       660
gtagcagtga aatgcgtaga gatcaggagg aacaccgatg ggaaggcag cccctgggc        720 ctgtactgac gctcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aaggaattga      900
cggggacccg cacaagcggt ggatgatgtg gattaattcg atgcaacgcg aaaaacctta      960
cctacccttg acatgccagg aaccttgccg agaggcgagg gtgccttcgg gagcctggac     1020
acaggtgctg catggctgtc gtcagctcgt gtcgtgagat gttgggttaa gtcccgcaac     1080
gagcgcaacc cttgtcacta gttgccatca tttggttggg cactctagtg agactgccgg     1140
tgacaaaccg gaggaaggtg gggatgacgt caagtcctca tggcccttat gggtagggct     1200
tcacacgtca tacaatggtc ggtacagagg gttgccaagc cgcgaggtgg agccaatccc     1260
ttaaagccga tcgtagtccg gatcgtagtc tgcaactcga ctacgtgaag tcggaatcgc     1320
tagtaatcgc agatcagcat gctgcggtga atacgttccc gggtcttgta cacaccgccc     1380
gtcacaccat gggagtgggt ttcaccagaa gtaggtagct taaccttcgg gagggcgct     1439
```

<210> SEQ ID NO 39
<211> LENGTH: 1439
<212> TYPE: DNA
<213> ORGANISM: unknown
<220> FEATURE:
<223> OTHER INFORMATION: Unknown clone from enriched environmental sample that by rDNA sequence analysis has highest identity to Thauera aromatica

<400> SEQUENCE: 39

```
tggctcagat tgaacgctgg cggcatgctt tacacatgca agtcgaacgg cagcggggc       60 ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttgtaaagc tctttcggcc     420
gggaagaaat cgtggtctct aacataggcc atggatgacg gtaccggact aagaagcacc     480
ggctaactac gtgccagcag ccgcggtaat acgtagggtg cgagcgttaa tcggaattac     540
tgggcgtaaa gcgtgcgcag gcggttttgt aagacagatg tgaaatcccc gggctcaacc     600
tgggaactgc gtttgtgact gcaaggctag agtacggcag aggggggtgg aattcctggt     660
```

```
gtatcagtga aatgcgtaaa gatcaagagg aacaccgatg gggaaggcag ccccctgggc      720
ctgtactgac gttcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aggaattga       900 cggggacccg cacaagcggt ggatgatgtg gattaattcg atgcaacgcg aaaaacctta      960 cctaccttg acatgccagg aaccttgccg agaggcgagg gtgccttcgg agcctggac       1020 acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgt agatcagcat gctgcggtga atacgttccc gggtcttgta cacaccgccc    1380
gtcacaccat gggagtgggt tcaccagaa gtaggtagct taaccttcgg gagggcgct     1439
```

<210> SEQ ID NO 40
<211> LENGTH: 1439
<212> TYPE: DNA
<213> ORGANISM: unknown
<220> FEATURE:
<223> OTHER INFORMATION: Unknown clone from enriched environmental
sample that by rDNA sequence analysis has highest identity to
Thauera aromatica

<400> SEQUENCE: 40

```
tggctcagat tgaacgctgg cggcatgctt tacacatgca agtcgaacgg cagcggggc      60 ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag aggggggtgg aactcctggt    660
gtagcagtga aatgcgtaga gatcaggagg aacaccgatg gcgaaggcag ccccctgggc    720
ttgtactgac gctcatgcac gaaagcgtgg ggagcaaaca ggattagata ccctggtagt    780
ccacgcccta aacgatgtcg actagtcgtt cggagcagca atgcactgag tgacgcagct    840
aacgcgtgaa gtcgaccgcc tggggagtac ggccgcaagg ttaaaactca aggaattga     900 cggggacccg cacaagcggt ggatgatgtg gattaattcg atgcaacgcg aaaaacctta    960 cctaccttg acatgccagg aaccttgccg agaggcgagg gtgccttcgg agcctggac     1020 acaggtgctg catggctgtc gtcagctcgt gtcgtgagat gttgggttaa gtcccgcaac   1080
gagcgcaacc cttgtcacta gttgccatca tttggttggg cactctagtg agactgccgg   1140
tgacaaaccg gaggaaggtg gggatgacgt caagtcctca tggcccttat gggtagggct   1200
tcacacgtca tacaatggtc ggtacagagg gttgccaagc cgcgaggtgg agccaatccc   1260
```

```
ttaaagccga tcgtagtccg gatcgtagtc tgcaactcga ctacgtgaag tcggaatcgc   1320
tagtaatcgc agatcagcat gctgcggtga atacgttccc gggtcttgta cacaccgccc   1380
gtcacaccat gggagtgggt ttcaccagaa gtaggtagct taaccttcgg gagggcgct    1439
```

<210> SEQ ID NO 41
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 41

```
tggctcagat tgaacgctgg cggcatgctt tacacatgca agtcgaacgg cagcggggc    60 ttcggcctgc cggcgagtgg cgaacgggtg agtaatgcat cggaacgtgc ccatgtcgtg  120
ggggataacg tatcgaaagg tacgctaata ccgcatacgt cctgagggag aaagcggggg  180
atcttcggac ctcgcgcgat tggagcggcc gatgtcggat tagctagtag gtgaggtaaa  240
ggctcaccta ggcgacgatc cgtagcgggt ctgagaggat gatccgccac actgggactg  300
agacacggcc cagactccta cgggaggcag cagtggggaa ttttggacaa tgggcgcaag  360
cctgatccag ccatgccgcg tgagtgaaga aggccttcgg gttgtaaagc tctttcggcc  420
gggaagaaat cgtggtctct aacataggcc atggatgacg gtaccggact aagaagcacc  480
ggctaactac gtgccagcag ccgcggtaat acgtagggtg cgagcgttaa tcggaattac  540
tgggcgtaaa gcgtgcgcag gcggttttgt aagacagatg tgaaatcccc gggctcaacc  600
tgggaactgc gtttgtgact gcaaggctag agtacggcag agggggtgg aattcctggt   660 gtagcagtga aatgcgtaga tcaggagg aacgccgatg gcgaagacag cccctgggc     720 ctgtactgac gctcatgcac gaaagcgtgg ggagcaaaca ggattagata ccctggtagt  780
ccacgcccta aacgatgtcg actagtcgtt cggagcagca atgcactgag tgacgcagct  840
aacgcgtgaa gtcgaccgcc tggggagtac ggccgcaagg ttaaaactca aaggaattga  900
cggggacccg cacaagcggt ggatgatgtg gattaattcg atgcaacgcg aaaaacctta  960 cctaccccttg acatgccagg aaccttgccg agaggcgagg gtgccttcgg agcctggac  1020 acaggtgctg catggctgtc gtcagctcgt gtcgtgagat gttgggttaa gtcccgcaac  1080
gagcgcaacc cttgtcacta gttgccatca tttggttggg cactctagtg agactgccgg  1140
tgacaaaccg gaggaaggtg gggatgacgt caagtcctca tggcccttat gggtagggct  1200
tcacacgtca tacaatggtc ggtacagggg gttgccaagc cgcgaggtgg agccaatccc  1260
ttaaagccga tcgtagtccg gatcgtagtc tgcaactcga ctacgtgaag tcggaatcgc  1320
tagtaatcgc agatcagcat gctgcggtga atacgttccc gggtcttgta cacaccgccc  1380
gtcacaccat gggagtgggt ttcaccagaa gtaggtagct taaccttcgg gagggcgct   1439
```

<210> SEQ ID NO 42
<211> LENGTH: 1475
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 42

```
tggctcagga cgaacgctgg cggcgtgcct aacacatgca agtcgagcga agtgactctg   60
```

```
agagaaattt tcggatggat cgaagagtca tcttagcggc ggacgggtga gtaacgcgtg      120
agaaacctgc ctttcacaaa gggatagcct cgggaaactg ggattaatac cttatgaaac      180
tgaattaccg catggtagat cagtcaaagc gaataagcgg tgaaagatgg tctcgcgtcc      240
tattagctag ttggtgaggt aacggctcac caaggcttcg ataggtagcc ggcctgagag      300
ggtgaacggc cacactggaa ctgagacacg gtccagactc ctacgggagg cagcagtggg      360
gaatattgca caatggagga aactctgatg cagcgacgcc gcgtgaatga tgaaggcctt      420 cggggttgtaa agttctgtcc ttggggaaga taatgacggt acccaaggag gaagccccgg     480
ctaactacgt gccagcagcc gcggtaatac gtaggggggcg agcgttgtcc ggaattattg      540
ggcgtaaagg gttcgcaggc ggtctgataa gtcagatgtg aaaggcgtag gctcaaccta      600
cgtaagcatt tgaaactgtc agacttgagt taaggagagg aaagtggaat tcctagtgta      660
gcggtgaaat gcgtagatat taggaggaat accagtggcg aagggsgact ttctggactt      720
atactgacgc tgaggaacga aagcgtgggg agsaaacagg attagatacc ctggtagttc      780
cacgccgtaa acgawgagtg ctaggtgktg ggggtcaaac ctcggtgccg caasctaacg      840
cattaagcac tccgcctggg gggtacgtac gcmagtatga aactcaaagg aattgacggg      900
gacccgcaca agcggtggat gatgtggatt aattcgatgc aacgcgaaaa accttaccta      960
cccttgacat gccaggaacc ttgccgagag gcgaggtgc cttcgggagc ctggacacag      1020
gtgctgcatg gctgtcgtca gctcgtgtcg tgagatgttg ggttaagtcc cgcaacgagc     1080
gcaacccttg tcactagttg ccatcatttg gttgggcact ctagtgagac tgccggtgac     1140
aaaccggagg aaggtgggga tgacgtcaag tcctcatggc ccttatgggt agggcttcac     1200
acgtcataca atggtcggta cagagggttg ccaagccgcg aggtggagcc aatcccttaa     1260
agccgatcgt agtccggatc gtagtctgca actcgactac gtgaagtcgg aatcgctagt     1320
aatcgcagat cagcatgctg cggtgaatac gttcccgggt cttgtacaca ccgcccgtca     1380
caccatggga gtgggtttca ccagaagtag gtagcttaac cttcgggaac cacggtgaga     1440
ttcatgactg gggtgaagtc gtaacaaggt aaccg                                1475
```

<210> SEQ ID NO 43
<211> LENGTH: 1481
<212> TYPE: DNA
<213> ORGANISM: unknown
<220> FEATURE:
<223> OTHER INFORMATION: Unknown clone from enriched environmental
      sample that by rDNA sequence analysis has highest identity to
      Spirochaeta sp. MET-E

<400> SEQUENCE: 43

```
tggctcagaa cgaacgctgg cggcgcgttt taagcatgca agtcgagcgg caagggcctt       60
tgggccccta gagcggcgga cggtgagta acacgtggac aatctgcccc ccggccgggg      120
atagcccagg gaaacctgga ttaataccgg atgagacggg acgcacgatg gtgcggtccg      180
ggaaaggcgc tgccggcgccg ccggggggatg agtccgcgac ccattagctg gacggcgggg      240
taaaggccca ccgtggcgac gatgggtagc cggcctgaga gggtggacgg ccacattgga      300
actgagacac ggtccagact cctacgggag gcagcagcta agaatcttcc gcaatgggcg      360
aaagcctgac ggagcgacgc cgcgtgaacg aagaaggccg tgaggttgta agttctttt       420 cgggaggggg aattaccgtg gcagggaatg ccgcgggat gacgtgaatc ccggaacaag       480
ccccggctaa ctacgtgcca gcagccgcgg taacacgtag ggggcgagcg ttgttcggaa      540
tcattgggcg taaagggcgt gcaggcggca ctgcaagtcc ggcgtgaaag acccggccc      600
```

```
aaccgggggg gtgcgctgga aactgcggtg cttgagtaca ggaggggatg ccggaattcc      660
aggtgtaggg gtgaaatctg tagatatctg gaagaacacc gatggcgaag gcaggcatct      720
ggccatgtac tgacgctgag acgcgaaggt gcggggagca acaggttta gatacccctgg     780 tagtccgcac agtaaacgat gtgcaccagg gtggcggggg tagaaccccc ggtaccgtag      840
caaacgcatt aagtgcaccg cctggggagt atgctcgcaa gggtgaaact caaaggaatt      900
gacgggggcc cgcacaagcg gaggagcatg tggtttaatt cgatgatacg cgaggaacct      960
tacctgggct cgaacgtaag atgactgtag gtgaaagctt acatctcttc ggagcatttt      1020
acgaggtgct gcatggttgt cgtcagctcg tgccgtgagg tgtcgggtta agtcccataa      1080
cgagcgcaac ccctaccttt agttgccatc aggtaatgct gggactcta aaggaactgc      1140 ctacgcaagt agtgaggaag gcggggatga cgtcaaatca gcacggccct tacgtccagg      1200
gctacacacg tgctacaatg gccgatacag agggcagcta cctggtgaca ggatgcaaat      1260
ctccaaagtc ggtctcagtt cggatcggag tctgcaaccc gactccgtga agttggattc      1320
gctagtaatc gcgcatcagc catggcgcgg tgaatacgtt cccgggcctt gtacacaccg      1380
cccgtcaagc catggaagct ggggggacct aaagtcgata accgcaagga gtcgcctagg      1440
gtaaaaccag tgactggggc taagtcgtaa caaggtaacc g                          1481
```

<210> SEQ ID NO 44
<211> LENGTH: 1488
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 44

```
tggctcagat tgaacgctgg cggcaggcct aacacatgca agtcgagcgg atgagtggag       60
cttgctccat gattcagcgg cggacgggtg agtaatgcct aggaatctgc ctggtagtgg      120
gggacaacgt ttcgaaagga acgctaatac cgcatacgtc ctacgggaga agtgggggga      180
tcttcggacc tcacgctatc agatgagcct aggtcggatt agctagttgg cgaggtaaag      240
gctcaccaag gcgacgatcc gtaactggtc tgagaggatg atcagtcaca ctggaactga      300
gacacggtcc agactcctac gggaggcagc agtggggaat attggacaat gggcgaaagc      360
ctgatccagc catgccgcgt gtgtgaagaa ggccttcggg ttgtaaagct ctttcggccg      420
ggaagaaatc gtggtctcta acataggcca tgatgacgg taccggacta agaagcaccg      480
gctaactacg tgccagcagc cgcggtaata cgtagggtgc gagcgttaat cggaattact      540
gggcgtaaag cgtgcgcagg cggttttgta agacagatgt gaaatccccg ggctcaacct      600
gggaactgcg tttgtgactg caaggctaga gtacggcaga gggggtgga attcctggtg      660 tagcagtgaa atgcgtagag atcaggagga acaccgatgg cgaaggcagc ccctgggcc      720 tgtactgacg ctcatgcacg aaagcgtggg gagcaaacag gattagatac cctggtagtc     780
cacgccctaa acgatgtcga ctagtcgttc ggagcagcaa tgcactgagt gacgcagcta      840
acgcgtgaag tcgaccgcct ggggagtacg gccgcaaggt taaaactcaa aggaattgac      900
ggggacccgc acaagcggtg gatgatgtgg attaattcga tgcaacgcga aaaaccttac      960
ctacccttga catgccagga accttgccga gaggcgaggg tgccttcggg agcctggaca     1020
caggtgctga atggctgtcg tcagctcgtg tcgtgagatg ttgggttaag tcccgcaacg     1080
agcgcaaccc ttgtcactag ttgccatcat ttggttgggc actctagtga gactgccggt     1140
```

```
gacaaaccgg aggaaggtgg ggatgacgtc aagtcctcat ggcccttatg ggtagggctt    1200
cacacgtcat acaatggtcg gtacagaggg ttgccaagcc gcgaggtgga gccaatccct    1260
taaagccgat cgtagtccgg atcgtagtct gcaactcgac tacgtgaagt cggaatcgct    1320
agtaatcgca gatcagcatg ctgcggtgaa tacgttcccg ggccttgtac acaccgcccg    1380
tcacaccatg agagttggca atacccgaag tccgtgggc aaccgtttac ggagccagcg     1440
gccgaaggta gggtcagcga ttggggtgaa gtcgtaacaa ggtaaccg                 1488
```

<210> SEQ ID NO 45
<211> LENGTH: 1481
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 45

```
cggttacctt gttacgactt caccccagtc attgccccta ccttcgacag ctgccccctt      60
ttatggttag ctcactggct tcgggtattg acaactccca tggtgtgacg ggcggtgtgt    120
acaagacccg ggaacgcatt caccgcggca ttctgatccg cgattactag caactccgac    180
ttcatgcagg cgagttgcag cctgcaatcc gaactgggat cggcttttag agatttgctt    240
gccatcgctg acttgcttct cgttgtaccg accattgtag cacgtgtgta gcccaggaca    300
taaagggcat gatgatttga cgtcatcccc accttcctcc gatttgtcat cggcagtctc    360
tttagagtgc ccaacttaat gatggcaact aaagacaagg gttgcgctcg ttgcgggact    420
taacccaaca tctcacgaca cgagctgacg acaaccatgc accacctgtg tccgctgtac    480
cccgaaggat aaagatctat ctctaaaccg gtcagcggca tgtcaagccc tggtaaggtt    540
cttcgcgttg cttcgaatta aaccacatgc tccgctgctt gtgcgggtcc ccgtcaattc    600
ctttgagttt catacttgcg tacgtactcc ccaggcggag tgcttaatgc gttagctgcg    660
gcaccgaggt ttgaccccca acacctagca ctcatcgttt acggcgtgga ctaccagggt    720
atctaatcct gtttgctccc cacgctttcg ttcctcagcg tcagtataag tccagaaagt    780
cgccttcgcc actggtattc ctcctaatat ctacgcattt caccgctaca ctaggaattc    840
cactttcctc tccttaactc aagtctgaca gtttcaaatg cttacgtagg ttgagcctac    900
gcctttcaca tctgacttat cagaccgcct gcgaacccct tacgcccaat aattccggac    960
aacgctcgcc ccctacgtat taccgcggct gctggcacgt agttagccgg ggcttcctcc   1020
ttgggtaccg tcattatctt ccccaaggac agaactttac aacccgaagg ccttcatcat   1080
tcacgcggcg tcgctgcatc agagtttcct ccattgtgca atattcccca ctgctgcctc   1140
ccgtaggagt ctggaccgtg tctcagttcc agtgtggccg ttcaccctct caggccggct   1200
acctatcgaa gccttggtga gccgttacct caccaactag ctaataggac gcgagaccat   1260
ctttcaccgc ttattcgctt tgactgatct accatgcggt aattcagttt cataaggtat   1320
taatcccagt ttcccgaggc tatcccttttg tgaaaggcag gtttctcacg cgttactcac   1380
ccgtccgccg ctaagatgac tcttcgatcc atccgaaaay ttctctcmga gtcacttcgc   1440
ggcacgccgc cagcgttcgt cctgagccak aatcaaactc t                       1481
```

<210> SEQ ID NO 46
<211> LENGTH: 1486
<212> TYPE: DNA
<213> ORGANISM: unknown

<220> FEATURE:
<223> OTHER INFORMATION: Unknown clone from enriched environmental
     sample that by rDNA sequence analysis has highest identity to
     Azotobacter beijerinckii

<400> SEQUENCE: 46

| tggctcagat tgaacgctgg cggcaggcct aacacatgca agtcgagcgg atgagtggag | 60 |
| cttgctccat gattcagcgg cggacgggtg agtaatgcct aggaatctgc ctggtagtgg | 120 |
| gggacaacgt ttcgaaagga acgctaatac cgcatacgtc ctacgggaga aagtggggga | 180 |
| tcttcggacc tcacgctatc agatgagcct aggtcggatt agctagttgg tgaggtaaag | 240 |
| gctcaccaag gcgacgatcc gtaactggtc tgagaggatg atcagtcaca ctggaactga | 300 |
| gacacggtcc agactcctac gggaggcagc agtggggaat attggacaat gggcgaaagc | 360 |
| ctgatccagc catgccgcgt gtgtgaagaa ggtcttcgga ttgtaaagca ctttaagttg | 420 |
| ggaggaaggg cagtaagtta ataccttgct gttttgacgt taccgacaga ataagcaccg | 480 |
| gctaacttcg tgccagcagc cgcggtaata cgaagggtgc aagcgttaat cggaattact | 540 |
| gggcgtaaag cgcgcgtagg tggttcgtta agttggatgt gaaagccccg ggctcaacct | 600 |
| gggaactgca tccaaaactg gcgagctaga gtatggcaga tggtggtgga atttcctgtg | 660 |
| tagcggtgaa atgcgtacat ataggaagga acaccagtgg cgaaggcgac cacctgggct | 720 |
| aatactgaca ctgaggtgcg aaagcgtggg agcaaacag gattagatac cctggtagtc | 780 |
| cacgccctaa acgatgtcga ctagtcgttc ggagcagcaa tgcactgagt gacgcagcta | 840 |
| acgcgtgaag tcgaccgcct ggggagtacg gccgcaaggt taaaactcaa aggaattgac | 900 |
| ggggacccgc acaagcggtg gatgatgtgg attaattcga tgcaacgcga aaaaccttac | 960 |
| ctacccttga catgccagga accttgccga gaggcgaggg tgccttcggg agcctggaca | 1020 |
| caggtgctgc atggctgtcg tcagctcgtg tcgtgagatg ttgggttaag tcccgcaacg | 1080 |
| agcgcaaccc ttgtcactag ttgccatcat ttggttgggc actctagtga gactgccggt | 1140 |
| gacaaaccgg aggaaggtgg ggatgacgtc aagtcctcat ggcccttatg ggtagggctt | 1200 |
| cacacgtcat acaatggtcg gtacagaggg ttgccaagcc gcgaggtgga gccaatccct | 1260 |
| taaagccgat cgtagtccgg atcgtagtct gcaactcgac tacgtgaagt cggaatcgct | 1320 |
| agtaatcgca gatcagcatg ctgcggtgaa tacgttcccg ggtcttgtac acaccgcccg | 1380 |
| tcacaccatg ggagtgggtt tcaccagaag taggtagctt aaccttcggg agggcgctta | 1440 |
| ccacggtgag attcatgact ggggtgaagt cgtaacaagg taaccg | 1486 |

<210> SEQ ID NO 47
<211> LENGTH: 1442
<212> TYPE: DNA
<213> ORGANISM: unknown
<220> FEATURE:
<223> OTHER INFORMATION: Unknown clone from enriched environmental
     sample that by rDNA sequence analysis has highest identity to
     Ochrobactrum sp. mp-5

<400> SEQUENCE: 47

| tggctcagaa cgaacgctgg cggcaggctt aacacatgca agtcgagcgc cccgcaaggg | 60 |
| gagcggcaga cgggtgagta acgcgtggga acgtaccttt tgctacggaa taactcaggg | 120 |
| aaacttgtgc taataccgta tgtgcccttc ggggaaaga tttatcggca aaggatcggc | 180 |
| ccgcgttgga ttagctagtt ggtgaggtaa aggctcacca aggcgacgat ccatagctgg | 240 |
| tctgagagga tgatcagcca cactgggact gagacacggc ccagactcct acggaggca | 300 |
| gcagtgggga atattggaca atgggcgcaa gcctgatcca gccatgccgc gtgagtgatg | 360 |

```
aaggccctag ggttgtaaag ctctttcacc ggtgaagata atgacggtaa ccggagaaga      420
agccccggct aacttcgtgc cagcagccgc ggtratacga aggggggctag cgttgttcgg     480 atttactggg cgtaaagcgc acgtaggcgg acttttaagt caggggtgaa atcccggggc     540 tcaayccogg aactgccttt gatactggaa gtcttgagta tggtagaggt gagtggaatt     600
ccgagtgtag aggtgaaatt cgtagatatt cggaggaaca ccagtggcga aggcggctca     660
ctggaccatt actgacgctg aggtgcgaaa gcgtggggag caaacaggat tagataccct    720
ggtagtccac gccgtaaacg atgaatgtta gccgttgggg agtttactct cggtggcgc     780 agctaacgca ttaaacattc cgcctgggga gtacggtcgc aagattaaaa ctcaaaggaa    840
ttgacggggg cccgcacaag cggtggagca tgtggtttaa ttygaagcaa cgcgcagaac     900
cttaccagcc cttgacatac cggtcgcgga cacagagatg tgtctttcag ttcggctgga    960
ccggatacag gtgctgcatg gctgtcgtca gctcgtgtcg tgagatgttg ggttaagtcc   1020
cgcaacgagc gcaaccctcg cccttagttg ccagcattta gttgggcact ctaagggac    1080 tgccggtgat aagccgagag gaaggtgggg atgacgtcaa gtcctcatgg cccttacggg   1140
ctgggctaca cacgtgctac aatggtggtg acagtgggca gcgagcacgc gagtgtgagc   1200
taatctccaa aagccatctc agttcggatt gcactctgca actcgagtgc atgaagttgg   1260
aatcgctagt aatcgcggat cagcatgccg cggtgaatac gttcccgggc cttgtacaca   1320
ccgcccgtca caccatggga gttggtttta cccgaaggcg ctgtgctaac gcaaggagg    1380 caggcgacca cggtagggtc agcgactggg gtgaagtcgt aacaaggtaa ccgaagggcg   1440
at                                                                  1442
```

<210> SEQ ID NO 48
<211> LENGTH: 1478
<212> TYPE: DNA
<213> ORGANISM: unknown
<220> FEATURE:
<223> OTHER INFORMATION: Unknown clone from enriched environmental
      sample that by rDNA sequence analysis has highest identity to
      Anaeurovorax sp/EH8A

<400> SEQUENCE: 48

```
tggctcagga tgaacgctgg cggcgtgcct aacacatgca agtcgagcgg tatatagtgg     60
aatgaaactt cggtcgagtg aagctataga gagcggcgga cgggtgagta acgcgtaggc   120
aacctgcccc atacagaggg atagcctcgg gaaaccggga ttaaaacctc ataacgcgag    180
gagttcacat ggactgctcg ccaaagattc atcggtatgg gatgggcctg cgtctgatta    240
gctagttggt gaggtaacgg ctcaccaagg cgacgatcag tatccgacct gagagggtaa   300
tcggccacat tggaactgag acacagtcca aactcctaca ggaggcagca gtggggaata    360
ttgcacaatg ggcgaaagcc tgatgcaaca acgccgcgtg agcgatgaac gcctttgggt   420
cgtaaagctc tgtccttggg gaagaaacaa atgacggtac ccttggaaga agccccggct    480
aactacgtgc cagcagccgc ggtaatacgt agggggcgag cgttatccgg aattattggg    540
cgtaaagagt gcgtacgtgg ctatgtaagc gcgaggtgaa aggcaatagc ttaactattg   600
taagccttgc gaactgtgtg gcttgggtgc aggacaggaa agtggaattc ctattgtagc    660
ggtgaaatgc gtagatatta ggaggaacac cactggcgaa ggcgactttc tggactgtaa    720
ctgacactga ggcacgaaag cgtggggagc aaacaggatt agataccctg gtagtccacg    780
ccgtaaacga tgagcactag gtgtaggggt cgcaagactt cggtgccgca gttaacgcat    840
taagtgctcc gcctggggag tacgcacgca agtgtgaaac tcaaaggaat tgacggggac    900
```

```
ccgcacaagc agcggagcat gtggtttaat tcgaagcaac gcgaagaacc ttatcagggc   960
ttgacatccg tatgacagtc cgttaaccgg gacgttcttc ggacagagga gacaggtggt  1020
gcatggttgt cgtcagctcg tgtcgtgaga tgttgggtta agtcccgcaa cgagcgcaac  1080
ccttgtcttt agttgccatc atttggttgg gcactctagt gagactgccg gtgacaaacc  1140
ggaggaaggt ggggatgacg tcaagtcctc atggccctta tgggtagggc ttcacacgtc  1200
atacaatggt cggtacagag ggttgccaag ccgcgaggtg gagccaatcc cttaaagccg  1260
atcgtagtcc ggatcgtagt ctgcaactcg actacgtgaa gtcggaatcg ctagtaatcg  1320
cagatcagca tgctgcggtg aatacgttcc cgggtcttgt acacaccgcc cgtcacacca  1380
tgggagtggg tttcaccaga agtaggtagc ttaaccttcg ggagggcgct taccacggtg  1440
agattcatga ctggggtgaa gtcgtaacaa ggtaaccg                           1478
```

<210> SEQ ID NO 49
<211> LENGTH: 883
<212> TYPE: DNA
<213> ORGANISM: unknown
<220> FEATURE:
<223> OTHER INFORMATION: Unknown clone from enriched environmental
      sample that by rDNA sequence analysis has highest identity to
      Anaerovorax sp. EH8A

<400> SEQUENCE: 49

```
tggctcagga tgaacgctgg cggcgtgcct aacacatgca agtcgagcgg tatatagtgg    60
aacgaaactt cggtcgagtg aagccataga gagcggcgga cggtgagta acgcgtaggc   120
aacctgcccc atacagaggg atagcctcgg gaaaccggga ttaaaacctc ataacgcgag   180
gagttcacat ggacttctcg ccaaagattc atcggtatgg gatgggcctg cgtctgatta   240
gctagttggt gaggtaacgg ctcaccaagg cgacgatcag tagccgacct gagagggtaa   300
tcggccacat tggaactgag acacggtcca aactcctacg ggaggcagca gtggggaata   360
ttgcacaatg ggcgaaagcc tgatgcagca acgccgcgtg agcgatgaag gcctttgggt   420
cgtaaagctc tgtccttggg gaagaaacaa atgacggtac ccttggagga agccccggct   480
aactacgtgc cagcagccgc ggtaatacgt aggggggcgag cgttatccgg aattattggg   540
cgtaaagagt gcgtaggtgg ccatgtaagc gcggggtgaa aggcaatagc ttaactattg   600
taagccttgc gaactgtgtg gcttgagtgc aggagaggaa agtggaattc ctagtgtagc   660
ggtgaaatgc gtagatatta ggaggaacac cagtggcgaa ggcgactttc tggactgtaa   720
ctgacactga ggcacgaaag cgtggggagc aaacaggatt agataccctg gtagtccacg   780
ccgtaaacga tgagcactag gtgtcggggt cgcaagactt cggtgccgca gttaacgcat   840
taagtgctcc gcctggggag tacgcacgca agtgtgaaac tca                    883
```

<210> SEQ ID NO 50
<211> LENGTH: 521
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 50

```
acatgccact gaccgcatca gagatggtgc tttaccttcg ggtacagtgg acacaggtgg    60
tgcatggttg tcgtcagctc gtgtcgtgag atgttgggtt aagtcccgca acgagcgcaa   120
cccctgtttc tagttgccag cattaagttg ggcactctag agagactgcc gatgacaaat   180
```

| | |
|---|---|
| cggaggaagg tggggatgac gtcaaatcat catgccctttt atgccctggg ctacacacgt | 240 |
| gctacaatgg tcggtacaac gaggagcaaa ccagcgatgg caagcaaatc tctaaaagcc | 300 |
| gatcccagtt cggattgcag gctgcaactc gcctgcatga agtcggagtt gctagtaatc | 360 |
| gcggatcaga atgtcgcggt gaatgcgttc ccgggtcttg tacacaccgc ccgtcacacc | 420 |
| atgggagttg tcaatacccg aagccagtga gctaaccagt aatggaggca gctgtcgaag | 480 |
| gtagggcga tgactggggt gaagtcgtaa caaggtaacc g | 521 |

<210> SEQ ID NO 51
<211> LENGTH: 888
<212> TYPE: DNA
<213> ORGANISM: unknown
<220> FEATURE:
<223> OTHER INFORMATION: Unknown clone from enriched environmental
sample that by rDNA sequence analysis has highest identity to
Finegoldia magna

<400> SEQUENCE: 51

| | |
|---|---|
| tacgtaagca tttgaaactg tcagacttga gttaaggaga ggaaagtgga attcctagtg | 60 |
| tagcggtgaa atgcgtagat attaggagga ataccagtgg cgaaggcgac tttctggact | 120 |
| tatactgacg ctgaggaacg aaagcgtggg gagcaaacag gattagatac cctggtagtc | 180 |
| cacgccgtaa acgatgagtg ctaggtgttg ggggtcaaac ctcggtgccg cagctaacgc | 240 |
| attaagcact ccgcctgggg agtacgtacg caagtatgaa actcaaagga attgacgggg | 300 |
| acccgcacaa gcagcggagc atgtggttta attcgaagca acgcgaagaa ccttaccagg | 360 |
| gcttgacatg ccgctgaccg gtgcagagat gcatctttat ccttcggggt acagcggaca | 420 |
| caggtggtgc atggttgtcg tcagctcgtg tcgtgagatg ttgggttaag tcccgcaacg | 480 |
| agcgcaaccc ttgtctttag ttgccatcat taagttgggc actctaaaga gactgccgat | 540 |
| gacaaatcgg aggaaggtgg ggatgacgtc aaatcatcat gccctttatg tcctgggcta | 600 |
| cacacgtgct acaatggtcg gtacaacgag aagcaagtca gcgatggcaa gcaaatctct | 660 |
| aaaagccgat cccagttcgg attgcaggct gcaactcgcc tgcatgaagt cggagttgct | 720 |
| agtaatcgcg gatcagaatg ccgcggtgaa tgcgttcccg ggtcttgtac acaccgcccg | 780 |
| tcacaccatg ggagttgtca atacccgaag ccagtgagct aaccataaaa ggaggcagct | 840 |
| gtcgaaggta ggggcaatga ctggggtgaa gtcgtaacaa ggtaaccg | 888 |

<210> SEQ ID NO 52
<211> LENGTH: 888
<212> TYPE: DNA
<213> ORGANISM: unknown
<220> FEATURE:
<223> OTHER INFORMATION: Unknown clone from enriched environmental
sample that by rDNA sequence analysis has highest identity to
Finegoldia magna

<400> SEQUENCE: 52

| | |
|---|---|
| tacgtaagca tttgaaactg tcagacttga gttaaggaga ggaaagtgga attcctagtg | 60 |
| tagcggtgaa atgcgtagat attaggagga ataccagtgg cgaaggcgac tttctggact | 120 |
| tatactgacg cggaggaacg aaagcgtggg gagcaaacag gattagatac cctggtagtc | 180 |
| cacgccgtaa acgatgagtg ctaggtgttg ggggtcaaac ctcggtgccg cagctaacgc | 240 |
| attaagcact ccgcctgggg agtacgtacg caagtatgaa actcaaagga attgacgggg | 300 |
| acccgcacaa gcagcggagc atgtggttta attcgaagca acgcgaagaa ccttaccagg | 360 |
| gcttgacatg ccgctgaccg gtttagagat agatctttac ccttcggggt acagcggaca | 420 |

```
caggtggtgc atggttgtcg tcagctcgtg tcgtgagatg ttgggttaag tcccgcaacg    480
agcgcaaccc ttgtctttag ttgccatcat taagttgggc actctaaaga gactgccgat    540
gacaaatcgg aggaaggtgg ggatgacgtc aaatcatcat gccctttatg tcctgggcta    600
cacacgtgct acaatggtcg gtacaacgag aagcaagtca gcgatggcaa gcaaatctct    660
aaaagccgat cccagttcgg attgcaggct gcaactcgcc tgcatggagt cggagttgct    720
agtaatcgcg gatcagaatg ccgcggtgaa tgcgttcccg ggtcttgtac acaccgcccg    780
tcacaccatg ggagttgtca atacccgaag ccagtgagct aaccataaaa gggggcagct    840
gtcgaaggta ggggcaatga ctggggtgaa gtcgtaacaa ggtaaccg                 888
```

<210> SEQ ID NO 53
<211> LENGTH: 1502
<212> TYPE: DNA
<213> ORGANISM: unknown
<220> FEATURE:
<223> OTHER INFORMATION: Unknown clone from enriched environmental
       sample that by rDNA sequence analysis has highest identity to
       Flexistipes sp. vp180

<400> SEQUENCE: 53

```
tggctcagaa cgaacgctgg cggcgtgctt aacacatgca agtcaaggag aaagtctctt     60
cggaggcgag taaactggcg cacgggtgag taacgcgtga ggaacctgcc catatgtctg    120
ggataacctg ctgaaaagcg ggctaatact ggatatattg tttaccgcat ggtgaacaag    180
gaaagttggt gcaagctaac gcatatggat ggtctcgcgt ctgattagct agttggtggg    240
gtaaaggctc accaaggcga cgatcagtag ccggtctgag agggtggccg gccacactgg    300
gactgagaca cggcccagac tcctacggga ggcagcagtg gggaattttg cacaatgggg    360
gcaaccctga tgcagcgacg ccgcgtgaac gaggaaggcc ttcgggtcgt aaagttcttt    420
cgacggggaa gaaatgttat acgagtaact gcgtataatt tgacggtacc tgtagaagca    480
gccccggcta actccgtgcc agcagccgcg gtaatacgga gggggcgagc gttgttcgga    540
gttactgggc gtaaagcgca cgtaggcggt gcggtaagtc aggggttaaa ggtcacagct    600
caactgtgat aaggcctttg atactatcgt gctagagtgt cagagagggt agcggaattc    660
ccggtgtagc ggtgaaatgc gtatatatcg ggaggaacac cagtggcgaa gggcggctac    720
ctggctgata actgacgctg aggtgcgaga gcgtggggag caaacaggat tagataccct    780
ggtagtccac gctgtaaacg atggacgtta ggtgttgggg gaaccgaccc cctcagtgcc    840
gaagctaacg cgttaaacgt cccgcctggg gagtacggcc gcaaggttga aactcaaagg    900
aattgacggg ggcccgcaca agcggtggag cacgtggttt aattcgatgc taaccgaaga    960
accttacctg ggtttgacat ccctcgaatc ctgtagagat atgggagtgc ctggcttgcc   1020
aggagcgagg agacaggtgc tgcatggctg tcgtcagctc gtgccgtgag gtgttgggtt   1080
aagtcccgca acgagcgcaa cccctatttt tagttgccat cacgttaagg tgggcactct   1140
aaagagaccg ccggggataa cccggaggaa ggtgggggatg acgtcaagtc atcatggccc   1200
ttatgtccag ggctacacac gtgctacaat ggtgcataca gagggcagcg agacagcgat   1260
gttaagcgaa tcccttaaag tgtacctcag ttcggattgc agtctgcaac tcgactgtat   1320 gaagccgaa tcgctagtaa tcgcaggtca gcaaaactgc ggtgaatacg ttcccggcc   1380 ttgtacacac cgcccgtcac accacgggag tcggttgtac ctgaagccgg tggcccaacc   1440
gcaagggggg agccgtctat ggtatggctg gtaactgggg tgaagtcgta acaaggtaac   1500
cg                                                                 1502
```

<210> SEQ ID NO 54
<211> LENGTH: 1499
<212> TYPE: DNA
<213> ORGANISM: unknown
<220> FEATURE:
<223> OTHER INFORMATION: Unknown clone from enriched environmental
sample that by rDNA sequence analysis has highest identity to
Azoarcus sp. EH11

<400> SEQUENCE: 54

```
agagtttgat tatggctcag attgaacgct ggcggcatgc tttacacatg caagtcgaac     60
ggcagcgggg gcttcggcct gccggcgagt ggcgaacggg tgagtaatgc atcggaacgt    120
gcccatgtcg tgggggataa cgtatcgaaa ggtacgctaa taccgcatac gtcctgaggg    180
agaaagcggg ggatcttcgg acctcgcgcg attggagcgg ccgatgtcgg attagctagt    240
aggtgaggta aaggctcacc taggcgacga tccgtagcgg gtctgagagg atgatccgcc    300
acactgggac tgagacacgg cccagactcc tacgggagga gcagtggggg aattttggac    360
aatgggcgca agcctgatcc agccatgccg cgtgagtgaa gaaggccttc gggttgtaaa    420
gctctttcgg ccgggaagaa atcgtggtct ctaacatagg ccatgatga cggtaccgga    480
ctaagaagca ccggctaact acgtgccagc agccgcggta atacgtaggg tgcgagcgtt    540
aatcggaatt actgggcgta aagcgtgcgc aggcggtttt gtaagacaga tgtgaaatcc    600
ccgggctcaa cctgggaact gcgtttgtga ctgcaaggct agagtacggc agagggggt    660
ggaattcctg gtgtagcagt gaaatgcgta gagatcagga ggaacaccga tggcgaaggc    720
agccccctgg gcctgtactg acgctcatgc acgaaagcgt ggggagcaaa caggattaga    780
taccctggta gtccacgccg taaacgatga gtgctaggtg ttgggggtca aacctcggtg    840
ccgcagctaa cgcattaagc actccgcctg gggagtacgt acgcaagtat gaaactcaaa    900
ggaattgacg gggacccgca caagcagcgg agcatgtggt ttaattcgaa gcaacgcgaa    960
gaaccttacc agggcttgac atgccgctga ccggtttaga gatagacctt tatccttcgg   1020
ggtacagcgg acacaggtgg tgcatggttg tcgtcagctc gtgtcgtgag atgttgggtt   1080
aagtcccgca acgagcgcaa cccttgtcac tagttgccag catttagttg ggcactctgg   1140
tgagactgcc ggtgacaaac cggaggaagg tggggatgac gtcaagtcct catgcccctt   1200
atgggtaggg cttcacacgt catacaatgg tcggtacaga gggttgccaa gccgcgaggt   1260
ggagccaatc ccttaaagcc gaccgtagtc cggatcgtag tctgcaactc gactacgtga   1320
agtcggaatc gctagtaatc gcagatcagc atgctgcggt gaatacgttc ccgggtcttg   1380
tacacaccgc ccgtcacacc atgggagtgg gtttcaccag aagtaggtag cttaaccttc   1440
gggagggcgc ttaccacggt gagattcatg actggggtga agtcgtaaca aggtaaccg   1499
```

<210> SEQ ID NO 55
<211> LENGTH: 1475
<212> TYPE: DNA
<213> ORGANISM: unknown
<220> FEATURE:
<223> OTHER INFORMATION: Unknown clone from enriched environmental
sample that by rDNA sequence analysis has highest identity to
Clostridium chartatabidium

<400> SEQUENCE: 55

```
tggctcagga cgaacgctgg cggcgtgcct aacacatgca agtcgagcgg agaatgcaga     60
aatgtttaca tggaagtatt cttagcgcg gacgggtgag taacacgtgg gtaacctgcc    120
tcaaagtggg ggatagcctt ccgaaaggaa gattaatacc gcataagcct acagtgccgc    180
```

```
atggcacagc aggaaaagga gcaatccgct ttgagatgga cccgcggcgc attagctagt      240
tggtgaggta acggctcacc aaggcgacga tgcgtagccg acctgagagg gtgatcggcc      300
acattggaac tgagacacgg tccagactcc tacgggaggc agcagtgggg aatattgcac      360
aatgggcgaa agcctgatgc agcaacgccg cgtgagtgat gaaggccttc gggtcgtaaa      420
gctctttgat cagggatgat aatgacagta cctgaaaaac aagccacggc taactacgtg      480
ccagcagccg cggtaatacg taggtggcga gcgttgtccg gaattactgg gcgtaaagga      540
tgcgtaggtg gatacttaag tgggatgtga atccccggg ctcaacccgg gaactgcatt       600
ccaaactggg tatctagagt gcaggagagg aaagcggaat tcctagtgta gcggtgaaat      660
gcgtagagat caggaggaac accgatggcg aaggcagccc cctgggcctg tactgacgct      720
catgcacgaa agcgtgggga gcaaacaggg atagataccc tggtagtcca cgccctaaac      780
gatgtcgaat aagtcgttcc gaccagcaat gcactgagtg acgcagctaa cgcgtgaagt      840
cgaccgcctg gggagtacgg ccgcaaggtt aaaactcaaa ggaattgacg ggacccgca      900 caagcggtgg atgatgtgga ttaattcgat gcaacgcgaa aaaccttacc tacccttgac      960
atgccaggaa ccttgccgag aggcgagggt gccttcggga gcctggacac aggtgctgca     1020
tggctgtcgt cagctcgtgt cgtgagatgt tgggttaagt cccgcaacga gcgcaaccct     1080
tgtcactagt tgccatcatt tggttgggca ctctagtgag actgccggtg acaaaccgga     1140
ggaaggtggg gatgacgtca agtcctcatg gcccttatgg gtagggcttc acacgtcata     1200
caatggtcga tacagagggt tgccaagccg cgaggtggag ccaatccctt aaagccgatc     1260
gtagtccgga tcgtagtctg caactcgact acgtgaagtc ggaatcgcta gtaatcgcag     1320
atcagcatgc tgcggtgaat acgttccgg gtcttgtaca caccgcccgt cacaccatgg      1380
gagtgggctt caccagaagt aggtagctta accttcggga gggcgcttac cacggtgaga     1440
ttcatgactg gggtgaagtc gtaacaaggt aaccg                                1475
```

<210> SEQ ID NO 56
<211> LENGTH: 1492
<212> TYPE: DNA
<213> ORGANISM: unknown
<220> FEATURE:
<223> OTHER INFORMATION: Unknown clone from enriched environmental sample that by rDNA sequence analysis has highest identity to Deferribacter desulfuricans

<400> SEQUENCE: 56

```
tggctcagaa cgaacgctgg cggcgtgctt aacacatgca agtcaaggag aaagtctctt       60
cggaggcgag taaactggcg cacgggtgag taacgcgtga ggaacctgcc catatgtctg      120
ggataacctg ctgaaaagcg ggctaatact ggatatattg tttaccgcat ggtgaacaag      180
gaaagttggt gcaagctaac gcatatggat ggtctcgcgt ctgattagct agttggtggg      240
gtaaaggctc accaaggcaa cgatcagtag ccggtctgag agggtggccg gccacactgg      300
gactgagaca cggcccagac tcctacggga ggcagcagtg ggaattttg cacaatgggg       360 gcaaccctga tgcagcgacg ccgcgtgaac gaggaaggcc ttcgggtcgt aaagttcttt      420
cgacggggaa gaaatgttat acgagtaact gcgtataatt tgacggtacc cgtagaagca      480
gccccggcta actccgtgcc agcagccgcg gtaatacgga gggggcgagc gttgttcgga      540
gttactgggc gtaaagcgca cgtacgcggt gcggtaagtc aggggttaaa ggtcacagct      600
caactgtgat aaggcctttg atactatcgt gctagagtgt cagagagggt agcggaattc      660
ccggtgtagc ggtgaaatgc gtagatatcg gaggaacaca cagtagcgaa ggcggctacc      720
```

```
tggctgataa ctgacgctga ggtgcgagag cgtggggagc aaacaggatt agataccctg     780
gtagtccacg ccctaaacga tgtcgactag tcgttcggag cagcaatgca ctgagtgacg     840
cagctaacgc gtgaagtcga ccgcctgggg agtacggccg caaggttaaa actcaaagga     900
attgacgggg acccgcacaa gcggtggatg atgtggatta attcgatgca acgcgaaaaa     960
ccttacctac ccttgacatg ccaggaacct tgccgagagg cgagggtgcc ttcgggagcc    1020
tggacacagg tgctgcatgg ctgtcgtcag ctcgtgtcgt gagatgttgg gttaagtccc    1080
gcaacgagcg caaccttgt cactagttgc catcatttgg ttgggcactc tagtgagact    1140
gccggtgaca accggagga aggtggggat gacgtcaagt cctcatggcc cttatgggta    1200
gggcttcaca cgtcatacaa tggtcggtac agagggttgc caagccgcga ggtggagcca    1260
atcccttaaa gccgatcgta gtccggatcg tagtctgcaa ctcgactacg tgaagtcgga    1320
atcgctagta atcgcagatc agcatgctgc ggtgaatacg ttcccgggtc ttgtacacac    1380
cgcccgtcac accatgggag tgggtttcac cagaagtagg tagcttaacc ttcgggaggg    1440
cgcttaccac ggtgagattc atgactgggg tgaagtcgta acaaggtaac cg             1492

<210> SEQ ID NO 57
<211> LENGTH: 1519
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 57
tggctcagaa cgaacgctgg cggcgtgctt aacacatgca agtcaagggg aaagtctctt      60
cggaggcgag taaactggcg cacgggtgag taacgcgtga ggaacctgcc catatgtctg     120
ggataacctg ctgaaaagcg ggctaatact ggatatattg tttaccgcat ggtgaacaag     180
gaaagttggt gcaagctaac gcatatggat ggtctcgcgt ctgattagct agttggtggg     240
gtaaaggctc accaaggcaa cgatccgtag cgggtctgag aggatggtcc gccacactgg     300
gactgagaca cggcccagac tcctacggga ggcagcagtg gggaattttg acaatgggc     360 gcaagcctga tccagccatg ccgcgtgagt gaagaaggcc ttcgggttgt aaagctcttt     420
cggccgggaa gaaatcgtgg tctctaacat aggccatgga tgacggtacc ggactaagaa     480
gcaccggcta actacgtgcc agcagccgcg gtaatacgta gggtgcgagc gttaatcgga     540
attactgggc gtaaagcgtg cgcaggcggt tttgtaagac agatgtgaaa tccccgggct     600
caacctggga actgcgtttg tgactgcaag gctagagtac ggcagagggg ggtggaattc     660
ctggtgtagc agtgaaatgc gtagagatca ggaggaacac cgatggcgaa ggcagccccc     720
tgggcctgta ctgacgctca tgcacgaaag cgtggggagc aaacaggatt agataccctg     780
gtagtccacg ccctaaacga tgtcgactag tcgttcggag cagcaatgca ctgagtgacg     840
cagctaacgc gtgaagtcga ccgcctgggg agtacggccg caaggttaaa actcaaagga     900
attgacgggg acccgcacaa gcggtggatg atgtggatta attcgatgca acgcgaaaaa     960
ccttacctac ccttgacatg ccaggaacct tgccgagagg cgagggtgcc ttcgggagcc    1020
tggacacagg tgctgcatgg ctgtcgtcag ctcgtgtcgt gagatgttgg gttaagtccc    1080
gcaacgagcg caaccttgt cactagttgc catcatttgg ttgggcactc tagtgagact    1140
gccggtgaca accggagga aggtggggat gacgtcaagt cctcatggcc cttatgggta    1200
gggcttcaca cgtcatacaa tggtcggtac agagggttgc caagccgcga ggtggagcca    1260
```

```
atcccttaaa gccgatcgta gtccggatcg tagtctgcaa ctcgactacg tgaagtcgga    1320
atcgctagta atcgcagatc agcatgctgc ggtaaatacg ttcccgggtc ttgtacacac    1380
cgcccgtcac accatgggag tgggtttcac cagaagtagg tagcttaacc ttcgggaggg    1440
cgcttaccac ggtgagattc atgactgggg tgaagtcgta acaaggtaac cgaagggcga    1500
atcaatcgcc tatgactgg                                                 1519

<210> SEQ ID NO 58
<211> LENGTH: 373
<212> TYPE: DNA
<213> ORGANISM: unknown
<220> FEATURE:
<223> OTHER INFORMATION: Unknown clone from enriched environmental
      sample that by rDNA sequence analysis has highest identity to
      Flexistipes sp. vp180

<400> SEQUENCE: 58
tggctcagaa cgaacgctgg cggcgtgctt aacacatgca agtcaaggag aaaatctctt     60
cgggggcgag taaactggcg cacgggtgag taacgcgtga ggaacctgcc catatgtctg    120
ggataacctg ctgaaaagcg ggctaatact ggatatattg tttaccgcat ggtggacaag    180
gaaagttggt gtaagctaac gcatatggat ggtctcgcgt ctgattagct agttggtggg    240
gtaaaggctc accaaggcga cgatcagtag ccggtctgag agggtggccg gccacactgg    300
gactgagaca cggcccatac tcctacggga ggcagcagtg gggaattttg cacaatgggg    360
gcaaccctga tgc                                                       373

<210> SEQ ID NO 59
<211> LENGTH: 1431
<212> TYPE: DNA
<213> ORGANISM: unknown
<220> FEATURE:
<223> OTHER INFORMATION: Unknown clone from enriched environmental
      sample that by rDNA sequence analysis has highest identity to
      Ochrobactrum lupini

<400> SEQUENCE: 59
tggctcagaa cgaacgctgg cggcaggctt aacacatgca agtcgagcgc cccgcaagga     60
gagcggcaga cgggtgagta acgcgtggga acgtaccttt tgctacggaa taactcaggg    120
aaacttgtgc taataccgta tgtgcccttc gggggaaaga tttatcggca aaggatcggc    180
ccgcgttgga ttagctagtt ggtgaggtaa aggctcacca aggcgacgat ccatagctgg    240
tctgagagga tgatcagcca cactgggact gagacacggc ccagactcct acgggaggca    300
gcagtgggga atattggaca atgggcgcaa gcctgatcca gccatgccgc gtgagtgatg    360
aaggccctag ggttgtaaag ctctttcacc ggtgaagata atgacggtaa ccggagaaga    420
agccccggct aacttcgtgc cagcagccgc ggtaatacga aggggctag cgttgttcgg    480 atttactggg cgtaaagcgc acgtaggcgg acttttaagt caggggtgaa atcccggggc    540
tcaaccccgg aactgccttt gatactgaa gtcttgagta tggtagaggt gagtggaatt    600
ccgagtgtag aggtgaaatt cgtagatatt cggaggaaca ccagtggcga aggcggctca    660
ctggaccatt actgacgctg aggtgcgaaa gcgtggggag caaacaggat tagataccct    720
ggtagtccac gccgtaaacg atgaatgtta gccgttgggg agtttactct tcggtggcgc    780
agctaacgca ttaaacattc cgcctgggga gtacggtcgc aagattaaaa ctcaaaggaa    840
ttgacgggga cccgcacaag cggtggatga tgtggattaa ttcgatgcaa cgcgaaaaac    900
cttacctacc cttgacatgc caggaacctt gccgagaggc gagggtgcct tcgggagcct    960
```

```
ggacacaggt gctgcatggc tgtcgtcagc tcgtgtcgtg agatgttggg ttaagtcccg    1020
caacgagcgc aacccttgcc actagttgcc atcatttggt tgggcactct agtgagactg    1080
ccggtgacaa accggaggaa ggtggggatg acgtcaagtc ctcatggccc ttatgggtag    1140
ggcttcacac gtcatacaat ggtcggtaca gagggttgcc aagccgcgag gtggagccaa    1200
tcccttaaag ccgatcgtag tccggatcgt agtctgcaac tcgactacgt gaagtcggaa    1260
tcgctagtaa tcgcagatca gcatgctgcg gtgaatrcgt tcccgggtct tgtacacacc    1320
gcccgtcaca ccatgggagt gggtttcacc agaagtaggg agcttaacct tcgggagggc    1380
acttaccacg gtgagattca tgactggggt gaagtcgtaa caaggtaacc g             1431

<210> SEQ ID NO 60
<211> LENGTH: 1454
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas pseudoalcligenes

<400> SEQUENCE: 60
tggctcagat tgaacgctgg cggcaggcct aacacatgca agtcgagcgg atgagtggag      60
cttgctccat gattcagcgg cggacgggtg agtaatgcct aggaatctgc ctggtagtgg     120
gggacaacgt ttcgaaagga acgctaatac cgcatacgtc ctacgggaga aagtggggga    180
tcttcggacc tcacgctatc agatgagcct aggtcggatt agctagttgg cgaggtaaag    240
gctcaccaag gcgacgatcc gtaactggtc tgagaggatg atcagtcaca ctggaactga    300
gacacggtcc agactcctac gggaggcagc agtggggaat attggacaat gggcgaaagc    360
ctgatccagc catgccgcgt gtgtgaagaa ggtcttcgga ttgtaaagca ctttaagttg    420
ggaggaaggg cagtaagtta taccttgct gttttgacgt taccgacaga ataagcaccg     480
gctaacttcg tgccagcagc cgcggtaata cgaagggtgc aagcgttaat cggaattact    540
gggcgtaaag cgcgcgtagg tggttcgtta agttggatgt gaaagccccg ggctcaacct    600
gggaactgca tccaaaactg gcgagctaag ttatggcaga ggggggtgga aatttcctgt    660
gtagcggtga aatgggtaga tataggaagg aacaccagtg gcgaaggcga ccacctgggc    720
taatactgac actgaggtgc gaaagcgtgg ggagcaaaca ggattagata ccctggtagt    780
ccacgccgta aacgatgtcg actagccgtt gggatccttg agatcttagt ggcgcagcta    840
acgcattaag tcgaccgcct ggggagtacg gccgcaaggt taaaactcaa atgaattgac    900
gggggcccgc acaagcggtg gagcatgtgg tttaattcga agcaacgcga agaaccttac    960
caggccttga catgctgaga acctgccaga gatggcgggg tgccttcggg aactcagaca   1020
caggtgctgc atggctgtcg tcagctcgtg tcgtgagatg ttgggttaag tcccgtaacg   1080
agcgcaaccc ttgtccttag ttaccagcac gttatggtgg gcactctaag gagactgccg   1140
gtgacaaacc ggaggaaggt ggggatgacg tcaagtcatc atggccctta cggcctgggc   1200
tacacacgtg ctacaatggt cggtacaaag ggttgccaag ccgcgaggtg gagctaatcc   1260
cataaaaccg atcgtagtcc ggatcgcagt ctgcaactcg actgcgtgaa gtcggaatcg   1320
ctagtaatcg tgaatcagaa tgtcacggtg aatacgttcc cgggccttgt acacaccgcc   1380
cgtcacacca tgggagtggg ttgctccaga agtagctagt ctaaccttcg ggggacggt    1440 taccacggag tgat                                                    1454
```

```
<210> SEQ ID NO 61
<211> LENGTH: 854
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas purida

<400> SEQUENCE: 61
tgggaactgc atccaaaact ggcgagctag agtatggcag agggtggtgg aatttcctgt      60
gtagcggtga aatgcgtaga tataggaagg aacaccagtg gcgaaggcga ccacctgggc     120
taatactgac actgaggtgc gaaagcgtgg agagcaaaca ggattagata ccctggtagt     180
ccacgccgta aacgatgtcg actagccgtt gggatccttg agatcttagt ggcgcagcta     240
acgcattaag tcgaccgcct ggggagtacg gccgcaaggt taaaactcaa atgaattgac     300
gggggcccgc acaagcggtg gagcatgtgg tttaattcga agcaacgcga agaaccttac     360
caggccttga catgcagaga actttccaga gatggattgg tgccttcggg agctctgaca     420
caggtgctgc atggctgtcg tcagctcgtg tcgtgagatg ttgggttaag tcccgtaacg     480
agcgcaaccc ttgtccttag ttaccagcac gttaaggtgg gcactctaag gagactgccg     540
gtgacaaacc ggaggaaggt ggggatgacg tcaagtcatc atggccctta cggcctgggc     600
tacacacgtg ctacaatggt cggtacaaag ggttgccaag ccgcgaggtg gagctaatcc     660
cataaaaccg atcgtagtcc ggatcgcagt ctgcaactcg actgcgtgaa gtcggaatcg     720
ctagtaatcg tgaatcagaa tgtcacggtg aatacgttcc cgggccttgt acacaccgcc     780
cgtcacacca tgggagtggg ttgctccaga agtagctagt ctaaccttcg gggggacggt     840
taccacggag tgat                                                       854

<210> SEQ ID NO 62
<211> LENGTH: 854
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas pseudoalcligenes

<400> SEQUENCE: 62
tgggaactgc atccaaaact ggcgagctag agtatggcag agggtggtgg aatttcctgt      60
gtagcggtga aatgcgtaga tataggaagg aacaccagtg gcgaaggcga ccacctgggc     120
taatactgac actgaggtgc gaaagcgtgg agagcaaaca ggattagata ccctggtagt     180
ccacgccgta aacgatgtcg actagccgtt gggatccttg agatcttagt ggcgcagcta     240
acgcattaag tcgaccgcct ggggagtacg gccgcaaggt taaaactcaa atgaattgac     300
gggggcccgc acaagcggtg gagcatgtgg tttaattcga agcaacgcga agaaccttac     360
caggccttga catgcagaga actttccaga gatggattgg tgccttcggg agctctgaca     420
caggtgctgc atggctgtcg tcagctcgtg tcgtgagatg ttgggttaag tcccgtaacg     480
agcgcaaccc ttgtccttag ttaccagcac gttaaggtgg gcactctaag gagactgccg     540
gtgacaaacc ggaggaaggt ggggatgacg tcaagtcatc atggccctta cggcctgggc     600
tacacacgtg ctacaatggt cggtacaaag ggttgccaag ccgcgaggtg gagctaatcc     660
cataaaaccg atcgtagtcc ggatcgcagt ctgcaactcg actgcgtgaa gtcggaatcg     720
ctagtaatcg tgaatcagaa tgtcacggtg aatacgttcc cgggccttgt acacaccgcc     780
cgtcacacca tgggagtggg ttgctccaga agtagctagt ctaaccttcg ggggacggt      840
```

```
taccacggag tgat                                                  854

<210> SEQ ID NO 63
<211> LENGTH: 1448
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium chartatabidium

<400> SEQUENCE: 63
tggctcagga cgaacgctgg cggcgtgcct aacacatgca agtcgagcgg agaatgcaga     60
aatgtttaca tggaagcgtt cttagcggcg gacgggtgag taacacgtgg gtaacctgcc    120
tcaaagtggg ggatagcctt ccgaaaggaa gattaatacc gcataagcct acagtgccgc    180
atggcacagc aggaaaagga gcaatccgct ttgagatgga cccgcggcgc attagctagt    240
tggtgaggta acggctcacc aaggcgacga tgcgtagccg acctgagagg gtgatcggcc    300
acattggaac tgagacacgg tccagactcc tacgggaggc agcagtgggg aatattgcac    360
aatgggcgaa agcctgatgc agcaacgccg cgtgagtgat gaaggccttc gggtcgtaaa    420
gctctttgat cagggatgat aatgacagta cctgaaaaac aagccacggc taactacgtg    480
ccagcagccg cggtaatacg taggtggcga cgttgtccg gaattactgg gcgtaaagga    540
tgcgtaggtg gatacttaag tgggatgtga atccccggg ctcaacccgg gaactgcatt    600
ccaaactggg tatctagagt gcaggagagg aaagcgaat tcctagtgta gcggtgaaat    660
gcgtagatat taggaggaac accagtggcg aaggcggctt tctggactgt aactgacact    720
gaggcatgaa agcgtgggta gcaaacagga ttagatacc ctggtagtcca cgccgtaaac    780 gatgggtact aggtgtagga ggtatcgacc ccttctgtgc cgtcgttaac acaataagta    840
ccccgcctgg ggagtacggt cgcaagacta aaactcaaag gaattgacgg gggcccgcac    900
aagcagcgga gcatgtggtt taattcgaag caacgcgaag aaccttacct agacttgaca    960
tctcctgaat tacccttaac cggggaagcc cttcggggca ggaagacagg tggtgcatgg   1020
ttgtcgtcag ctcgtgtcgt gagatgttgg gttaagtccc gcaacgagcg caacccttat   1080
ttttagttgc taccatttgg ttgagcactc taaagagact gcccgggtta accgggagga   1140
aggtggggat gacgtcaaat catcatgccc cttatgtcta gggctacaca cgtgctacaa   1200
tggtgagaac aaagagacgc gagaccgcga ggtggagcaa atctcataaa actcatccca   1260
gttcggattg caggctgaaa ctcgcctgca tgaagccgga gttgctagta atcgcgaatc   1320
agcatgtcgc ggtgaatacg ttcccgggcc ttgtacacac cgcccgtcac accatgagag   1380
ttggcaatac ccgaagtccg tggggcaacc agttaatgga gccagcggcc gaaggtaggg   1440
tcagcgat                                                           1448

<210> SEQ ID NO 64
<211> LENGTH: 1486
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 64
tggctcagga cgaacgctgg cggcgtgcct aacacatgca agtcgagcga agtgactcgg     60
agagaagttt tcgaatggat cgaagagtca tcttagcggc ggacgggtga gtaacgcgtg    120
```

```
agaaacctgc ctttcacaaa gggatagcct cgggaaactg ggattaatac cttatgaaac      180
tgaattaccg catggtagat cagtcaaagc gaataagcgg tgaaagatgg tctcgcgtcc      240
tattagctag ttggtgaggt aacggctcac caaggcttcg ataggtagcc ggcctgagag      300
ggtgaacggc cacactggaa ctgagacacg gtccagactc ctacgggagg cagcagtggg      360
gaatattgca caatggagga aactctgatg cagcgacgcc gcgtgaatga tgaaggcctt      420
cgggttgtaa agttctgtcc ttggggaaga taatgacggt acccaaggag gaagcccgg      480 ctaactacgt gccagcagcc gcggtaatac gtaggggggcg agcgttgtcc ggaattattg      540
ggcgtaaagg gttcgcaggc ggtctgataa gtcagatgtg aaaggcgtag gctcaaccta      600
cgtaagcatt tgaaactgtc agacttgagt taaggagagg aaagtggaat tcctagtgta      660
gcggtgaaat gcgtagatat aagaggaat accagtggcg aaggcgactt tctggactta      720
tactgacgct taggaacgaa agcgtgggga gcaaacagga ttagataccc tggtagtcca      780
cgccgtaaac gatgagtgct aggtgttggg ggtcaaacct cggtgccgca gctaacgcat      840
taagcactcc gcctggggag tacgtacgca agtatgaaac tcaaaggaat tgacggggac      900
ccgcacaagc agcggagcat gtggtttaat tcgaagcaac gcgaagaacc ttaccagggc      960
ttgacatgcc gctgaccggt ttagagatag acctttatcc ttcggggtac agcggacaca      1020
ggtggtgcat ggttgtcgtc agctcgtgtc gtgagatgtt gggttaagtc ccgcaacgag      1080
cgcaacccct tgtctttagtt gccatcatta agttgggcac tctaaagaga ctgccgatga      1140
caaatcggag gaaggtgggg gtgacgtcaa atcatcatgc cctttatgtc ctgggctaca      1200
cacgtgctac aatggtcggt acaacgagaa gcaagccagc gatggcaagc aaatctctaa      1260
aagccgatcc cagttcggat tgcaggctgc aactcgcctg catgaagtcg agttgctag      1320 taatcgcgga tcagaatgcc gcggtgaatg cgttcccggg tcttgtacac accgcccgtc      1380
acaccatggg agttgtcaat acccgaagcc agtgagctaa ccataaaagg gggcagctgt      1440
cgaaggtagg ggcaatgact ggggtgaagt cgtaacaagg taaccg                     1486
```

<210> SEQ ID NO 65
<211> LENGTH: 881
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 65

```
tggctcagga cgaacgctgg cggcgtgcct aacacatgca agtcgagcga agtgactcgg       60
agagaaattt tcggatggat cgaagagtca tcttagcggc ggacgggtga gtaacgcgtg      120
agaaacctgc ctttcacaaa gggatagcct cgggaaactg ggattaatac cttatgaaac      180
tgaattaccg catggtagat cagtcaaagc gaataagcgg tgaaagatgg tctcgcgtcc      240
tattagctag ttggtgaggt aacggctcac caaggcttcg ataggtagcc ggcctgagag      300
ggtgaacggc cacactggaa ctgagacacg gtccagactc ctacgggagg cagcagtggg      360
gaatattgca caatggagga aactctgatg cagcgacgcc gcgtgaatga tgaaggcctt      420
cgggttgtaa agttctgtcc ttggggaaga taatgacggt acccaaggag gaagcccgg      480 ctaactacgt gccagcagcc gcggtaatac gtaggggggcg agcgttgtcc ggaattattg      540
ggcgtaaagg gttcgcaggc ggtctgataa gtcagatgtg aaaggcgtag gctcaaccta      600
cgtaagcatt tgaaactgtc agacttgagt taaggagagg aaagtggaat tcctagtgta      660
```

-continued

```
gcggtgaaat gcgtagatat taggaggaat accagtggcg aaggcgactt tctggactta    720
tactgacgct gaggaacgaa agcgtgggga gcaaacagga ttagataccc tggtagtcca    780
cgccgtaaac gatgagtgct aggtgttggg ggtcaaacct cggtgccgca gctaacgcat    840
taagcactcc gcctggggag tacgtacgca agtatgaaac t    881
```

<210> SEQ ID NO 66
<211> LENGTH: 1393
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 66

```
tggctcagga cgaacgctgg cggcgtgcct aacacatgca agtcgagcga agtgactctg     60
agagaaattt tcggatggat cgaagagtca tcttagcggc ggacgggtga gtaacgcgtg    120
agaaacctgc ctttcacaaa gggatagcct cgggaaactg ggattaatac cttatgaaac    180
tgaattaccg catggtagat cagtcaaagc gaataagcgg tgaaagatgg tctcgcgtcc    240
tattagctag ttggtgaggt aacggctcac caaggcttcg ataggtagcc ggcctgagag    300
ggtgaacggc cacactggaa ctgagacacg gtccagactc ctacgggagg cagcagtggg    360
gaatattgca caatggagga aactctgatg cagcgacgcc gcgtgaatga tgaaggcctt    420
cgggttgtaa agttctgtcc ttggggaaga taatgacggt acccaaggag gaagccccgg    480
ctaactacgt gccagcagcc gcggtaatac gtagggggcg agcgttgtcc ggaattattg    540
ggcgtaaagg gttcgcaggc ggtctgataa gtcagatgtg aaaggcgtag gctcaaccta    600
cgtaagcatt tgaaactgtc agacttgagt taaggagagg aaagtggaat tcctagtgta    660
gcggtgaaat gcgcagatat taggaggaat accagtggcg aaggcgactt tctggactta    720
tactgacgct gaggaacgaa agcgtgggga gcaaacagga ttagataccc tggtagtcca    780
cgccgtaaac gatgagtgct aggtgttggg ggtcaaacct cggtgccgca gctaacgcat    840
taagcactcc gcctggggag tacgtacgca agtatgaaac tcaaaggaat tgacggggac    900
ccgcacaagc agcggagcat gtggtttaat tcgaagcaac gcgaagaacc ttaccagggc    960
ttgacatgcc gctgaccggt ttagagatag atctttatcc ttcggggtac ggcggacaca   1020
ggtggtgcat ggttgtcgtc agctcgtgtc gtgagatgtt gggttaagtc ccgcaacgag   1080
cgcaacccct gtctttagtt gccatcatta agttgggcac tctaaagaga ctgccgatga   1140
caaatcggag gaaggtgggg atgacgtcaa atcatcatgc cctttatgtc ctgggctaca   1200
cacgtgctac aatggtcggt acaacgagaa gcaagtcagc gatggcaagc aaatctctaa   1260
aagccgatcc cagttcggat tgcaggctgc aactcgcctg catgaagtcg gagttgctag   1320
taatcgcgga tcagaatgcc gcggtgaatg cgttcccggg tcttgtacac accgcccgtc   1380
acaccatggg agt    1393
```

<210> SEQ ID NO 67
<211> LENGTH: 1440
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t

<400> SEQUENCE: 67

```
tggctcagat tgaacgctgg cggcatgctt tacacatgca agtcgaacgg cagcggggc      60
ttcggcctgc cggcgagtgg cgaacgggtg agtaatgcat cggaacgtgc ccatgtcgtg    120
ggggataacg tatcgaaagg tacgctaata ccgcatacgt cctgagggag aaagtggggg    180
atcttcggac ctcacgctat cagatgagcc taggtcggat tagctagttg gcgaggtaaa    240
ggctcaccaa ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag aagggggtgg aattcctggt    660
gtancantga aatgcgtaaa gatcaagagg aacaccgatg gcgaaagcag ccccctgggc    720
ctgtactgac cctcatgcac gaaagcgtgg ggagcaaaca agattaaata ccctggtagt    780
ccacgcccta acgatgtcg actagtcgtt tggagcagca atgcactgag tgacgcagct    840
aacgcgtgaa gtcgaccgcc tggggagtac ggccgcaagg ttaaaactca aggaattga    900
cggggacccg cacaagcggt ggatgatgtg gattaatttg atgcaacgcg aaaaaccttta   960
cctaccttg acatgccagg aaccttgccg agaggcgagg gtgccttcgg gagcctggac   1020
acaggtgctg catggctgtc gtcagctcgt gtcgtgagat gttgggttaa gtcccgcaac   1080
gagcgcaacc cttgtcacta gttgccatca tttggttggg cactctagtg agactgccgg   1140
tgacaaaccg gaggaaggtg gggatgacgt caagtcctca tggcccttat gggtagggct   1200
tcacacgtca tacaatggtc ggtacagagg gttgccaagc cgcgaggtgg agccaatccc   1260
ttagagccga tcgtagtccg gatcgtagtc tgcaactcga ctacgtgaag tcggaatcgc   1320
tagtaatcgc agatcagcat gctgcggtga atacgttccc gggtcttgta cacaccgccc   1380
gtcacaccat gggagtgggt ttcaccagaa gtaggtagct taaccttcgg gagggcgctt   1440
```

<210> SEQ ID NO 68
<211> LENGTH: 1452
<212> TYPE: DNA
<213> ORGANISM: unknown
<220> FEATURE:
<223> OTHER INFORMATION: Unknown clone from enriched environmental sample that by rDNA sequence analysis has highest identity to Thauera aromatica

<400> SEQUENCE: 68

```
tggctcagga cgaacgctga cggcgtgcct aacacatgca agtcgagcgg agaatgcaga     60
aatgtttaca tggaagtatt cttagcggcg gacgggtgag taacacgtgg gtaacctgcc    120
tcaaagtggg ggatagcctt ccgaaaggaa gattaatacc gcataagcct acagtgccgc    180
atggcacagc aggaaaagga gcaatccgct ttgagatgga cccgcggcgc attagctagt    240
tggtgaggta acggctcacc aaggcgacga tgcgtagccg acctgagagg gtgatcggcc    300
acattggaac tgagacacgg cccagactcc tacgggaggc agcagtgggg aattttggac    360
```

```
aatgggcgca agcctgatcc agccatgccg cgtgagtgaa gaaggccttc gggttgtaaa    420
gctctttcgg ccgggaagaa atcgtggtct ctaacatagg ccatggatga cggtaccgga    480
ctaagaagca ccggctaact acgtgccagc agccgcggta atacgtaggg tgcgagcgtt    540
aatcggaatt actgggcgta aagcgtgcgc aggcggtttt gtaagacaga tgtgaaatcc    600
ccgggctcaa cctgggaact gcgtttgtga ctgcaaagct agagtacggc agaaggggt     660 ggaattcctg gtgtagcagt gaaatgcgta gagatcagga ggaacaccga tggcgaaggc    720 agcccctgg ggcctgtact gacgctcatg cacgaaagcg gggggagcaa acaggattag     780
ataccctggt agtccacgcc ctaaacgatg tcgactagtc gttcggagca gcaatgcact    840
gagtgacgca gctaacgcgt gaagtcgacc gcctggggag tacggccgca aggttaaaac    900
tcaaaggaat tgacgggac ccgcacaagc ggtggatgat gtggattaat tcgatgcaac     960
gcgaaaaacc ttacctaccc ttgacatgcc aggaaccttg ccgagaggcg agggtgcctt   1020
cgggagcctg acacaggtg ctgcatggct gtcgtcagct cgtgtcgtga tgttgggt      1080 taagtcccgc aacgagcgca acccttgtca ctagttgcca tcatttggtt gggcactcta   1140
gtgagactgc cggtgacaaa ccggaggaag gtggggatga cgtcaagtcc tcatggccct   1200
tatgggtagg gcttcacacg tcatacaatg gtcggtacag agggttgcca agccgcgagg   1260
tggagccaat cccttaaagc cgatcgtagt ccggatcgta gtctgcaact cgactacgtg   1320
aagtcggaat cgctagtaat cgcagatcag catgctgcgg tgaatacgtt cccgggtctt   1380
gtacacaccg cccgtcacac catgggagtg ggtttcacca gaagtaggta gcttaacctt   1440
cgggagggcg ct                                                       1452
```

<210> SEQ ID NO 69
<211> LENGTH: 1440
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. EH21

<400> SEQUENCE: 69

```
tggctcagat tgaacgctgg cggcatgctt tacacatgca agtcgaacgg cagcgggggc     60
ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgtgactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag ggggggtgg aattcctggt     660 gtaacaatga aatgcgtaga gatcaggagg aacacgatg gcgaaggcag ccccctgggc     720
ctgtactgac gctcatgcac gaaagcgtgg ggagcaaaca ggattagata ccctggtagt    780
ccacgccgta aacgatgtcg actagccgtt gggatccttg agatcttagt ggcgcagcta    840
acgcattaag tcgaccgcct ggggagtacg gccgcaaggt taaaactcaa atgaattgac    900
```

```
gggggcccgc acaagcggtg gagcatgtgg tttaattcga agcaacgcga agaaccttac    960
caggccttga catgcagaga actttccaga gatggattgg tgccttcggg agctctgaca   1020
caggtgctgc atggctgtcg tcagctcgtg tcgtgagatg ttgggttaag tcccgtaacg   1080
agcgcaaccc ttgtccttag ttaccagcac gttaaggtgg gcactctaag gagactgccg   1140
gtgacaaacc ggaggaaggt ggggatgacg tcaagtcatc atggccctta cggcctgggc   1200
tacacacgtg ctacaatggt cggtacaaag ggttgccaag ccgcgaggtg gagctaatcc   1260
cataaaaccg atcgtagtcc ggatcgtagt ctgcaactcg actacgtgaa gtcggaatcg   1320
ctagtaatcg cagatcagca tgctgcggtg aatacgttcc cgggtcttgt acacaccgcc   1380
cgtcacacca tgggagtggg tttcaccaga agtaggtagc ttaaccttcg ggagggcgct   1440
```

<210> SEQ ID NO 70
<211> LENGTH: 1438
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 70

```
tggctcagga cgaacgctgg cggcgtgcct aacacatgca agtcgagcga agtgactctg     60
agagaaattt tcggatggat cgaagagtca tcttagcggc ggacgggtga gtaacgcgtg    120
agaaacctgc ctttcacaaa gggatagcct cgggaaactg ggattaatac cttatgaaac    180
tgaattaccg catggtagat cagtcaaagc gaataagcgg tgaaagatgg tctcgcgtcc    240
tattagctag ttggtgaggt aacggctcac caaggcttcg ataggtagcc ggcctgagag    300
ggtgaacggc cacactggaa ctgagacacg gtccagactc ctacgggagg cagcagtggg    360
gaatattgca caatggagga aactctgatg cagcgacgcc gcgtgaatga tgaaggcctt    420
cgggttgtaa agttctgtcc ttggggaaga taatgacggt acccaaggag gaagccccgg    480
ctaactacgt gccagcagcc gcggtaatac gtagggtgcg agcgttaatc ggaattactg    540
ggcgtaaagc gtgcgcaggc ggttttgtaa dacagatgtg aaatccccgg gctcaacctg    600
ggaactgcgt ctgtgactgc aaggctagag tacggcagag ggggtggaa ttcctggtgt    660 agcagtgaaa tgcgtacaga tcacgaggaa caccgatggc gaaggcagcc cctggcccct    720
gtactgacgt tcatgcacaa agcgtgggg agcaaacagg gattagatac cctggtagtc    780
cacgccctaa acgatgttga ttagtcgttc ggagcagcaa tgcactgagt gacgcagcta    840
acgcgtgaag tcgaccgcct ggggagtacg gccgcaaggt taaaactcaa aggaattgac    900
ggggacccgc acaagcggtg gatgatgtgg attaattcga tgcaacgcga aaaaccttac    960
ctacccttga catgccagga accttgccga gaggcgaggg tgccttcggg agcctggaca   1020
caggtgctgc atggctgtcg tcagctcgtg tcgtgagatg ttgggttaag tcccgcaacg   1080
agcgcaaccc ttgtcactag ttgccatcat ttggttgggc actctagtga gactgccggt   1140
gacaaaccgg aggaaggtgg ggatgacgtc aagtcctcat ggcccttatg gtagggctt    1200 cacacgtcat acaatggtcg gtacagaggg ttgccaagcc gcgaggtgga gccaatccct   1260
taaagccgat cgtagtccgg atcgtagtct gcaactcgac tacgtgaagt cggaatcgct   1320
agtaatcgca gatcagcatg ctgcggtgaa tacgttcccg ggtcttgtac acaccgcccg   1380
tcacaccatg ggagtgggtt tcaccagaag taggtagctt aaccttcggg agggcgct    1438
```

<210> SEQ ID NO 71
<211> LENGTH: 1437
<212> TYPE: DNA
<213> ORGANISM: unknown
<220> FEATURE:
<223> OTHER INFORMATION: Unknown clone from enriched environmental
sample that by rDNA sequence analysis has highest identity to
Azotobacter beijerinckii

<400> SEQUENCE: 71

| | | | | | |
|---|---|---|---|---|---|
| tggctcagat | tgaacgctgg | cggcaggcct | aacacatgca | agtcgagcgg | atgagtggag | 60 |
| cttgctccat | gattcagcgg | cggacgggtg | agtaatgcct | aggaatctgc | ctggtagtgg | 120 |
| gggacaacgt | ttcgaaagga | acgctaatac | cgcatacgtc | ctacgggaga | aagtggggga | 180 |
| tcttcggacc | tcacgctatc | agatgagcct | aggtcggatt | agctagttgg | tgaggtaaag | 240 |
| gctcaccaag | gcgacgatcc | gtaactggtc | tgagaggatg | atcagtcaca | ctggaactga | 300 |
| gacacggtcc | agactcctac | gggaggcagc | agtggggaat | attggacaat | gggcgaaagc | 360 |
| ctgatccagc | catgccgcgt | gtgtgaagaa | ggtcttcgga | ttgtaaagca | ctttaagttg | 420 |
| ggaggaaggg | cagtaagtta | ataccttgct | gttttgacgt | taccgacaga | ataagcaccg | 480 |
| gctaacttcg | tgccagcagc | cgcggtaata | cgaaggtgc | aagcgttaat | cggaattact | 540 |
| gggcgtaaag | cgcgcgtagg | tggttcgtta | agttggatgt | gaaagccccg | ggctcaacct | 600 |
| gggaactgca | tccaaaacta | gcagctaga | gtatggcaga | gggtggtgga | atttcctgtg | 660 |
| tagcggtgaa | atgcgtagat | ataggaagga | acaccagtgg | cgaaggcgac | cacctggggt | 720 |
| aatactgaca | ctgaagtgcg | aaagcggggg | gagcaaacag | gattagatac | cctggtattc | 780 |
| cacgccgtaa | acgatgtcga | ctagccgttg | ggatccttga | gatcttagtg | gcgcagctaa | 840 |
| cgcattaagt | cgaccgcctg | gggagtacgg | ccgcaaggtt | aaaactcaaa | ggaattgacg | 900 |
| gggacccgca | caagcggtgg | atgatgtgga | ttaattcgat | gcaacgcgaa | aaaccttacc | 960 |
| tacccttgac | atgccaggaa | ccttgccgag | aggcgagggt | gccttcggga | gcctggacac | 1020 |
| aggtgctgca | tggctgtcgt | cagctcgtgt | cgtgagatgt | tgggttaagt | cccgcaacga | 1080 |
| gcgcaaccct | tgtcactagt | tgccatcatt | tggttgggca | ctctagtgag | actgccggtg | 1140 |
| acaaaccgga | ggaaggtggg | gatgacgtca | agtcctcatg | gcccttatgg | gtagggcttc | 1200 |
| acacgtcata | caatggtcgg | tacagagggt | tgccaagccg | cgaggtggag | ccaatccctt | 1260 |
| aaagccgatc | gtagtccgga | tcgtagtctg | caactcgact | acgtgaagtc | ggaatcgcta | 1320 |
| gtaatcgcag | atcagcatgc | tgcggtgaat | acgttcccgg | gtcttgtaca | caccgcccgt | 1380 |
| cacaccatgg | gagtgggttt | caccagaagt | aggtagctta | accttcggga | gggcgct | 1437 |

<210> SEQ ID NO 72
<211> LENGTH: 1452
<212> TYPE: DNA
<213> ORGANISM: unknown
<220> FEATURE:
<223> OTHER INFORMATION: Unknown clone from enriched environmental
sample that by rDNA sequence analysis has highest identity to
Azotobacter beijerinckii

<400> SEQUENCE: 72

| | | | | | |
|---|---|---|---|---|---|
| agagtttgat | tctggctcag | attgaacgct | ggcggcatgc | tttacacatg | caagtcgaac | 60 |
| ggcagcgggg | gcttcggcct | gccggcgagt | ggcgaacggg | tgagtaatgc | atcggaacgt | 120 |
| gcccatgtcg | tgggggataa | cgtatcgaaa | ggtacgctaa | taccgcatac | gtcctgaggg | 180 |
| agaaagcggg | ggatcttcgg | acctcgcgcg | attggagcgg | ccgatgtcgg | attagctagt | 240 |
| aggtgaggta | aaggctcacc | taggcgacga | tccgtagcgg | gtctgagagg | atgatccgcc | 300 |

```
acactgggac tgagacacgg cccagactcc tacgggaggc agcagtgggg aattttggac    360
aatgggcgca agcctgatcc agccatgccg cgtgagtgaa gaaggccttc gggttgtaaa    420
gctctttcgg ccgggaagaa atcgtggtct ctaacatagg ccatggttga cgttaccgac    480
agattaagca ccggctaact tcgtgccagc agccgcggta atacgaaggg tgcaagcgtt    540
aatcggaatt actgggcgta aagcgcgcgt aggtggttcg ttaagttgga tgtgaaagcc    600
ccgggctcaa cctgggaact gcatccaaaa ctggcgagct agagtatggc agagggtggt    660
ggaatttcct gtgtagcggt gaaatgcgta catataggaa ggaacaccag tggcgaaggc    720
gaccacctgg gctaatactg acactgaggt gcgaaagcgt ggggagcaaa caggattaga    780
taccctggta gtccacgccg taaacgatgt cgactagccg ttgggatcct tgagatctta    840
gtggcgcagc taacgcatta agtcgaccgc ctggggagta cggccgcaag gttaaaactc    900
aaatgaattg acggggcccc gcacaagcgg tggagcatgt ggtttaattc gaagcaacgc    960
gaagaacctt accaggcctt gacatgctga gaacctgcca gagatggcgg ggtgccttcg   1020
ggaactcaga cacaggtgct gcatggctgt cgtcagctcg tgtcgtgaga tgttgggtta   1080
agtcccgtaa cgagcgcaac ccttgtcctt agttaccagc acgttatggt gggcactcta   1140
aggagactgc cggtgacaaa ccggaggaag gtggggatga cgtcaagtca tcatggccct   1200
tacgccctgg gctacacacg tgctacaatg gtcggtacaa agggttgcca agccgcgagg   1260
tggagctaat cccataaaac cgatcgtagt ccggatcgca gtctgcaact cgaccgcgtg   1320
aagtcggaat cgctagtaat cgtgaatcag aatgtcacgg tgaatacgtt cccgggcctt   1380
gtacacaccg cccgtcacac catggggggtg gttgctcca gaagtagcta gtctaacctt   1440
cgggggggacg gt                                                      1452
```

<210> SEQ ID NO 73
<211> LENGTH: 893
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 73

```
cggttacctt gttacgactt caccctcctc gccggacgta ccttcggaac cgcccccccct    60
cgcgggttgg gctggcgact tcgggtaccc ccgactcgga tggtgtgacg ggcggtgtgt   120
acaaggcccg ggaacgtatt caccgcgcca tgctgatgcg cgattactag cgattccaac   180
ttcatggagt cgggttgcag actccaatcc gtactgggac cggctttaag ggattggctc   240
cacctcgcgg cttggcaacc ctctgtaccg accattgtat gacgtgtgaa gccctaccca   300
taagggccat gaggacttga cgtcatcccc accttcctcc ggtttgtcac cggcagtctc   360
actagagtgc ccaaccaaat gatggcaact agtgacaagg gttgcgctcg ttgcgggact   420
taacccaaca tctcacgaca cgagctgacg acagccatgc agcacctgtg tccaggctcc   480
cgaaggcacc ctcgcctctc ggcaaggttc ctggcatgtc aagggtaggt aaggtttttc   540
gcgttgcatc gaattaatcc acatcatcca ccgcttgtgc gggtccccgt caattccttt   600
gagttttaac cttgcggccg tactccccag gcggtcgact tcacgcgtta gctgcgtcac   660
tcagtgcatt gctgctccga acgactagtc gacatcgttt agggcgtgga ctaccagggt   720
atctaatcct gtttgctccc cacgctttcg tgcatgagcg tcagtacagg cccaggggggc   780
tgccttcgcc atcggtgttc ctcctgatct ctacgcattt cactgctaca ccaggaattc   840
```

```
caccccctc tgccgtactc tagccttgca gtcacaaacg cagttcccag gtt           893
```

<210> SEQ ID NO 74
<211> LENGTH: 846
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 74

```
agcggtttgt agacagatgt gaatcccggc tcaactggac tgcgtttgat gcaagctaga    60
gtcgcagagg gggggaatct gtgtagcagt gaatgcgtag agatcagagg acacgatgcg   120
aagcagcccc tgggctgtac tgacgtcatg cacgaaagcg ggggagcaaa caggattaga   180
tacctggtag tcacgcctaa acgatgtcga ctagtcgtcg gagcagcaat gcactgagtg   240
acgcagctaa cgcgtgaagt cgaccgctgg ggagtacggc cgcaaggtta aaactcaaag   300
gaattgacgg ggacccgcac aagcggtgga tgatgtggat taattcgatg caacgcgaaa   360
aaccttacct acccttgaca tgccaggaac cttgccgaga ggcgagggtg ccttcgggag   420
cctggacaca ggtgctgcat ggctgtcgtc agctcgtgtc gtgagatgtt gggttaagtc   480
ccgcaacgag cgcaacccct gtcactagtt gccatcattt ggttgggcac tctagtgaga   540
ctgccggtga caaaccggag gaaggtgggg atgacgtcaa gtcctcatgg cccttatggg   600
tagggcttca cacgtcatac aatggtcggt acagagggtt gccaagccgc gaggtggagc   660
caatccctta aagccgatcg tagtccggat cgtagtctgc aactcgacta cgtgaagtcg   720
gaatcgctag taatcgcaga tcagcatgct gcggtgaata cgttcccggg tcttgtacac   780
accgcccgtc acaccatggg agtgggtttc accagaagta ggtagcttaa ccttcgggag   840
ggcgct                                                              846
```

<210> SEQ ID NO 75
<211> LENGTH: 1426
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium chartatabidium

<400> SEQUENCE: 75

```
tggctcagga cgaacgctgg cggcgtgcct aacacatgca agtcgagcgg agaatgcaga    60
aatgtttaca tggaagtatt cttagcggcg gacgggtgag taacacgtgg gtaacctgcc   120
tcgaagtggg ggatagcctt ccgaaaggaa gattaatacc gcataagcct acagtgccgc   180
atggcacagc aggaaaagga gcaatccgct ttgagatgga cccgcggcgc attagctagt   240
tggtgaggta acggctcacc aaggcgacga tgcgtagccg acctgagagg gtgatcggcc   300
acattggaac tgagacacgg tccagactcc tacgggaggc agcagtgggg aatattgcac   360
aatgggcgaa agcctgatgc agcaacgccg cgtgagtgat gaaggccttc gggtcgtaaa   420
gctctttgat cagggatgat aatgacagta cctgaaaaac aagccacggc taactacgtg   480
ccagcagccg cggtaatacg taggtggcga gcgttgtccg gaattactgg gcgtaaagga   540
tgcgtaggtg gatacttaag tgggatgtga atccccggg ctcaacccgg gaactgcatt   600
ccaaactggg tatctagagt gcaggagagg aaagcggaat tcctagtgta gcggtgaaat   660
gcgtagatat taggaggaac accagtggcg aaggcggctt tctggactgt aactgacact   720
```

```
gaggcatgaa agcgtgggta gcaaacagga ttagataccc tggtagtcca cgccgtaaac    780
gatgggtact aggtgtagga ggtatcgacc ccttctgtgc cgttgttaac acaataagta    840
ccccgcctgg ggagtacggt cgcaagacta aaactcaaag gaattgacgg gggcccgcac    900
aagcagcgga gcatgtggtt taattagaag caacgcgaaa aaccttacct acccttgaca    960
tgccaggaac cttgccgaga ggcgagggtg ccttcgggag cctggacaca ggtgctgcat   1020
ggctgtagtc agctcgtgtc gtgagatgtt gggttaagtc ccgcaacgag cgcaacccett   1080 gtcactagtt gccatcattt ggttgggcac tctagtgaga ctgccggtga caaaccggag   1140
gaaggtgggg atgacgtcaa gtcctcatgg cccttatggg tagggcttca cacgtcatac   1200
aatggtcggt acagagggtt gccaagtcgt gaggtggagc caatcccttta aagccgatcg   1260 tagtccggat cgtagtctgc aactcgacta cgtgaagtcg gaatcgctag taatcgcaga   1320
tcagcatggt gcggtgaata cgttcccggg tcttgtacac accgcccgtc acaccatggg   1380
agtgggtttc accagaagta ggtagcttaa ccttcgggag ggcgct             1426
```

<210> SEQ ID NO 76
<211> LENGTH: 1420
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium aceticum

<400> SEQUENCE: 76

```
tggctcagat tgaacgctgg cggcatgctt tacacatgca agtcgaacgg cagcgggggc     60
ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctaaccta ggcgacgatc cgtagcgggt ctgagagggt gaacggccac actggaactg    300
agacacggtc cagactccta cgggaggcag cagtggggaa tattgcacaa tggaggaaac    360
tctgatgcag cgacgccgcg tgaatgatga aggccttcgg gttgtaaagt tctgtccttg    420
gggaagataa tgacggtacc caaggaggaa gccccggcta actacgtgcc agcagccgcg    480
gtaatacgta gggggcgagc gttgtccgga attattgggc gtaaagggtt cgcaggcggt    540
ctgataagtc agatgtgaaa ggcgtaggct caacctacgt aagcatttga aactgtcaga    600
cttgagttaa ggagaggaaa gtggaattcc tagtgtagcg gtgaaatgcg tagatattag    660
gaggaatacc agtggcgaag gcgactttct ggacttatac tgacgctgag gaacgaaagc    720
gtggggagca acaggatta gatacccctgg tagtccacgc cgtaaacgat gagtgctagg    780
tgttgggggt caaaccctcgg tgccgcagct aacgcattaa gcactccgcc tggggagtac    840
gtacgcaagt atgaaactca aaggaattga cggggacccg cacaagcagc ggagcatgtg    900
gtttaattcg aagcaacgcg aagaacctta ccagggcttg acatgccgct gaccggttta    960
gagatagatc tttacccttc ggggtacagc ggacacaggt ggtgcatggt tgtcgtcagc   1020
tcgtgtcgtg agatgttggg ttaagtcccg caacgagcgc aacccttgtc tttagttgcc   1080
atcattaagt tgggcactct aaagagactg ccgatgacaa atcggaggaa ggtggggatg   1140
acgtcaaatc atcatgccct ttatgtcctg gctacacac gtgctacaat ggtcggtaca   1200
acgagaagca agtcagcgat ggcaagcaaa tctctaaaag ccgatcccag ttcggattgc   1260
aggctgcaac tcgcctgcat gaagtcggag ttgctagtaa tcgcggatca gaatgccgcg   1320
```

```
gtgaatgcgt tcccgggtct tgtacacacc gcccgtcaca ccatgggagt tgtcaatacc    1380
cgaagccagt gagctaacca taaaaggagg cagctgtcga                          1420
```

<210> SEQ ID NO 77
<211> LENGTH: 1430
<212> TYPE: DNA
<213> ORGANISM: unknown
<220> FEATURE:
<223> OTHER INFORMATION: Unknown clone from enriched environmental
      sample that by rDNA sequence analysis has highest identity to
      Deferribacter desulfuricans

<400> SEQUENCE: 77

```
agagtttgat tatggctcag aacgaacgct ggcggcgtgc ttaacacatg caagtcaagg      60
agaaagtctc ttcggggggcg agtaaactgg cgcacgggtg agtaacgcgt gaggaacctg    120
cccatatgtc tgggataacc tgctgaaaag cgggctaata ctggatatat tgtttaccgc    180
atggtggaca aggaaagttg gtgtaagcta acgcatatg atggtctcgc gtctgattag     240
ctagttggtg ggtaaaggc tcaccaaggc aacgatcagt agcgggtctg agaggatgat    300
ccgccacact gggactgaga cacggcccag actcctacgg gaggcagcag tggggaatat    360
tgcacaatgg gcgaaagcct gatgcagcaa cgccgcgtga gtgatgaagg ccttcgggtc    420
gtaaagctct ttgatcaggg atgataatga cagtacctga aaaacaagcc acggctaact    480
acgtgccagc agccgcggta atacgtatgt ggcgagcgtt gtccggaatt attgggcgta    540
aagggttcgc aggcggtctg ataagtcaga tgtgaaaggc gtaggctcaa cctacgtaag    600
catttgaaac tgtcagactt gagttaagga gaggaaagtg gaattcctag tgtagcggtg    660
aaatgcgtag atattaggag gaataccagt ggcgaaggcg actttctgga cttatactga    720
cgctgaggaa cgaaagcgtg gggagcaaac aggattagat accctggtag tccacgccgt    780
aaacgatgag tgctaggtgt tgggggtcaa acctcggtgc cgcagctaac gcattaagca    840
ctccgcctgg ggagtacgta cgcaagtatg aaactcaaag gaattgacgg ggacccgcac    900
aagcagcgga gcatgtggtt taattcgaag caacgcgaag aaccttacca gggcttgaca    960
tgccgctgac cggtttagag atagatcttt acccttcggg gtacggcgga cacaggtggt   1020
gcatggttgt cgtcagctcg tgtcgtgaga tgttgggtta agtcccgcaa cgagcgcaac   1080
ccttattttt agttgctacc attcagttga gcactctaaa gagactgccc gggttaaccg   1140
ggaggaaggt ggggatgacg tcaaatcatc atgccccctta tgtctagggc tacacacgtg   1200
ctacaatggt cggtacagag ggttgccaag ccgcgaggtg gagccaatcc cttaaagccg   1260
atcgtagtcc ggatcgtagt ctgcaactcg actacgtgaa gtcggaatcg ctagtaatcg   1320
cagatcagca tgctgcggtg aatacgttcc cgggtcttgt acacaccgcc cgtcacacca   1380
tgggagtggg tttcaccaga agtaggtagc ttaaccttcg ggagggcgct              1430
```

<210> SEQ ID NO 78
<211> LENGTH: 1436
<212> TYPE: DNA
<213> ORGANISM: unknown
<220> FEATURE:
<223> OTHER INFORMATION: Unknown clone from enriched environmental
      sample that by rDNA sequence analysis has highest identity to
      Bacteroides sp. EH30

<400> SEQUENCE: 78

```
tggctcagga tgaacgctag cggcaggctt aatacatgca agtcgaacgg gattcgaggt     60
agcaatactt tgatgagagt ggcgcacggg tgcgtaacgc gtatgcaacc tacctttaac    120
```

```
tgggagatag ccccgagaaa tcgggattaa tacccataa cattacgaat tggcatcaat      180
ttgtgattaa agctccggcg gttagagatg gcatgcgtg acattagctg gttggtgagg      240
taacggctca ccaaggcaac gatgtctagg ggtcctgaga gggttatccc ccacactggt     300
actgagacac ggaccagact cctacgggag gcagcagtaa ggaatattgg tcaatgggcg     360
caagcctgaa ccagccatgc cgcgtgcagg aagacgggcc tatgggttgt aaactgcttt     420
tatcagggaa taaaccccg ctcgtgagcg gggctgaagg tacctgagga ataagcatcg      480
gctaactccg tgccagcagc cgcggtaata cggaggatgc aagcgttatc cggattcatt     540
gggtttaaag ggtgcgcagg cggattggta agtcaggggt gaaatcccac agctcaactg     600
tggaactgcc tttgatactg tcagtctaga gtatagttga agttggcgga atgtgtcatg     660
tagcggtgaa atgcttagat atgacacaga acaccgatcg cgaaggcagc tagctaagct     720
ataactgacg ctcatgcacg aaagcgtggg gatcaaacag gattagatac cctggtagtc     780
cacgctgtaa acgatgatta ctcgatgttg gcgatacaca gtcagcgttt gagcgaaagc     840
aataagtaat ccacctgggg agtacggccg caaggttaaa actcaaatga attgacgggg     900
gcccgcacaa gcggtggagc atgtggttta attcgaagca acgcgaagaa ccttaccagg     960
ccttgacatg cagagaactt tccagagatg gattggtgcc ttcgggagct ctgacacagg    1020
tgctgcatgg ctgtcgtcag ctcgtgtcgt gagatgttgg gttaagtccc gtaacgagcg    1080
caacccttgt ccttagttac cagcacgtta aggtgggcac tctaaggaga ctgccggtga    1140
caaaccggag gaaggtgggg atgacgtcaa gtcatcatgg cccttacggc ctgggctaca    1200
cacgtgctac aatggtcggt acaaagggtt gccaagccgc gaggtggagc taatcccata    1260
aaaccgatcg tagtccggat cgcagtctgc aactcgactg cgtgaagtcg gaatcgctag    1320
taatcgtgaa tcagaatgtc acggtgaata cgttcccggg ccttgtacac accgcccgtc    1380
acaccatggg agtgggtttc accagaagta ggtagcttaa ccttcgggag ggcgct        1436
```

<210> SEQ ID NO 79
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 79

```
tggctcagga cgaacgctgg cggcgtgcct aacacatgca agtcgagcga agtgactcgg      60
agagaagttt tcggatggat cgaagagtca tcttagcggc ggacgggtga gtaacgcgtg    120
agaaacctgc ctttcacaaa gggatagcct cgggaaactg ggattaatac cttatgaaac    180
tgaattaccg catggtagat cagtcaaagc gaataagcgg tgaaagatgg tctcgcgtcc    240
tattagctag ttggtgaggt aacggctcac caaggcttcg ataggtagcc ggcctgagag    300
ggtgaacggc cacactggaa ctgagacacg gtccagactc ctacgggagg cagcagtggg    360
gaatattgca caatggagga aactctgatg cagcgacgcc gcgtgaatga tgaaggcctt    420
cgggttgtaa agttctgtcc ttggggaaga taatgacggt acccaaggag gaagccccgg    480
ctaactacgt gccagcagcc gcggtaatac gtaggggggc agcgttgtcc ggaattattg    540
ggcgtaaagg gttcgcaggc ggtctgataa gtcagatgtg aaaggcgtag gctcaaccta    600
cgtaagcatt tgaaactgtc agacttgagt taaggagagg aaagtggaat tcctagtgta    660
gcggtgaaat gcgtagatat taggaggaat accagtggcg aaggcgactt tctggactta    720
```

-continued

```
tactgacgct gaggaacgaa agcgtgggga gcaaacagga ttagataccc tggtaattcc      780
cgccgtaaac gatgagtgct aggtgttggg ggtcaaacct cggtgccgca gctaacgcat      840
taagcactcc gcctggggag tacgtacgca agtatgaaac tcaaaggaat tgacggggac      900
ccgcacaagc agcggagcat gtggtttaat ttgaagcaac gcgaagaacc ttaccagggc      960
ttgacatgcc gctgaccggt gcagagatgc atctttatcc ttcggggtac agcggacaca     1020
ggtggtgcat ggttgtcgtc agctcgtgtc gtgagatgtt gggttaagtc ccgcaacgag     1080
cgcaacccct tgtctttagtt gccatcatta agttgggcac tctaaagaga ctgccgatga    1140
caaatcggag gaaggtgggg atgacgtcaa atcatcatgc cctttatgtc ctgggctaca     1200
cacgtgctac aatggtcggt acaacgaaag caagtcagc gatggcaagc aaatctctaa      1260
aagccgatcc cagttcggat tgcagtctgc aactcgactg catgaagtcg gaatcgctag     1320
taatcgcagg tcagcaaaac tgcggtgaat acgttcccgg gccttgtaca caccgcccgt     1380
cacaccacgg gagtcggttg tacctgaagc cggtggccca accgcaaggg gggagccgt     1439
```

<210> SEQ ID NO 80
<211> LENGTH: 882
<212> TYPE: DNA
<213> ORGANISM: unknown
<220> FEATURE:
<223> OTHER INFORMATION: Unknown clone from enriched environmental sample that by rDNA sequence analysis has highest identity to Pseudomonas putida

<400> SEQUENCE: 80

```
tggctcagat tgaacgctgg cggcatgctt tacacatgca agtcgaacgg cagcgggggc       60
ttcggcctgc cggcgagtgg cgaacgggtg agtaatgcct aggaatctgc ctggtagtgg      120
gggacaacgt ttcgaaagga acgctaatac cgcatacgtc ctacgggaga agtgggggga     180
tcttcggacc tcacgctatc agatgagcct aggtcggatt agctagttgg tgaggtaaag     240
gctcaccaag gcgacgatcc gtaactggtc tgagaggatg atcagtcaca ctggaactga     300
gacacggtcc agactcctac gggaggcagc agtggggaat attggacaat gggcgaaagc     360
ctgatccagc catgccgcgt gtgtgaagaa ggtcttcgga ttgtaaagca ctttaagttg     420
ggaggaaggg cagtaagtta ataccttgct gttttgacgt taccgacaga ataagcaccg    480
gctaacttcg tgccagcagc cgcggtaata cgaagggtgc aagcgttaat cggaattact     540
gggcgtaaag cgcgcgtagg tggttcgtta agttagatgt gaaagccccg gctcaacct     600 gggaactgca tccaaaactg gcgagctaga gtatggcaga gggtggtgga atttcctgtg    660
tagcggtgaa atgcgtagat ataggaagga acaccagtgg cgaaggcgac cacctgggct     720
aatactgaca ctgaggtgcg aaagcgtggg gagcaaacag gattagatac cctggtagtc     780
cacgccgtaa acgatgtcga ctagccgttg ggatccttga gatcttagtg gcgcagctaa    840
cgcattaagc gtaccgcctg gggagtacgg ccgcaaggtt ga                         882
```

<210> SEQ ID NO 81
<211> LENGTH: 1442
<212> TYPE: DNA
<213> ORGANISM: unknown
<220> FEATURE:
<223> OTHER INFORMATION: Unknown clone from enriched environmental sample that by rDNA sequence analysis has highest identity to Clostridium aceticum

<400> SEQUENCE: 81

```
tggctcagga tgaacgctgg cggcgtgcct aacacatgca agtcgagcgg tatatagtgg       60
```

| | |
|---|---:|
| aatgaaactt cggtcgagtg aagctataga gagcggcgga cgggtgagta acgcgtaggc | 120 |
| aacctgcccc atacagaggg atagcctcgg gaaaccggga ttaaaacctc ataacgcgag | 180 |
| gagttcacat ggactgctcg ccaaagattc atcggtatgg gatgggcctg cgtctgatta | 240 |
| gctagttggt gaggtaacgg ctcaccaagg cgacgatcag tagccgacct gagagggtaa | 300 |
| tcggccacat tggaactgag acacggtcca aactcctacg ggaggcagca gtggggaatt | 360 |
| ttgcacaatg ggggcaaccc tgatgcagcg acgccgcgtg aacgaggaag gccttcgggt | 420 |
| cgtaaagttc tttcgacggg gaagaaatgt tatacgagta actgcgtata atttgacggt | 480 |
| acctgtagaa gcagcccgg ctaactccgt gccagcagcc gcggtaatac ggaggggcg | 540 |
| agcgttgttc ggagttactg ggcgtaaagc gcacgtaggc ggtgcggtaa gtcaggggtt | 600 |
| aaaggtcaca gctcaactgt gataaggcct ttgatactat cgtgctagag tgtcagagag | 660 |
| ggtagcggaa ttcccggtgt agcggtgaaa tgcgtagata tcgggaggaa caccagtagc | 720 |
| gaaggcggct acctggctga taactgacgc tgaggtgcga gagcgtgggg agcaaacagg | 780 |
| attagatacc ctggtagtcc acgctgtaaa cgatggacgt taggtgttgg gggaaccgac | 840 |
| cccctcagtg ccgaagctaa cgcgttaaac gtcccgcctg ggagtacgg ccgcaaggtt | 900 |
| gaaactcaaa ggaattgacg ggggcccgca caagcggtgg agcatgtggt ttaattcgaa | 960 |
| gcaacgcgca gaaccttacc agcccttgac ataccggtcg cggacacaga gatgtgtctt | 1020 |
| tcagttcggc tggaccggat acaggtgctg catggctgtc gtcagctcgt gccgtgagat | 1080 |
| gttgggttaa gtcccgcaac gagcgcaacc ctcgccctta gttgccagca tttagttggg | 1140 |
| cactctaagg ggactgccgg tgataagccg agaggaaggt ggggatgacg tcaagtcctc | 1200 |
| atggccctta cgggctgggc tacacacgtg ctacaatggt ggtgacagtg ggcagcgagc | 1260 |
| acgcgagtgt gagctaatct ccaaaagcca tctcagttcg gattgcactc tgcaactcga | 1320 |
| gtgcatgaag ttggaatcgc tagtaatcgc ggatcagcat gccgcggtga atacgttccc | 1380 |
| gggccttgta cacaccgccc gtcacaccat gggagttggt tttacccgaa ggcgctgtgc | 1440 |
| ta | 1442 |

<210> SEQ ID NO 82
<211> LENGTH: 861
<212> TYPE: DNA
<213> ORGANISM: unknown
<220> FEATURE:
<223> OTHER INFORMATION: Unknown clone from enriched environmental
   sample that by rDNA sequence analysis has highest identity to
   Anaerovorax sp. EH34

<400> SEQUENCE: 82

| | |
|---|---:|
| gtgaaaggca atagcttaac tattgtaagc cttgcgaact gtgtggcttg agtgcaggag | 60 |
| aggaaagtgg aattcctagt gtagcggtga aatgcgtaga tattaggagg aacaccagtg | 120 |
| gcgaaggcga cttctggac tgtaactgac actgaggcac gaaagcgtgg gagcaaacag | 180 |
| gattagatac cctggtagtc cacgccgtaa acgatgagca ctaggtgtcg ggtcgcaag | 240 |
| acttcggtgc cgcagttaac gcattaagtg ctccgcctgg ggagtacgca cgcaagtgtg | 300 |
| aaactcaaag gaattgacgg ggacccgcac aagcagcgga gcatgtggtt taattcgaag | 360 |
| caacgcgaag aaccttacca gggcttgaca tccctctgac agtcccttaa ccgggacctt | 420 |
| cttcggacag aggagacagg tggtgcatgg ttgtcgtcag ctcgtgtcgt gagatgttgg | 480 |
| gttaagtccc gcaacgagcg caacccttgt ctttagttgc catcattcag ttgggcactc | 540 |
| tagagagact gccgaggata actcggagga aggtggggat gacgtcaaat catcatgccc | 600 |

```
cttatgccct gggctacaca cgtgctacaa tggctggtac aaagagacgc aagaccgcga    660
ggtggagcaa atctcaaaaa ccagtcccag ttcggattgc aggctgcaac tcgcctgcat    720
gaagttggag ttgctagtaa tcgcagatca gaatgctgcg gtgaatgcgt tcccgggtct    780
tgtacacacc gcccgtcaca ccatgggagt tgtcaatacc cgaagccagt gagctaacca    840
taaaaggagg cagctgtcga a                                              861

<210> SEQ ID NO 83
<211> LENGTH: 620
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas putida

<400> SEQUENCE: 83
tggctcagat tgaacgctgg cggcaggcct aacacatgca agtcgagcgg atgaatggag     60
cttgctccat gattcagcgg cggacgggtg agtaatgcct aggaatctgc ctggtagtgg    120
gggacaacgt ttcgaaagga acgctaatac cgcatacgtc ctacgggaga agtgggggga    180
tcttcggacc tcacgctatc agatgagcct aggtcggatt agctagttgg cgaggtaaag    240
gctcaccaag gcgacgatcc gtaactggtc tgagaggatg atcagtcaca ctggaactga    300
gacacggtcc agactcctac gggaggcagc agtggggaat attggacaat gggcgaaagc    360
ctgatccagc catgccgcgt gtgtgaagaa ggtcttcgga ttgtaaagca ctttaagttg    420
ggaggaaggg cagtaagtta ataccttgct gttttgacgt taccgacaga ataagcaccg    480
gctaacttcg tgccagcagc cgcggtaata cgtaaggtgc gagcgttaat cggaattact    540
gggcgtaaag cgtgcgcagg cggttttgta agacagatgt gaaatccccg ggctcatcct    600
gggaactgcg tctgtgactg                                                620

<210> SEQ ID NO 84
<211> LENGTH: 854
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 84
gccctgggct caacatgggc atccatccag acaggcgagc tagagtatag cagaggggtg     60
gtgtaatttc cagcgtagcg atgaaatgag ttgagatagg aagccacacc agaagggaag    120
cagaccacct gggataatca tgacagtgag gtacgaaagc gtgcggagca aacaagataa    180
catacccgtg cagtccatgc agtaaatgat gtcgcctagc cgatgggatc catcagatcg    240
gagcggcgca gctaatgcac taagtgcacc gcgtggggag tacggccgca aggtttcaaa    300
tcaaatgaat tggcggggga ccgcacaagc ggcgcagcat gtggtttaat tcgaagcaac    360
gagcagaacc ttaccaggcc atcccatgca tagaactttc cagagaggga tcggggcctt    420
ccggaggtgt gacaccggtg gcgccaggcc gttgttaagt gggtcctgg gatggtgggg    480 taaattccgt aacgagggcc aaccctgtct ttagttaccc acccgttaag gtgggcactc    540
taaggagacc gccggggaca aaccggagga aggtggggat gacgtcaagt catcatggcc    600
cttacggcct gggctacaca cgtgctacaa tggtcggtac aaagggttgc caagccgcga    660
ggtggagcta atcccataaa accgatcgta gtccggatcg cagtctgcaa ctcgactgcg    720
```

-continued

```
tgaagtcgga atcgctagta atcgtgaatc agaatgtcac ggtgaatacg ttcccgggcc    780
ttgtacacac cgcccgtcac accatgggag tgggttgctc cagaagtagc tagtctaacc    840
ttcgggggga cggt                                                     854

<210> SEQ ID NO 85
<211> LENGTH: 824
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 85
caaatctcgc tcaactcgc gcttggtttg catgcagctt cgtagtgtga gcgagtggat     60
cctgcttgca atgaatgagt caagtcagat ggagcacgga tggcagggat ctcctcgcgc   120
atgtactacg tcttgcacgc aagagtgagg agcaaacaag caatagctac ctgttactcc   180 tcccccctcaa tgatgatgat tattagtcgt agcagcaaaa ctctggtgtc gaagctaata   240
cggaagtctc acctggggag tactgcgcat tataaatact caaaggattt tggtgtcgcc   300
ccccagcggg gatatgtgga ttaattagat gaaacgcgaa aaaccttccc tccctcgac    360 atacgacgaa ccctttgaga ggggagggtg cttttgggag cctggacaca ggtgccgcat   420
gggtgtcgtc acctcgtgtc gtgagatgtt gggttatgtc tcgcaacgag cgcaaccct    480 gtcactagcg ccatcatttg gggggcact ctagtgagac cccggtgaca aaccggagga    540 agggggggg gacgtcaagt cctcatggcc cttatgggta gggcttccca cgtctcacaa    600
tggtcggtac agaggggtc ccagcccccg aggggagcc aatccccaaa gccgatcgta    660
gtccggatgg tagtttgcaa ctcgcctacg tgaagtcgga atcgtttgta attgcagatc    720
accatggtgc ggggaatacc ttcccgggtt tggtacccc cgcccctccc cccatggggg    780
ggggtttccc cggaagtagg aagcttaccc ttcgggggg gggt                     824

<210> SEQ ID NO 86
<211> LENGTH: 827
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. EH36

<400> SEQUENCE: 86
tatggaagag agtcggttag tgcgtggagg agctgcgtat gtatctactt ctctccgctc     60
tcctctctgc atgcgtgtca gacagccaga gggggcgggg tccccatcca tcgttgtctt   120
actttatgca ttaatgatac aacaggagta aaccccctc ttctgtatat agcatcgcag    180
tagcaacaac agctgttggg tggagcaggg gatgattat catatgtcta aaacagcccg    240
cgcgcacgct ttatgcacag tatttgattg aaactcgcac cccctgtat atccccgggg    300 tgccgcacac atagttaggg ggtgttttt tttccggcac cccacccccg cgcgtgttag    360
agagaccgtg attttttttg gcggagagag agctttataa accgaagggt tttcactcac   420
ccgcggcagg ggggatcag gcttgcgccc cttttcaaaa aattccccc ggcccccccc    480 cgaggggggg tggggccgtt tttcagtccc cagggggggg gggtatcctc ttttcacccc   540
cccggattgt tgtggagggg gggggtttca ccccacggaa agatacaaac ccattaagcg   600
ctccaatcgc gggaggtcgg aagatccccc gcttttttccc tcaggaggtt tgggtatta   660
```

```
gggtaccttt cgatacgttt tccccccgc cagggcacg tttcgagcca ttattcaccc      720
gtttgcccct tgccggcagg ccgaagcccc ccctcccttt ggaatggcat ttgtaaagca    780
tgcccccagg gttcaatttg agccaaaata aaacttaaag ggggaat                 827

<210> SEQ ID NO 87
<211> LENGTH: 349
<212> TYPE: DNA
<213> ORGANISM: unknown
<220> FEATURE:
<223> OTHER INFORMATION: Unknown clone from enriched environmental
      sample that by rDNA sequence analysis has highest identity to
      FLexistipes sp. vp180

<400> SEQUENCE: 87
ctattgtcag ttgccatcaa gtaaggtggg cactgtaaag agtccgctgg ggataacccg     60
gaggaaggtg gggacgatgt caagtcatca tggtcgtgat gtacagggtt acgcacctga   120
tacaatggtg catacagagg gcagtgagac accgacgtta agagaatacg ttaaagtgca   180
cctcacttcg gaatgcagta tgcaaatcga atgcatggtg ttggaattgt tagtaattgc   240
aggtcagcaa tagtggggtg attacgttcc cgggcatggt acacaccgcc agtcacacca   300
tgggagtcgg ttgtacatga agccggtggc ccaaccgcaa gggggagc                349
```

STEADY STATE ANAEROBIC DENITRIFYING CONSORTIUM FOR APPLICATION IN IN-SITU BIOREMEDIATION OF HYDROCARBON-CONTAMINATED SITES AND ENHANCED OIL RECOVERY

This application claims the benefit of U.S. Provisional Application 61/154,542, filed Feb. 23, 2009.

FIELD OF INVENTION

This disclosure relates to the field of environmental microbiology. More specifically, a steady state consortium of anaerobic denitrifying microorganisms is developed with functionality in environmental microbiology and its population is defined at molecular levels. This consortium is used for enhanced oil recovery and in situ bioremediation of hydrocarbon-contaminated sites.

BACKGROUND OF THE INVENTION

The challenge to meet the ever increasing demand for oil has resulted in increasing activities in crude oil recovery from oil reservoirs for refinery processes and various other applications. These activities have resulted in contaminating various environments such as soil, groundwater, sand, drinking water, etc, with hydrocarbons. There are now two worldwide challenges that need to be met: 1) recovering the petroleum deposits for oil reservoirs; and 2) remediating the hydrocarbon-contaminated environmental sites.

Heavy crude oil in the form of petroleum deposits and oil reservoirs are distributed worldwide and because of its relatively high viscosity, it is essentially immobile and cannot be easily recovered by conventional primary and secondary means. Expanding efforts to develop alternative cost efficient oil recovery processes have been documented (Kianipey, S. A. and Donaldson, E. C. 61st Annual Technical Conference and Exhibition, New Orleans, La., USA, Oct. 5-8, 1986).

Microbial Enhanced Oil Recovery (MEOR) is a methodology for increasing oil recovery by the action of microorganisms (Brown, L. R., et al., SPE 59306, SPE/DOE Improved Oil Recovery Symposium, Oklahoma, Apr. 3-5, 2000). MEOR research and development is an ongoing effort directed at discovering techniques to use microorganisms to modify crude oil properties to benefit oil recovery (Sunde. E., et al., SPE 24204, SPE/DOE $8^{th}$ Symposium on enhanced Oil Recovery, Tulsa, Okla., USA, Apr. 22-24, 1992). In MEOR processes, useful microbes are typically hydrocarbon-utilizing, non-pathogenic microorganisms, which use hydrocarbons as their source of energy to grow or excrete natural bio-products such as alcohols, gases, acids, surfactants and polymers. These bio-products change the physio/chemical properties of the crude oil and stimulate changes in the oil-water-rock interactions to improve oil recovery.

Remediation of hydrocarbon-contaminated sites is difficult due to the structural properties of the crude oil. Crude oil is characterized by apolar C—C and C—H bonds and lacks functional chemical groups that contribute to the crude oil's recalcitrant nature. Crude oil consists of alkanes, alkenes, alkynes, aromatic polycyclic hydrocarbons, asphaltenes and resins. Conventional methods used to remediate hydrocarbons include solvent treatment and polymeric particles having covalently bound to a polymeric component as described in U.S. Pat. No. 7,449,429B2, U.S. Pat. No. 6,852,234B2, U.S. Pat. No. 7,465,395, U.S. Pat. No. 7,201,804B2, U.S. Pat. No. 7,473,672B2, U.S. Pat. No. 7,442,313B2; site excavation as practiced by Ground Remediation Systems, LTD, UK; and pump and treat, which involves pumping out contaminated groundwater with the use of a submersible or vacuum pump The extracted groundwater is then purified by slowly proceeding through a series of vessels that contain materials designed to adsorb the contaminants from the groundwater and vacuum extraction (U.S. Pat. No. 7,172,688B2). These processes are costly, time consuming and leave undesirable environmental footprints.

Alternatively, microorganisms may be used for in situ bioremediation of hydrocarbon-contaminated sites. For example, biodegradation of contaminants by indigenous microbial populations is common in many aerobic environments (Gibson, D. T., Microbial Degradation of Organic Compounds, 1984, Marcel Dekker, NY). Addition of oxygen and nutrients to stimulate the growth of indigenous microorganisms can be an effective bioremediation tool in the cleanup of crude oil spill. An alternative approach, reported for soils contaminated with crude oil or petroleum hydrocarbons, is the introduction into the soils of microbes capable of degrading these chemicals. These processes rely on oxidative degradation under aerobic conditions, and the microbes use the hydrocarbon contaminant as the carbon and energy source (U.S. Pat. No. 6,652,752B2). However, in many cases aerobic bioremediation is impractical because of the anoxic nature of the natural environments of the hydrocarbon-contaminated sites, such as soil, groundwater aquifers, fresh water and marine sediments and oil reservoirs.

Since application of microorganisms for MEOR and in-situ bioremediation is a promising alternative to traditional oil recovery or in situ remediation means, developing methods for identifying microorganisms useful in these processes, which would allow cost-effective processes for MEOR and bioremediation, is important. Previously described methods for such applications, for example, include obtaining the sample under specific conditions with a defined nutrient medium in the presence of anaerobic gas mixtures (U.S. Patent Application No. 2007/0092930A1). A process for stimulating the in situ activity of a microbial consortium to produce methane for oil was described (U.S. Pat. No. 6,543,535B2). However, such processes are time consuming, labor-intensive and therefore costly.

Thus, there is a need for developing methods to: 1) obtain a steady state population of consortium of microorganisms that can grow in or on oil under anaerobic denitrifying conditions; 2) identify the members of the steady state consortium for properties that might be useful in oil modification and/or degradation and 3) use said steady state consortium of microorganisms, in a cost-effective way, for enhanced oil recovery from wells or reservoirs or in situ bioremediation of hydrocarbon-contaminated sites.

SUMMARY ON THE INVENTION

Enriched steady state microbial consortiums for microbial enhanced oil recovery and in situ bioremediation of hydrocarbon-contaminated sites, under anaerobic denitrifying conditions, are disclosed. The consortium is identified by obtaining environmental samples comprising indigenous microbial populations exposed to crude oil and enriching said populations per an enrichment protocol. The enrichment protocol employs a chemostat bioreactor to provide a steady state population. The steady state population may be characterized by using phylogenetic DNA sequence analysis techniques, which include 16S rDNA profiling and/or DGGE fingerprint profiling as described herein. The steady state population is further characterized as an enriched consortium comprising microbial constituents having relevant functionalities for improving oil recovery or in situ bioremediation of hydrocarbon-contaminated environmental sites. The steady state enriched consortium may grow in situ, under reservoir conditions, using one or more electron acceptors and the reservoir's crude oil as the carbon source for microbial enhancement of oil recovery or in situ bioremediation of hydrocarbon-contaminated environmental sites. The steady state consortium may be used with other microorganisms to enhance oil recovery in reservoirs or wells or in situ bioremediation of hydrocarbon-contaminated environmental sites with analogous reservoir conditions of the selected/targeted wells.

In one aspect, a method for in situ bioremediation of hydrocarbon-contaminated environmental sites or enhancing oil recovery from an oil reservoir using an enriched steady state microbial consortium is provided, said method comprising:
   a. at least one first species of the genus *Thauera* having a 16S rDNA nucleic acid molecule having the nucleic acid sequence that has at least 95% identity to SEQ ID NO: 15;
   b. at least one second species having 16S rDNA nucleic acid molecule having the nucleic acid sequence that has at least 95% identity to a sequence selected from the group consisting of SEQ ID NOs:16, 19, 21, 23, 24-28, 30-41, 67 and 68; and
   c. at least one third species having 16S rDNA nucleic acid molecule having the nucleic acid sequence that has at least 95% identity to a sequence selected from the group consisting of SEQ ID NOs: 17, 18, 20, 22, 29, 54, 69 and 86 and combinations thereof is provided.

In another aspect, a composition for enhancing oil recovery or for in situ bioremediation comprising: an isolated consortium of microbial species, comprising at least one *Thauera* strain and at least two other strains selected from the group consisting of *Azoarcus* species, *Pseudomonas* species, *Azotobacter* species, *Bacteroides* species, *Clostridium* species, *Anaerovorax* species, *Finegoldia* species, *Spirochetes* species, *Deferribacter* species, *Flexistipes* species, *Chloroflexi* species and *Ochrobactrum* species is provided.

BRIEF DESCRIPTION OF FIGURES OF THE INVENTION

FIG. 1: Distribution of microorganisms in the parent POG1 consortium after three months in second-generation parent populations as determined by 16S rDNA identities.

Figure 2A:
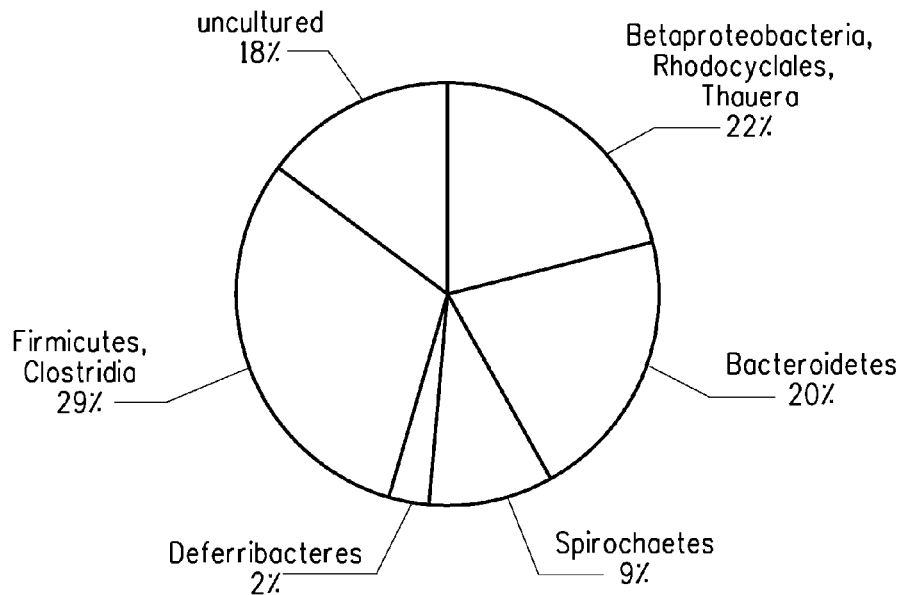
Figure 2B:
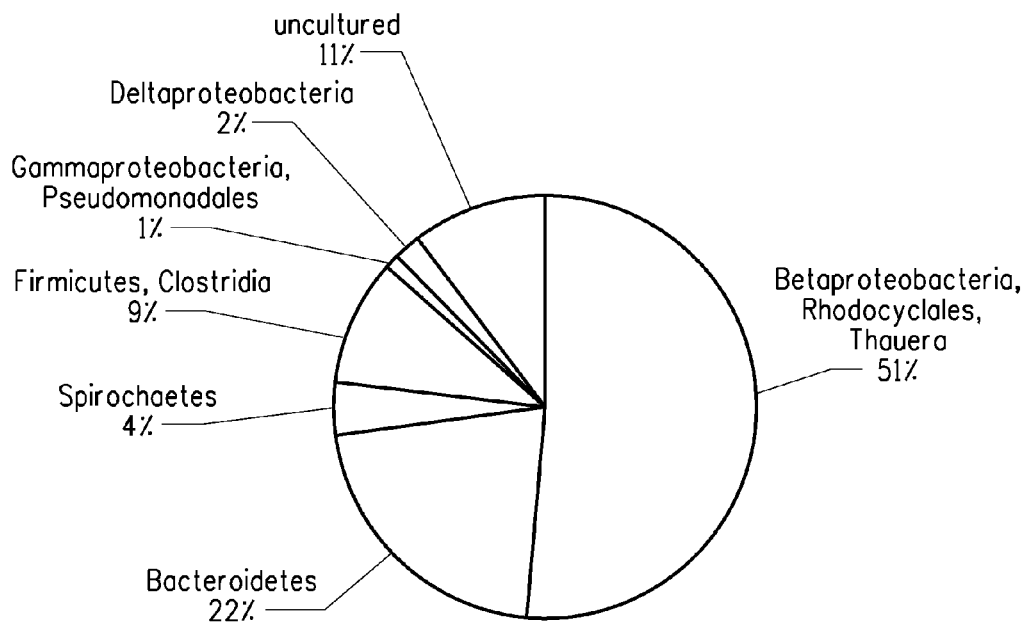

FIGS. 2A and 2B: Distribution of microorganisms in the parent POG1 consortium after 190 days in second- and third-generation parent populations determined by 16S rDNA identities. FIG. 2A: Population distribution of third-generation parent at 190 days while 6400 ppm Nitrate had been reduced. FIG. 2B: Population distribution of second-generation parent at 240 days while 6400 ppm Nitrate had been reduced FIG. 3: Diagram of the anaerobic chemostat bioreactor for denitrifying growth studies with the steady state POG1 consortium: A) Reverse flow bubbler; B) Nitrogen manifold; C) Feed sampling syringe and relief valve (5 psi); D) Feed syringe pump; E) Feed reservoir head space nitrogen gas port; F) Feed input port on chemostat bioreactor; G) Feed medium reservoir (minimal and nitrate); H) Chemostat Bioreactor; I) Minimal salt medium and consortium culture; J) Magnetic stirrer; K) Crude oil supplement; L) Effluent reservoir; M) Effluent exit port on chemostat bioreactor; N) Effluent reservoir head space nitrogen gas port; O) Effluent syringe port; P) Effluent sampling syringe and relief valve (5 psi); Q) Inoculation and sampling port on chemostat bioreactor; R) Extra port and plug; S) Chemostat bioreactor head space nitrogen gas port.

Figure 4:
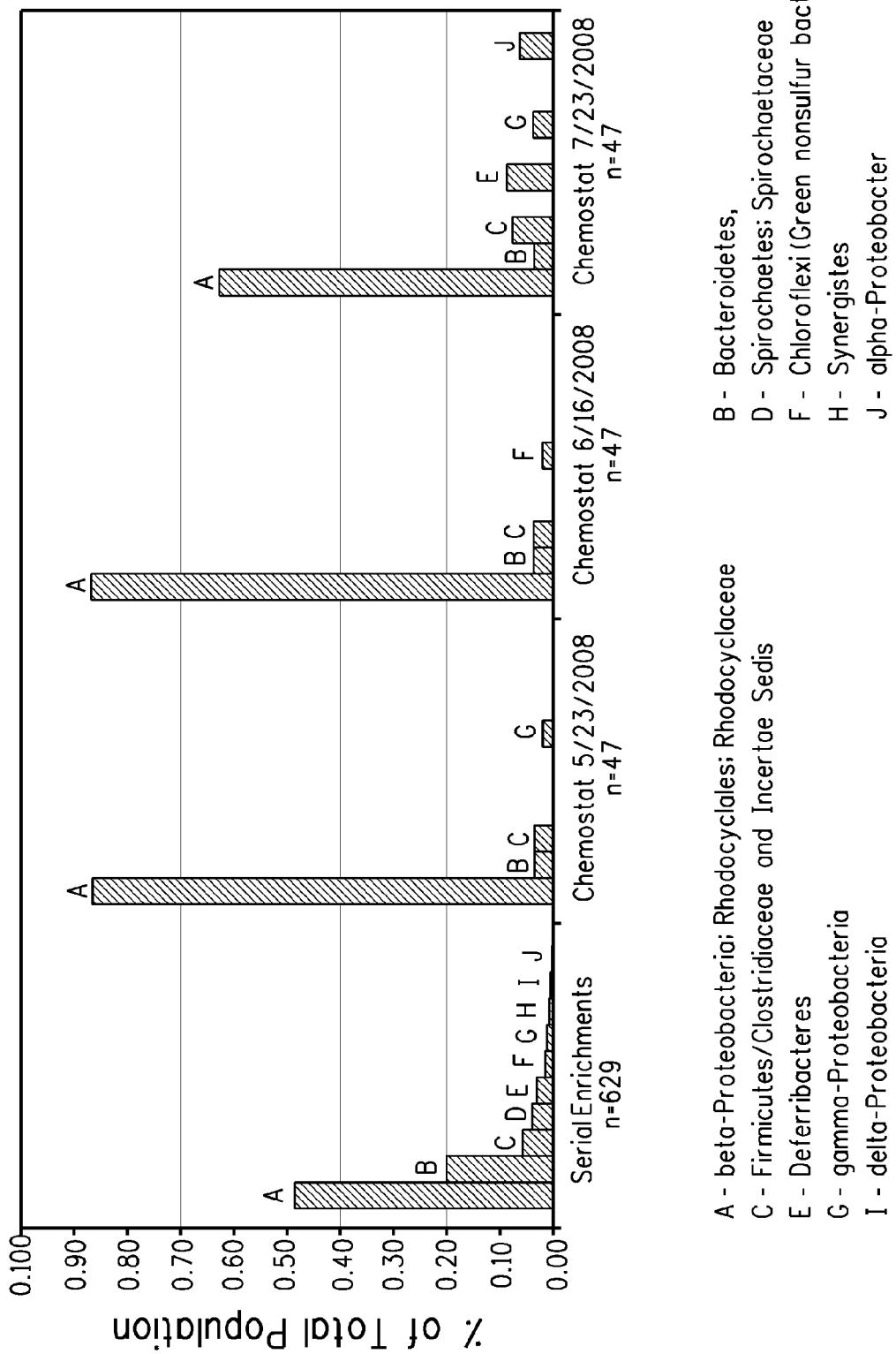

FIG. 4: Distribution of microorganisms in the steady state POG1 as determined by 16S rDNA identities. Consortium constituents at 0, 28 and 52 day, were compared to the parent populations.

Figure 5:
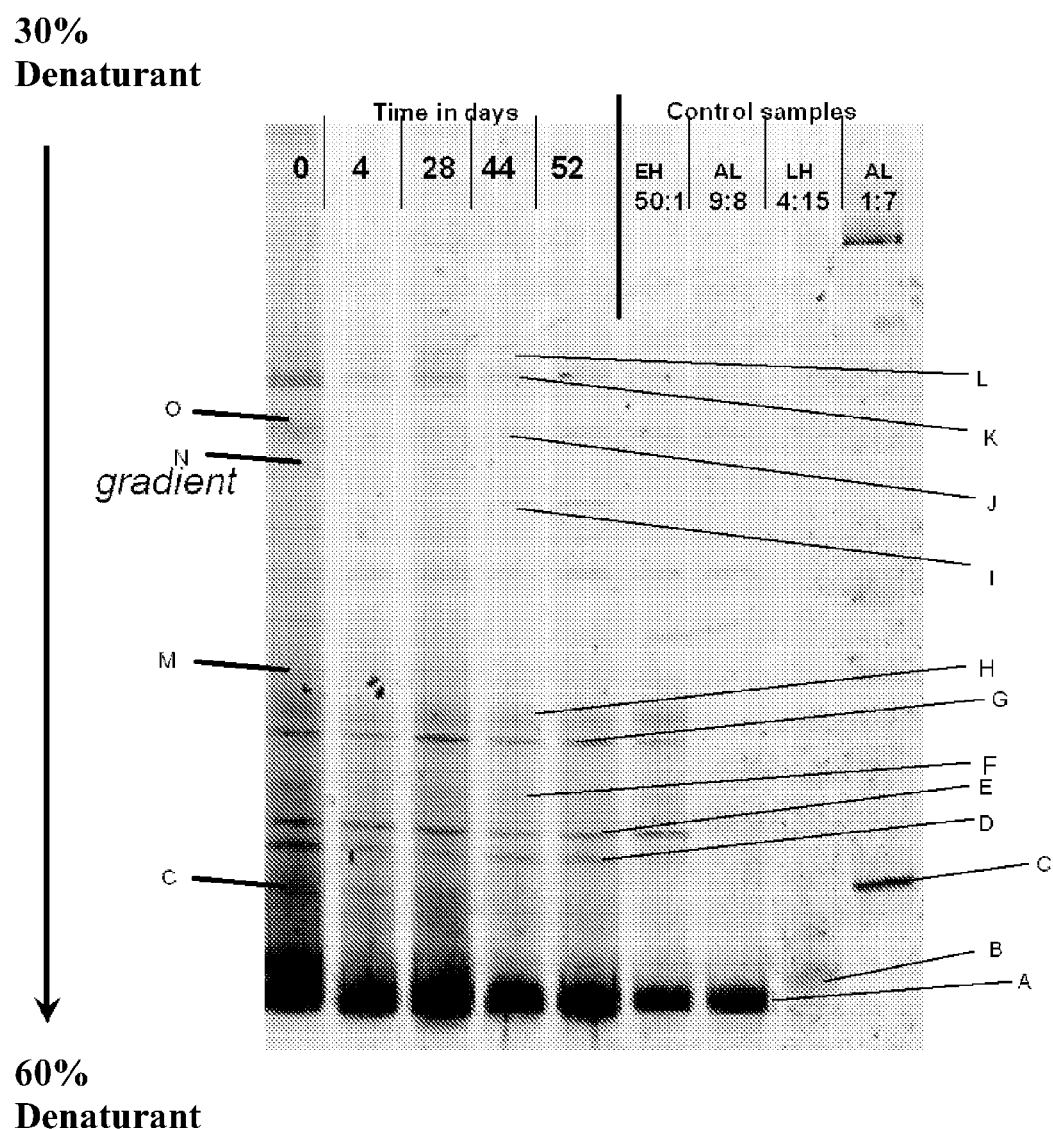

FIG. 5: Denaturing gradient gel electrophoresis fingerprint profile of the bacterial 16S rRNA gene fragments derived from community DNA extracted from the steady state POG1 chemostat bioreactor using primers SEQ ID NO: 12 and SEQ ID NO: 14 for region V4-5. (A) *Thauera* strain AL9:8 is a prominent species of a consortium as described herein. (B) *Pseudomonas stutzeri* LH4:15 is also a represented species of the consortium. (C) *Ochrobactrum oryzae* AL1:7 is the minor species. Minor bacterial species (D through L) are present in all samples. Bacterial species (C & M through O) are less important members of population and are selected against.

Figure 6:
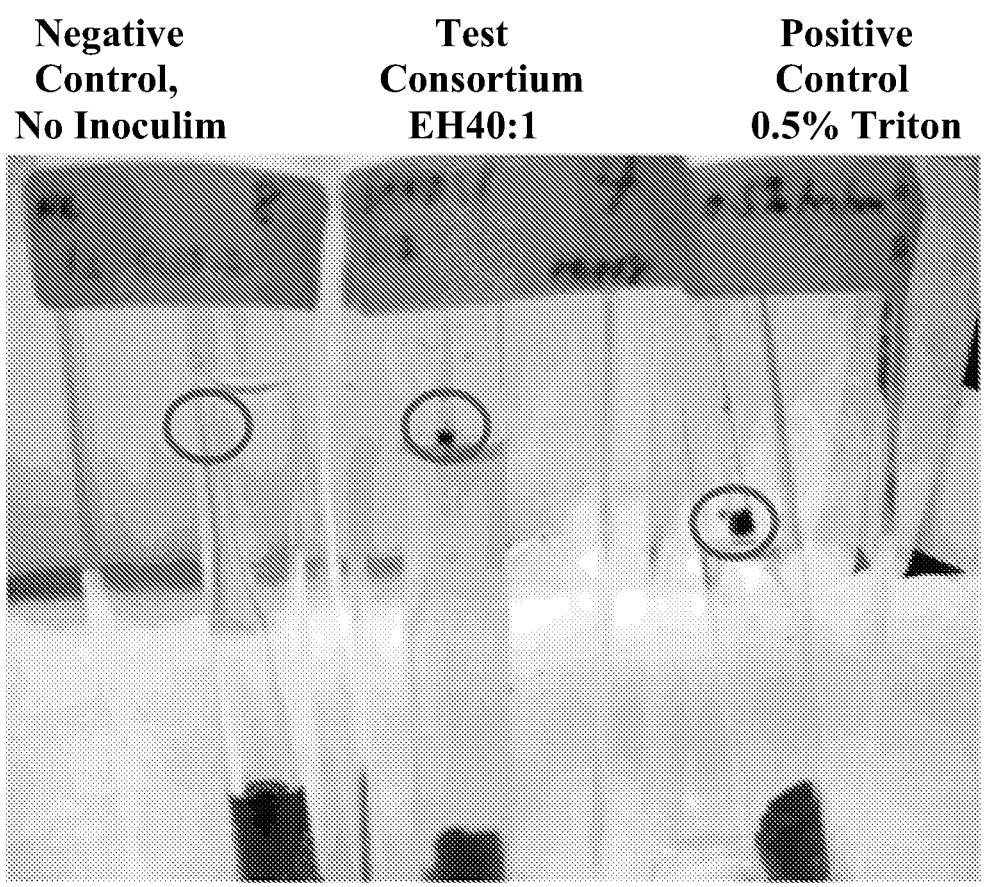

FIG. 6: Microsand column oil release—Using oil on North Slope sand, the $3^{rd}$ generation parent POG1 consortium culture EH40:1 (2400 ppm Nitrate).

The following sequences conform to 37 C.F.R. §1.821-1.825 ("Requirements for patent applications Containing Nucleotide Sequences and/or Amino Acid Sequence Disclosures—the Sequence Rules") and are consistent with the World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions. The symbols and format used for nucleotide and amino acid sequence data comply with the rules set forth in 37 C.F.R. §1.822.

TABLE 1

PRIMER SEQUENCES USED IN THIS INVENTION

| Description | SEQ ID NO: Nucleic acid |
|---|---|
| 8F<br>Bacterial 16S rDNA forward universal primer | 1 |
| 1492 R<br>Bacterial 16S rDNA reverse universal primer | 2 |
| 1407 R<br>Bacterial 16rDNA reverse universal primer | 3 |
| U518R,<br>16S rDNA universal reverse primer | 4 |
| UB 357F<br>Bacterial 16S rDNA forward universal primer | 5 |
| dG•UB 357F<br>DGGE Bacterial 16S rDNA universal forward primer with 5' 40-bp GC-rich clamp | 6 |
| UA 341F1<br>Archaeal 16S rDNA universal forward primer | 7 |
| dG•UA 341F1<br>DGGE Archaeal 16S rDNA universal forward primer with 5' 40-bp GC-rich clamp | 8 |
| UA 341F2<br>Archaeal 16S rDNA universal forward primer | 9 |
| dG•UA 341F2<br>DGGE Archaeal rDNA universal forward 16S primer with 5' 40-bp GC-rich clamp | 10 |
| U 519F<br>Universal 16S rDNA forward primer | 11 |
| dG•U 519F<br>DGGE Universal 16S rDNA forward primer with 5' 40-bp GC-rich clamp | 12 |
| UA958R,<br>Archaeal universal 16S rDNA reverse primer | 13 |

TABLE 1-continued

PRIMER SEQUENCES USED IN THIS INVENTION

| Description | SEQ ID NO: Nucleic acid |
|---|---|
| UB 939R, Bacterial 16S rRNA universal reverse primer | 14 |

The following DNA sequences were consensus sequences of unique cloned PCR sequences, which were generated using universal 16S primers with DNA isolated from whole POG1 community:

SEQ ID NO: 15 is the consensus DNA sequence, clones ID: 1A: *Thauera* sp AL9:8
SEQ ID NO: 16 is the consensus DNA sequence, clones ID: 1B: *Thauera* sp R26885
SEQ ID NO: 17 is the consensus DNA sequence, clones ID: 1C: *Azoarcus* sp mXyN1
SEQ ID NO: 18 is the consensus DNA sequence, clones IDI: *Azoarcus* sp mXyN1
SEQ ID NO: 19 is the consensus DNA sequence, clones ID: 1E: *Thauera* sp R26885
SEQ ID NO: 20 is the consensus DNA sequence, clones ID: 1F: *Azotobacter beijerinckii*
SEQ ID NO: 21 is the consensus DNA sequence, clones ID: 1G: *Thauera* sp R26885
SEQ ID NO: 22 is the consensus DNA sequence, clones ID: 1H: *Azoarcus* sp mXyN1
SEQ ID NO: 23 is the consensus DNA sequence, clones ID: 1I: *Thauera aromatica*
SEQ ID NO: 24 is the consensus DNA sequence, clones ID: 1J: *Thauera aromatica*
SEQ ID NO: 25 is the consensus DNA sequence, clones ID: 1: *Thauera aromatica*
SEQ ID NO: 26 is the consensus DNA sequence, clones ID: 1L: *Thauera aromatica*
SEQ ID NO: 27 is the consensus DNA sequence, clones ID: 1M: *Thauera aromatica*
SEQ ID NO: 28 is the consensus DNA sequence, clones ID: 1N: *Thauera aromatica*
SEQ ID NO: 29 is the consensus DNA sequence, clones ID: 1O: *Azoarcus* sp. EH10
SEQ ID NO: 30 is the consensus DNA sequence, clones ID: 1P: *Thauera* sp R26885
SEQ ID NO: 31 is the consensus DNA sequence, clones ID: 1Q: *Thauera aromatica*
SEQ ID NO: 32 is the consensus DNA sequence, clones ID: 1R: *Thauera aromatica*
SEQ ID NO: 33 is the consensus DNA sequence, clones ID: 1S: *Thauera aromatica*
SEQ ID NO: 34 is the consensus DNA sequence, clones ID: 1T: *Thauera aromatica*
SEQ ID NO: 35 is the consensus DNA sequence, clones ID: 1U: *Thauera aromatica*
SEQ ID NO: 36 is the consensus DNA sequence, clones ID: 1V: *Thauera aromatica*
SEQ ID NO: 37 is the consensus DNA sequence, clones ID: 1W: *Thauera aromatica*
SEQ ID NO: 38 is the consensus DNA sequence, clones ID: 1X: *Thauera aromatica*
SEQ ID NO: 39 is the consensus DNA sequence, clones ID: 1Y: *Thauera aromatica*
SEQ ID NO: 40 is the consensus DNA sequence, clones ID: 1Z: *Thauera aromatica*
SEQ ID NO: 41 is the consensus DNA sequence, clones ID: 1AZ: *Thauera aromatica*
SEQ ID NO: 42 is the consensus DNA sequence, clones ID: 2: *Finegoldia magna*
SEQ ID NO: 43 is the consensus DNA sequence, clones ID: 3 *Spirochaeta* sp MET-E
SEQ ID NO: 44 is the consensus DNA sequence, clones ID: 4: *Azotobacter beijerinckii*
SEQ ID NO: 45 is the consensus DNA sequence, clones ID: *Finegoldia magna*
SEQ ID NO: 46 is the consensus DNA sequence, clones ID: 6: *Azotobacter beijerinckii*
SEQ ID NO: 47 is the consensus DNA sequence, clones ID: 7: *Ochrobactrum* sp mp-5
SEQ ID NO: 48 is the consensus DNA sequence, clones ID: 8A: *Anaerovorax* sp. EH8A
SEQ ID NO: 49 is the consensus DNA sequence, clones ID: 8B: *Anaerovorax* sp. EH8B
SEQ ID NO: 50 is the consensus DNA sequence, clones ID: 9A: *Finegoldia magna*
SEQ ID NO: 51 is the consensus DNA sequence, clones ID: 9B: *Finegoldia magna*
SEQ ID NO: 52 is the consensus DNA sequence, clones ID: 9C: *Finegoldia magna*
SEQ ID NO: 53 is the consensus DNA sequence, clones ID: 10: *Flexistipes* sp vp180
SEQ ID NO: 54 is the consensus DNA sequence, clones ID: 11: *Azoarcus* sp._EH11
SEQ ID NO: 55 is the consensus DNA sequence, clones ID: 12: *Clostridium chartatabidium*
SEQ ID NO: 56 is the consensus DNA sequence, clones ID: 13: *Deferribacter desulfuricans*
SEQ ID NO: 57 is the consensus DNA sequence, clones ID: 14A: *Azotobacter beijerinckii*
SEQ ID NO: 58 is the consensus DNA sequence, clones ID: 14B: *Flexistipes* sp vp180
SEQ ID NO: 59 is the consensus DNA sequence, clones ID: 15: *Ochrobactrum lupini*
SEQ ID NO: 60 is the consensus DNA sequence, clones ID: 16A: *Pseudomonas pseudoalcligenes*
SEQ ID NO: 61 is the consensus DNA sequence, clones ID: 16B: *Pseudomonas putida*
SEQ ID NO: 62 is the consensus DNA sequence, clones ID: 17A: *Pseudomonas pseudoalcligenes*
SEQ ID NO: 63 is the consensus DNA sequence, clones ID: 17B: *Clostridium chartatabidium*
SEQ ID NO: 64 is the consensus DNA sequence, clones ID: 18A: *Finegoldia magna*
SEQ ID NO: 65 is the consensus DNA sequence, clones ID: 18B: *Finegoldia magna*
SEQ ID NO: 66 is the consensus DNA sequence, clones ID: 18C: *Finegoldia magna*
SEQ ID NO: 67 is the consensus DNA sequence, clones ID: 19: *Thauera aromatica*
SEQ ID NO: 68 is the consensus DNA sequence, clones ID: 20: *Thauera aromatica*
SEQ ID NO: 69 is the consensus DNA sequence, clones ID: 21: *Azoarcus* sp. EH21
SEQ ID NO: 70 is the consensus DNA sequence, clones ID: 22: *Azotobacter beijerinckii*
SEQ ID NO: 71 is the consensus DNA sequence, clones ID: 23: *Azotobacter beijerinckii*
SEQ ID NO: 72 is the consensus DNA sequence, clones ID: 24: *Azotobacter beijerinckii*
SEQ ID NO: 73 is the consensus DNA sequence, clones ID: 25: *Azotobacter beijerinckii*
SEQ ID NO: 74 is the consensus DNA sequence, clones ID: 26: *Azotobacter beijerinckii*

SEQ ID NO: 75 is the consensus DNA sequence, clones ID: 27: *Clostridium chartatabidium*
SEQ ID NO: 76 is the consensus DNA sequence, clones ID: 28: *Clostridium aceticum*
SEQ ID NO: 77 is the consensus DNA sequence, clones ID: 29: *Deferribacter desulfuricans*
SEQ ID NO: 78 is the consensus DNA sequence, clones ID: 30: *Bacteroides* sp. EH30
SEQ ID NO: 79 is the consensus DNA sequence, clones ID: 31: *Finegoldia magna*
SEQ ID NO: 80 is the consensus DNA sequence, clones ID: 32: *Pseudomonas putida*
SEQ ID NO: 81 is the consensus DNA sequence, clones ID: 33: *Clostridium aceticum*
SEQ ID NO: 82 is the consensus DNA sequence, clones ID: 34: *Anaerovorax* sp. EH34
SEQ ID NO: 83 is the consensus DNA sequence, clones ID: 35: *Pseudomonas putida*
SEQ ID NO: 84 is the consensus DNA sequence, clones ID: 36: *Azotobacter beijerinckii*
SEQ ID NO: 85 is the consensus DNA sequence, clones ID: 37: *Azotobacter beijerinckii*
SEQ ID NO: 86 is the consensus DNA sequence, clones ID: 38: *Azoarcus* sp. EH36
SEQ ID NO: 87 is the consensus DNA sequence, clones ID: 39: *Flexistipes* sp vp180

DETAILED DESCRIPTION OF THE INVENTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The components of, means, methods and procedures for providing an enriched steady state consortium having one or more relevant functionality to enhance the release and recovery of oil from a petroleum reservoir or in situ bioremediation of hydrocarbon-contaminated sites are disclosed.

The following definitions are provided for the terms and abbreviations used in this application:

The term "environmental sample" means any substance exposed to hydrocarbons of the contaminated site, including a mixture of water, soil and oil comprising microorganisms. As used herein, environmental samples include water, soil and oil samples that comprise indigenous microorganisms and/or populations of microorganisms of varying genus and species that may be characterized by 16S rDNA profiling or DNA fingerprinting techniques as described in detail below. The environmental samples may comprise a microbial consortium unique to a geographic region or the target hydrocarbon-contaminated site, or, alternatively the microbial consortium may be adaptable to other environmental sites, geographies and reservoirs.

The term "enriching for one or more steady state consortium" as used herein means that an environmental sample may be enriched in accordance with the invention by culturing the sample in a chemostat bioreactor under desired conditions such as anaerobic denitrifying conditions using a basic minimal medium, such as SL-10 as described in Table 2, and a sample of the target oil or its components or a soil or water sample from the hydrocarbon-contaminated site as a carbon source.

The term "core flood assay" refers to water-flooding the core of an oil reservoir after application of an oil recovery technique, i.e., a MEOR technology, to the reservoir. An increase in oil release represents the ability of applied microbes to aid in the release of oil from the core matrix.

The term "hydrocarbon-contaminated site" as used herein means an environmental site that has received heavy spills of either crude oil or other mixtures of various aliphatic, aromatic and asphaltene hydrocarbons.

The term "bioremediation of hydrocarbon-contaminated site" as used herein means degradation of the hydrocarbons that have contaminated the site through action of the microbial constituents of the steady state consortium.

The term "components of the POG1 consortium" refers to members or microbial constituents (both major and minor) of the POG1 consortium. These may be indigenous to the consortium or may be added strains. Additional components such as electron acceptors and combination of electron acceptors could be present too.

The terms "steady state consortium" and "enriched steady state microbial consortium" refers to a mixed culture of microorganisms and/or microbial populations grown in a chemostat bioreactor and in a medium under specific growth conditions to enrich for growth of particular populations of microorganisms, and once enriched, to reach a stable condition such that the consortium does significantly change over time under a given set of conditions. The steady state is controlled by a limiting nutrient. In an embodiment the steady state consortium is provided by enriching the microorganisms in a defined minimal, denitrifying medium, under anaerobic denitrifying conditions, using crude oil or a hydrocarbon-contaminated environmental sample as the carbon source, until the population has reached its steady state. In the present case the electron acceptor, nitrate, is limiting and is fed at a constant flow. The consortium may comprise microbial populations from environmental samples or from pure or mixed non-indigenous cultures.

The term "POG1 consortium" as used herein refers to a consortium derived from a hydrocarbon-contaminated environmental enrichment that was obtained from a soil sample contaminated with polycyclic aromatic hydrocarbons.

The term "crude oil" refers to a naturally occurring, flammable liquid found in rock formations and comprises a complex mixture of hydrocarbons of various molecular weights, plus other organic compounds. The crude oil may contain, for example, a mixture of paraffins, aromatics, asphaltenes, aliphatic, aromatic, cyclic, polycyclic and polyaromatic hydrocarbons. The crude oil may be generic or may be from a reservoir targeted for enhanced oil recovery, or from a hydrocarbon-contaminated environmental site targeted for in situ bioremediation.

The term "electron acceptor" refers to a molecule or compound that receives or accepts an electron during cellular respiration.

The terms "denitrifying" and "denitrification" mean reducing nitrate for use as an electron acceptor in respiratory energy generation.

The term "nitrates" and "nitrites" refers to any salt of nitrate ($NO_3$) or nitrite ($NO_2$).

The term "relevant functionalities" means that the consortium has the ability to function in ways that promotes oil recovery or in situ bioremediation. Certain such functionalities include:

(a) alteration of the permeability of the subterranean formation for improved water sweep efficiency;

(b) modification of the hydrocarbon components of the contaminated site (c) production of biosurfactants to decrease surface and interfacial tensions;

(d) change in wettability;

(e) production of polymers other than surfactants that facilitate mobility of petroleum or availability of hydrocarbons;

(f) production of low molecular weight acids which cause rock dissolution;

(g) generation of gases to increase formation pressure;

(h) reduction in oil viscosity; and (i) degradation of oil hydrocarbons or hydrocarbon components.

The ability to demonstrate such functionalities in the present invention is dependent upon the consortium's ability to (1) grow under anaerobic conditions while reducing nitrates or nitrites; (2) use at least one component available in the oil well or hydrocarbon-contaminated site as a carbon source; (3) use at least one component in the injected or produced water; (4) grow in the presence of oil; (5) grow optimally in the oil well or in the hydrocarbon-contaminated environment; and (6) achieve combinations of the above.

The term "modifying the environment of oil reservoir" includes the ability of the enriched steady state microbial consortium to affect an oil bearing formation in the following ways (per the relevant functionalities) 1) alter the permeability of the subterranean formation (sweep efficiency), (2) produce biosurfactants which decrease surface and interfacial tensions, (3) mediate changes in wettability, (4) produce polymers, which facilitate mobility of petroleum or availability of hydrocarbons; and (5) generate gases (predominantly $CO_2$) that increase formation pressure; and (6) reduce oil viscosity.

The terms "well" and "reservoir" may be used herein interchangeably and refer to a subterranean or seabed formation from which oil may be recovered. The terms well and reservoir include the physical/chemical composition of the soil-rock-sediment structure of the reservoir below the surface.

The terms "target oil reservoir" and "target reservoir" may be used herein interchangeably and refer to a subterranean or seabed formation from which enhanced oil recovery is desired and to which the enriched steady state microbial consortium may be applied.

The term "growing on oil" means the microbial species capable of metabolizing aliphatic, aromatic and polycyclic aromatic hydrocarbons or any other organic components of the crude petroleum as a nutrient to support growth. The ability to grow on oil according to an embodiment of the invention eliminates the need for supplying certain nutrients, such as additional carbon sources, for using the microbial consortium for improved oil recovery or for in situ bioremediation of the hydrocarbon-contaminated site.

The term "chemostat bioreactor" refers to a bioreactor used for a continuous flow culture to maintain microbial populations or a consortium of microorganism in a steady state growth phase. This is accomplished by regulating a continuous supply of medium to the microbes, which maintains the electron donor or electron receptor in limited quantities in order to control the growth rate of the culture.

The term "fingerprint profile" refers to the process of generating a specific pattern of DNA bands on a denaturing gradient electrophoresis gel that are defined by their length and sequence and is used to identify and describe the predominant microbial population of a culture assessing microbial diversity and population stability at any particular metabolic state.

The term "promotes in situ bioremediation" as used herein means growing the microbial consortium in the contaminated site under anaerobic conditions to provide for modification of the oil in the site as defined above by a relevant functionality which may result in a change in the oil content of the hydrocarbon-contaminated site. Such changes support release of oil or its components from sand or soil to enhance bioremediation of the hydrocarbon-contaminated site.

The term "rDNA typing" or "rDNA profiling" means the process of comparing the 16S rDNA gene sequences found in the experimental samples to rDNA sequences maintained in several international databases to identify, by sequence homology, the "closest relative" of microbial species.

The term "signature sequences" herein will refer to unique sequences of nucleotides in the 16S rRNA gene sequence that can be used specifically to phylogenetically define an organism or group of organisms. These sequences are used to distinguish the origin of the sequence from an organism at the kingdom, domain, phylum, class, order, genus, family, species and even an isolate at the phylogenic level of classification.

The term "structural domain" herein refers to specific sequence regions in the 16S rRNA gene sequence that when aligned reveal a pattern in which relatively conserved stretches of primary sequence and a secondary sequence alternate with variable regions that differ remarkably in sequence length, base composition and potential secondary structure. These structural domains of 16S rRNA gene sequence are divided into three categories: the universally conserved or "U" regions, semi conserved or "S" regions and the variable or "V" regions. All of the structural domains contain signature sequence regions that phylogenetically define a microorganism. (Neefs, J-M et al., Nucleic acids Res., 18: 2237, 1990, Botter, E. C., ASM News 1996).

The term "phylogenetics" refers to the study of evolutionary relatedness among various groups of organisms (e.g., bacterial or archaeal species or populations).

The term "phylogenetic typing", "phylogenetic mapping" or "phylogenetic classification" may be used interchangeably herein and refer to a form of classification in which microorganisms are grouped according to their ancestral lineage. The methods herein are specifically directed to phylogenetic typing on environmental samples based on 16S ribosomal DNA (rDNA) sequencing. In this context, approximately 1400 base pair (bp) length of the 16S rDNA gene sequence is generated using 16S rDNA universal primers identified herein and compared by sequence homology to a database of microbial rDNA sequences. This comparison is then used to help taxonomically classify pure cultures for use in enhanced oil recovery.

The abbreviation "DNA" refers to deoxyribonucleic acid.

"Gene" is a specific unit on a DNA molecule that is composed of a nucleotide sequence that encodes a distinct genetic message for regulatory regions, transcribed structural regions or functional regions.

The abbreviation "rDNA" refers to ribosomal operon or gene sequences encoding ribosomal RNA on the genomic DNA sequence.

The abbreviation "NTPs" refers to ribonucleotide triphosphates, which are the chemical building blocks or "genetic letters" for RNA.

The abbreviation "dNTPs" refers to deoxyribonucleotide triphosphates, which are the chemical building blocks or "genetic letters" for DNA.

The term "rRNA" refers to ribosomal structural RNA, which includes the 5S, 16 S and 23S rRNA molecules. The term "rRNA operon" refers to an operon that produces structural RNA, which includes the 5S, 16 S and 23S ribosomal structural RNA molecules.

The term "mRNA" refers to an RNA molecule that has been transcribed from a gene coded on a DNA template and carries the genetic information for a protein to the ribosomes to be translated and synthesized into the protein.

The term "hybridize" is used to describe the formation base pairs between complementary regions of two strands of DNA that were not originally paired.

The term "complementary" is used to describe the relationship between nucleotide bases that are capable of hybridizing to one another. For example, with respect to DNA, adenosine is complementary to thymine and cytosine is complementary to guanine.

The abbreviation "cDNA" refers to DNA that is complementary to and is derived from either messenger RNA or rRNA.

The abbreviation "NCBI" refers to the National Center for Biotechnology Information.

The term "GenBank" refers to the National Institute of Health's genetic sequence database.

The term "nutrient supplementation" refers to the addition of nutrients that benefit the growth of microorganisms that are capable of using crude oil as their main carbon source but grow optimally with other non-hydrocarbon nutrients, i.e., yeast extract, peptone, succinate, lactate, formate, acetate, propionate, glutamate, glycine, lysine, citrate, glucose, and vitamin solutions.

The abbreviation "NIC" refers to non-inoculum, negative controls in microbial culture experiments.

The abbreviation "ACO" (autoclaved crude oil) refers to crude oil that has been steam sterilized using an autoclave, and is assumed to be devoid of living microbes.

The term "bacterial" means belonging to the bacteria—Bacteria are an evolutionary domain or kingdom of microbial species separate from other prokaryotes based on their physiology, morphology and 16S rDNA sequence homologies.

The term "microbial species" means distinct microorganisms identified based on their physiology, morphology and phylogenetic characteristics using 16S rDNA sequences.

The term "archaeal" means belongings to the Archaea. Archaea are an evolutionary domain or kingdom of microbial species separate from other prokaryotes based on their physiology, morphology and 16S rDNA sequence homologies.

The term "sweep efficiency" means the ability of injected water employed in water flooding oil recovery techniques to 'push' oil through a geological formation toward a producer well.

The term "biofilm" means a film made up of a matrix of a compact mass of microorganisms consisting of structural heterogeneity, genetic diversity, complex community interactions, and an extracellular matrix of polymeric substances.

The term "irreducible water saturation" is the minimal water saturation that can be achieved in a porous core plug when flooding with oil to saturation. It represents the interstitial water content of the matrix where the water is never completely displaced by the oil because a minimal amount of water must be retained to satisfy capillary forces.

The term "ribotyping" or "riboprint" refers to fingerprinting of genomic DNA restriction fragments that contain all or part of the rRNA operon encoding for the 5S, 16S and 23S rRNA genes. Ribotyping, as described herein, is where restriction fragments, produced from microbial chromosomal DNA, are separated by electrophoresis, transferred to a filter membrane and probed with labeled rDNA operon probes. Restriction fragments that hybridize to the label probe produce a distinct labeled pattern or fingerprint/barcode that is unique to a specific microbial strain.

The ribotyping procedure can be entirely performed on the Riboprinter® instrument (DuPont Qualicon, Wilmington, Del.).

The term "percent identity", as known in the art, is a relationship between two or more polypeptide sequences or two or more polynucleotide sequences, as determined by sequence comparisons. In the art, "identity" also means the degree of sequence relatedness or homology between polynucleotide sequences, as determined by the match between strings of such sequences and their degree of invariance. The term "similarity" refers to how related one nucleotide or protein sequence is to another. The extent of similarity between two sequences is based on the percent of sequence identity and/or conservation. "Identity" and "similarity" can be readily calculated by known methods, including but not limited to those described in "Computational Molecular Biology, Lesk, A. M., ed. Oxford University Press, NY, 1988"; and "Biocomputing: Informatics and Genome Projects, Smith, D. W., ed., Academic Press, NY, 1993"; and "Computer Analysis of Sequence Data, Part I, Griffin, A. M., and Griffin, H. G., eds., Humana Press, NJ, 1994"; and "Sequence Analysis in Molecular Biology, von Heinje, G., ed., Academic Press, 1987"; and "Sequence Analysis Primer, Gribskov, M. and Devereux, J., eds., Stockton Press, NY, 1991". Preferred methods to determine identity are designed to give the best match between the sequences tested. Methods to determine identity and similarity are codified in publicly available computer programs.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wis.), BLASTP, BLASTN, BLASTX (Altschul, S. F. et al., J. Mol. Biol. 215: 403-410, 1990), DNASTAR (DNASTAR, Inc., Madison, Wis.), and the FASTA program incorporating the Smith-Waterman algorithm (Pearson, W. R., Comput. Methods Genome Res., Proc. Int. Symp, Meeting Date 1992, 111-120. eds.; Suhai, Sandor. Publisher: Plenum, New York, N.Y., 1994). Within the context of this application, it will be understood that where sequence analysis software is used for analysis, the results of the analysis will be based on the "default values" of the program referenced, unless otherwise specified. As used herein "default values" will mean any set of values or parameters that load with the software when first initialized.

The term "denaturing gradient gel electrophoresis" or "DGGE" refers to a molecular fingerprinting method that separates polymerase chain reaction-generated (PCR-generated) DNA products based on their length and sequence. The separation of the PCR product fragment of the same size, but with a different sequence reflects differential denaturing characteristics of the DNA due to their sequence variation. During DGGE, PCR products encounter increasingly higher concentrations of chemical denaturant as they migrate through a polyacrylamide gel. The rDNA PCR products are generated from the mixed microbial population being characterized. The weaker melting domains of certain double-stranded PCR sequences will begin to denature, slowing the electrophoretic migration dramatically. The different sequences of DNA (that are generated from different bacteria) will denature at different denaturant concentrations resulting in a pattern of bands that can be collectively referred to as the "community fingerprint profile". In theory, each band in a given DGGE fingerprint profile represents an individual bacterial species present in the community. Once generated, the data represents a fingerprint profile of the population at a given point in time and under certain growth conditions. The DGGE fingerprint profile can be uploaded into database to compare profiles of the consortium under prescribed growth conditions. Thus DGGE is used to generate the finger prints of a microbial community and to resolve the genetic diversity of complex microbial populations.

The present method provides for enhanced microbial oil recovery from oil reservoirs and enhanced in situ bioremediation of hydrocarbon-contaminated sites using an enriched steady state microbial consortium comprising the following steps: 1) obtaining an environmental samples comprising indigenous microbial populations; 2) developing an enriched steady state microbial consortium wherein said consortium is enriched under anaerobic denitrifying conditions, using crude oil from the target oil reservoir or hydrocarbon component samples from the specific contaminated site as the carbon source, until the population has reached its steady state; 3) developing fingerprint profiles of samples of the steady state consortium using 16S rDNA profiling methods of said samples; 4) selecting samples of the consortium comprising various microbial genera, for example, one or more *Thauera* species and other additional species selected from the group consisting of Rhodocyclaceae, Pseudomonadales, Bacteroidaceae, Clostridiaceae, Incertae Sedis, Spirochete, Spirochaetaceaes, Deferribacterales, Brucellaceae and Chloroflexaceae; 5) identifying at least one relevant functionality of the selected enriched steady state consortium for use in MEOR of oil reservoir or in situ bioremediation of the hydrocarbon-contaminated site; 6) growing the selected enriched steady state consortium having at least one relevant functionality to a concentration sufficient for oil well or hydrocarbon-contaminated site inoculation; 7) inoculating a subsurface matrix of an oil reservoir or hydrocarbon-contaminated site with said sufficient concentration of the steady state consortium and injection water or further additives comprising one or more electron acceptors wherein the consortium grows in the reservoir or environmental matrix (soil, groundwater, sandstone, rock or any combinations of all within the matrix) and wherein it promotes enhanced oil recovery or in situ bioremediation.

Environmental Samples for Development of a Microbial Consortium

The sample source used for enrichment cultures and development of a consortium for use in MEOR or in situ bioremediation may be: 1) the oil well itself in the form of: a water sample (injection, power or production water), soil from a reservoir core or from a sample of the targeted oil; 2) an environmental sample that has been exposed to crude oil or any one or combination of its components, such as paraffins, aromatics, asphaltenes, etc.; or (3) a preexisting consortium that meet the criteria for growth in the presence of the targeted oil. The sample must be in contact with or near the oil formation since sample constituents are specific to an area. Sampling near an intended location is preferred. The sample volume and the number of microbial cells per milliliter may vary from 1 mL to 5 L and from $10^5$ to $10^{10}$ cells/mL, depending upon the specific requirements of the intended application. For the purposes of this invention, the cell density in the sample may be $10^7$ cells per milliliter. To these samples, a basic mineral salt medium, which is required for microbial growth, vitamins and electron acceptors, may be added in addition to the sample of the crude oil from the desired contaminated location and the mixture may be incubated at a suitable temperature to allow development of the desired consortium with specific functionalities.

In another embodiment an environmental sample may be provided from an oil well or reservoir environment or a hydrocarbon-contaminated site located in the oil fields or contaminated sites, which include, but not limited to Texas, Alaska the industrial North Eastern and Midwestern United States, Oklahoma, California, the Gulf of Mexico, West Africa, the Middle East, India, China, North and Eastern South America, North Sea and the Old Soviet Union.

Microbial Chemostat Bioreactor

The environmental samples comprising microbial populations may be grown in a chemostat bioreactor using enrichment techniques. The enrichment conditions may include growing an environmental sample under anaerobic denitrifying conditions in bottles while limiting the concentration of electron acceptor provided during anaerobic respiration since the rate of manual feed is often too slow to keep up with reduction of nitrate. In addition, if too high a concentration of nitrate (e.g., >2500 ppm) were to be applied, it may either inhibit growth of some microbes or be toxic and kill some other species. Conversely, denitrifying bacteria stop growing when nitrate is completely reduced, hence allowing other microbial populations to dominate the composition of the consortium through reducing other trace metals, minerals and unsaturated hydrocarbons or organic molecules. Fluctuations in nitrate levels may affect changes in the microbial composition of the consortium and unduly influence the definition of the composition of the population in it. The non-limiting examples provided herein describe how to manipulate these conditions to enrich for and identify desired constituents of a steady state microbial consortium.

Chemostat bioreactors are systems for the cultivation of microbial communities or single microbial species and provide for maintaining conditions for microbial growth and populations at a steady state by controlling the volumetric feed rate of a growth dependant factor. The chemostat setup consists of a sterile fresh nutrient reservoir connected to a growth reactor. Fresh medium containing nutrients essential for cell growth is continuously pumped to the chamber from the medium reservoir. The medium contains a specific concentration of one or more growth-limiting nutrient that allows for growth of the consortium in a controlled physiological steady state. Varying the concentration of the growth-limiting nutrients will, in turn, change the steady state concentration of cells. The effluent, consisting of unused nutrients, metabolic wastes and cells, is continuously removed from the vessel, pumped from the chemostat bioreactor to the effluent reservoir and monitored for complete reduction of nitrate. To maintain constant volume, the flow of nutrients and the removal of effluent are maintained at the same rate and are controlled by synchronized syringe pumps.

Enrichment Conditions

As stated above an environmental sample may be enriched in accordance with the invention herein by culturing the sample in a chemostat bioreactor under desired conditions such as anaerobic denitrifying conditions. Additional enrichment conditions include use of a basic minimal medium, such as SL-10 as described in Table 2.

The chemostat bioreactor may be held at a room temperature that may fluctuate from about 15° C. to about 35° C.

The steady state consortium may be enriched under anaerobic, denitrifying conditions using a nitrate salt as the electron acceptor. The enrichment culture thus may include nitrate concentrations from 25 ppm to 10,000 ppm. More specifically, the nitrate concentration may be from 25 ppm to 5000 ppm. Most specifically, the nitrate concentration may be from 100 ppm to 2000 ppm.

In one embodiment an enriched steady state microbial consortium designated POG1 was developed under denitrifying conditions with a nitrate salt as the anoxic electron acceptor. Other suitable anaerobic reducing conditions would use selective electron acceptors that include, but are not limited to: iron (III), manganese (IV), sulfate, carbon dioxide, nitrite, ferric ion, sulfur, sulfate, selenate, arsenate, carbon dioxide and organic electron acceptors that include, but not limited the chloroethenes, fumarate, malate, pyruvate, acetylaldehyde, oxaloacetate and similar unsaturated hydrocarbon compounds may also be used.

The enrichment of the consortium may include a minimal growth medium supplemented with additional required nutritional supplements, e.g., vitamins and trace metals, and crude oil as the carbon source as described in details below.

This consortium may be grown at a pH from 5.0 to 10. More specifically the pH could be from 6.0 to about 9.0. Most specifically the pH could be from 6.5 to 8.5. In addition, the steady state consortium should have an $OD_{550}$ from about 0.8 to about 1.2 and should actively reduce the electron acceptor.

Characterization of Microbial Populations in the Enriched Steady State Microbial Consortium Constituents or the microbial populations of the enriched steady state consortium may be identified by molecular phylogenetic typing techniques. Identification of microbial populations in a consortium provides for selection of a consortium with certain microbial genera and species described to have relevant functionalities for enhancing oil recovery or in situ bioremediation of the hydrocarbon-contaminated sites.

In an embodiment of the invention, an enriched steady state consortium (referred to as "POG1") was developed, as described above, from a parent mixed culture, enriched from an environmental sample, using crude oil from the targeted hydrocarbon-contaminated site as the energy source. Various constituents of the consortium were characterized using fingerprint profiles of their 16S rDNA as described below, using signature regions within the variable sequence regions found in the 16S rRNA gene of microorganisms (see Muyzer, G., et al., supra). DNA sequences of the V3 region of 16S rRNA genes in a mix population were targeted and PCR amplified as described in detail below. Using this method a consortium comprising members from *Thauera*, Rhodocyclaceae, Pseudomonadales, Bacteroidaceae, Clostridiaceae, Incertae Sedis, Spirochete, Spirochaetaceaes, Deferribacterales, Brucellaceae and Chloroflexaceae were characterized (FIG. 1). The *Thauera* strain AL9:8 was the predominant microorganism in the consortium. It represented between 35 to 70% of the constituents during sampling processes. There were 73 unique sequences (SEQ ID NOs: 15-87), which were grouped into eight phylum of bacteria, which included alpha-Proteobacteria, beta-Proteobacteria, gamma-Proteobacteria, Deferribacteraceae, Spirochaetes, Bacteroidetes, *Chloroflexi* (Green sulfur bacteria) and *Firmicutes/Clostridiales*.

The phylum beta-Proteobacteria, which constitutes Gram negative and chemoautotrophic bacteria. They were represented by a large diverse group of the members of *Thauera/Azoarcus* group. There were 31 unique 16S rDNA sequences whose sequence differences occurred in the primary signature sequences of the variable regions. *Thauera* strain AL9:8 of this group was the predominant microorganism in the consortium and represented between 35 to 70% of the constituents during sampling processes and were represented in the consortium samples by (SEQ ID NOs: 15, 16, 19, 21, 23, 24-28, 30-41, 67 and 68). The *Azoarcus* species of this phylum in the steady state consortium were represented by (SEQ ID NOs: 17, 18, 20, 22, 29, 54, 69 and 86).

The phylum Firmicutes, order Clostridia, which consist of spore-forming, Gram-positive, obligate anaerobes that are mostly obligate fermenters was represented by *Clostridium* species, *Anaerovorax* species and *Finegoldia* species. In the consortium, *Firmicutes/Clostridiales* group was diverse with 16 unique sequences that include constituents from the *Clostridia*, *Anaerovorax* and *Finegoldia* genera. Further analyses using fingerprint profiling may allow assigning the DNA bands in the DGGE DNA fingerprint to some of these sequences. The *Clostridia* species in the consortium were represented by (SEQ ID NOs: 55, 63, 75, 76 and 81). The *Anaerovorax* species were characterized by (SEQ ID NO: 48, 49 and 82). The *Finegoldia* species were characterized by (SEQ ID NOs: 42, 45, 50-52, 64-66 and 79).

The phylum Deferribacteraceae are obligate, fermentative anaerobes and use nitrate and a wide variety of metal ion as electron acceptors. This phylum was represented by *Deferribacter* and *Flexistipes* species, which were represented by (SEQ ID NO: 56 and 77) and (SEQ ID NO: 56 and 77) respectively in the steady state consortium.

The phylum Spirochaetes are obligate, fermentative anaerobes that have a unique morphology. Spirochaetaceae are a tightly coiled slender and flexuous in shape and flagella are attached each pole and fold back from each pole and into the protoplasmic cylinder and remain located in the periplasm of the cell and are called endoflagella. The *Spirochaeta* species were represented by (SEQ ID NO: 43).

The phylum gamma-Proteobacteria and the Pseudomonadales order, which consists of Gram negative bacteria that are spiral or spherical or rod-shaped, usually motile by polar flagella and are facultative anaerobes that have the ability to degrade organic compounds under denitrifying conditions was represented by various *Pseudomonas* and *Azotobacter* species. The *Pseudomonas* species were represented by (SEQ ID NOs: 60-62, 80 and 83) and the *Azotobacter* species were represented by (SEQ ID NOs: 20, 44, 54, 70-74, 84 and 85) in the steady state consortium.

The phylum alpha-Proteobacteria, order Rhizobiales, family Brucellaceae was represented by *Ochrobactrum* species. They are Gram negative, rod-shaped, motile, chemoorganotrophic, facultative anaerobes. The *Ochrobactrum* species were represented by (SEA ID NOs: 47 and 59) in the steady state consortium.

The phylum Chloroflexi are filamentous anoxygenic phototrophs (formerly known as green non-sulfur) bacteria that produce energy through photosynthesis. During various stages of the enrichment of the POG1 consortium, *Chloroflexi* species were present. However, upon further enrichment of other species, they become undetectable in the steady state consortium.

The phylum Bacteroidetes, which are Gram negative rod shape, non-endospore-forming, anaerobes, and may be either motile or non-motile bacteria. The *Bacteroides* species were represented by (SEQ ID NO: 78) in the steady state consortium.

Based on these characterizations of samples of an enriched steady state microbial consortium, an embodiment of the invention includes an enriched steady state consortium comprising: *Thauera*, alpha-Proteobacteria, gamma-Proteobacteria, Deferribacteraceae, *Bacteroides/Chloroflexi* and *Firmicutes/Clostridiales* species.

In addition, the co-pending U.S. application Ser. No. 12/194,749, describes specifically, the one or more microbial cultures may be selected from the group consisting of *Marinobacterium georgiense* (ATCC#33635), *Thauera aromatica* T1 (ATCC#700265), *Thauera chlorobenzoica* (ATCC#700723), *Petrotoga miotherma* (ATCC#51224), *Shewanella putrefaciens* (ATCC#51753), *Thauera aromatica* S100 (ATCC#700265), *Comamonas terrigena* (ATCC#14635), *Microbulbifer hydrolyticus* (ATCC#700072), and mixtures thereof, having relevant functionalities for enhanced oil recovery or in situ bioremediation.

Comparing the components of an enriched steady state consortium to the phylogeny of known microorganisms having the ability to enhance oil recovery or bioremediate hydrocarbon-contaminated sites provides a mechanism for selecting a consortium useful for these processes. Further, such known microorganisms may be added to a steady state consortium to further enhance oil recovery or in situ bioremediation.

Phylogenetic Typing

The following description provides mechanisms for characterizing the constituents of the enriched steady state microbial consortium.

Methods for generating oligonucleotide probes and microarrays for performing phylogenetic analysis are known to those of ordinary skill in the art (Loy, A., et al., Appl. Environ. Microbiol. 70: 6998-700, 2004) and (Loy A., et al., Appl. Environ. Microbiol. 68: 5064-5081, 2002) and (Liebich, J., et al., Appl. Environ. Microbiol. 72: 1688-1691, 2006). These methods are applied herein for the purpose of identifying microorganisms present in an environmental sample.

Specifically, conserved sequences of the 16S ribosomal RNA coding region of the genomic DNA were used herein. However there are other useful methodologies for phylogenetic typing noted in the literature. These include: 23S rDNA or gyrase A genes or any other highly conserved gene sequences. 16S rDNA is commonly used because it is the largest database of comparative known phylogenetic genotypes and has proven to provide a robust description of major evolutionary linkages (Ludwig, W., et al., Antonie Van Leewenhoek, 64: 285, 1993 and Brown, J. R. et al., Nature Genet., 28: 631, 2001).

The primers described herein were chosen as relevant to environmental samples from an oil reservoir (Grabowski, A., et al., FEMS Micro. Eco. 544: 427-443, 2005) and by comparisons to other primer sets used for other environmental studies. A review of primers available for use herein can be found in Baker et al (G. C. Baker, G. C. et al., Review and re-analysis of domain-specific primers, J. Microbiol. Meth. 55: 541-555, 2003). Any primers which generate a part or whole of the 16S rDNA sequence would be suitable for the claimed method.

DNA extraction by phenol/chloroform technique is known in the art and utilized herein as appropriate for extracting DNA from oil contaminated environmental samples. However, there are other methodologies for DNA extraction in the literature that may be used in accordance with the present invention.

DNA sequencing methodologies that generate >700 bases of high quality sequence may be used for the type of plasmid based sequencing in accordance with the present invention in conjunction with other sequence quality analysis programs. The comparisons by homology using the BLAST algorithms to any comprehensive database of 16S rDNAs would achieve an acceptable result for identifying the genera of microorganisms present in the environmental sample. The most widely used databases are ARB (Ludwig, W., et al., ARB: a software environment for sequence data. Nucleic Acid Res., 32: 1363-1371, 2004) and NCBI.

Fingerprint Profiling

Fingerprint profiling is a process of generating a specific pattern of DNA bands on an electrophoresis gel that are defined by their length and sequence. This profile is used to identify and describe the predominant microbial population of a culture assessing microbial diversity and population stability at particular metabolic state. For example, each band and its intensity in a given DGGE fingerprint profile represent an individual bacterial species present in the community and its relative representation in the population. Once generated, the data represents a fingerprint profile of the population at a given point in time and under certain growth conditions. The DGGE fingerprint profile can be compared to profiles of the consortium under prescribed growth conditions.

Denaturing Gradient Gel Electrophoresis

This technique has been adopted to analyze PCR amplification products by targeting variable sequence regions in conserved genes such as one of the nine variable regions found in the 16S rRNA gene of microorganisms (Gerard Muyzer et al., supra and Neefs, J-M et al. supra, and Botter, E. C., ASM News 1996). DGGE provides a genetic fingerprint profile for any given population.

Denaturing gradient gel electrophoresis (DGGE) and temperature gradient gel electrophoresis (TGGE) are electrophoresis-gel separation methods that detect differences in the denaturing behavior of small DNA fragments (50-600 bp), separating DNA fragments of the same size based on their denaturing or "melting" profiles related to differences in their base sequence. This is in contrast to non-denaturing gel electrophoresis where DNA fragments are separated only by size.

The DNA fragments are electrophoresed through a parallel DGGE gel, so called because the linear gradient of denaturant ~30-60% (urea/formamide) is parallel to the gel's electric field. Using DGGE, two strands of a DNA molecule separate or melt, when a chemical denaturant gradient is applied at constant temperature between 55°-65° C. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains, depending upon the denaturing conditions, which are characteristic of and determined by their nucleotide sequence. DGGE exploits the fact that virtually identical DNA molecules that have the same length and similar DNA sequence, which may differ by only one nucleotide within a specific denaturing domain, will denature at different conditions. Thus, when the double-stranded (ds) DNA fragment moves (by electrophoresis) through a gradient of increasing chemical denaturant, urea, formamide or both, it begins to denature and undergoes both conformational and mobility changes. At some point the two strands of the DNA to will come completely apart (also called "melting"). However, at some intermediate denaturant concentrations, as the denaturing environment increases, the two strands will become partially separated, with some segments of the molecules still being double-stranded and others being single-stranded, specifically at the particular low denaturing domains; thus, forming variable and intermediate denatured structures, which begin to retard the movement of the fragments through the gel denaturant gradients. The dsDNA fragment will travel faster than a denatured single-stranded (ss) DNA fragment. The more denatured fragment will travel slower through the gel matrix. The DGGE gel electrophoresis method offers a "sequence dependent, size independent method" for separating DNA molecules.

In practice, the DGGE electrophoresis is conducted at a constant temperature (60° C.) and chemical denaturants are used at concentrations that will result in 100% of the DNA molecules being denatured (i.e., 40% formamide and 7M urea). This variable denaturing gradient is created using a gradient maker, such that the composition of denaturants in the gel gradually decreases from the bottom of the gel to the top, where the fragments are loaded, e.g., 60% to 30%.

The principle used in DGGE profiling can also be applied to a second method, Temperature Gradient Gel Electrophoresis (TGGE), which uses a temperature gradient instead of a chemical denaturant gradient. This method makes use of a temperature gradient to induce the conformational change of dsDNA to ssDNA to separate fragments of equal size with different sequences. As in DGGE, DNA fragments will become immobile at different positions in the gel depending upon their different nucleotide sequences.

For characterizing microbial communities, DGGE fingerprint profiling has been applied to identify and characterize the genetic diversity of complex microbial populations much as, riboprinting has been applied to identify new environmental isolates by their rRNA fingerprint profile as being the same or different from previously described strains.

In practicing DGGE profiling, the variable sequence regions found in the 16S rRNA gene of microorganisms are targeted in PCR amplification of whole DNA isolated from a mix population (Gerard Muyzer, et al., supra). The variable or "V" regional segment not only differs in nucleotide sequence, but in length and secondary structure in the sequence. It is only recognizable as similar sequence in only closely related microorganisms. There are nine variable regions in the bacterial/archaeal 16S gene. These variable regions are designated by the letter V plus the number 1 through 9. Two V regions are most useful in using DGGE profile analysis, the V3 region and the V4/V5 region. Both V regions are flanked by universally conserved U regions.

The V3 region is flanked by two U sequences. The first at base coordinates 341 to 357 where bacteria and archaeal signature sequences exist. Bacterial universal primer, UB357F (SEQ NO: 5) and archaeal universal primers 341F1 and 341F2, (SEQ NO: 7 and SEQ NO: 9 respectively) are designed from this region. The other U region, which is universally conserved in all phylogenetic domains, is found at base coordinates, 518 to 534. The domain universal reverse primer, UB518R (SEQ NO: 5) is designed from this region.

The V4/V5 region is also flanked by two universal conserved sequences. The first as above is the domain universal region at base coordinates, 518 to 534. The domain universal forward, U519F (SEQ NO: 11) was designed from this region. The other region at base coordinates 918 to 960, where additional universal bacterial and archaeal signature sequences exist. The bacterial universal reverse primer, UB939R (SEQ NO: 14) and Archaeal universal primer UA958R (SEQ NO: 13) in this application were designed from this region.

A 40-bp GC-rich clamp in the 5' end of one of the PCR primers makes the method robust for genetic fingerprint profiling analysis of microbial populations. For profile analysis of region V3, the GC-clamp was designed into the bacterial universal primer, designated dG•UB357F (SEQ NO: 6) and archaeal universal primers designated dG•341F1 and dG•341F2, (SEQ NOs: 8 and 10 respectively) and for the V4/V5 region, the domain universal forward, designated dG•U 519F (SEQ NO: 12) was designed from this region. Using this method, PCR amplification of the total DNA from a diverse microbial population produces amplified fragments consisting of heterogeneous sequences of approximately 193 bp in length. These 16S rDNA fragments, when analyzed by DGGE analysis, demonstrate the presence of multiple distinguishable bands in the separation pattern, which are derived from the many different species constituting the population. Each band thereby, represents a distinct member of the population. Intensity of each band is most likely representative of the relative abundance of a particular species in the population, after the intensity is corrected for rRNA gene copies in one microbe versus the copies in others. The banding pattern also represents a DGGE profile or fingerprint of the populations. Using this method, it is possible to identify constituents, which represent only 1% of the total population. Changes in the DGGE fingerprint profile of the population can signal changes in the parameters, e.g., the electron donors and electron acceptors that determine the growth and metabolism of the community as a whole.

Relevant Functionalities of Characterized, Enriched Steady State Microbial Consortium Once an enriched steady state microbial consortium has been characterized, or in certain embodiments prior to genetic characterization of the constituents, the consortium may be assayed for one or more relevant functionality related to enhancing oil recovery or bioremediation of a hydrocarbon-contaminated site, including ability to degrade crude oil under the conditions of interest. Assays for the relevant functionalities include microsand column release assay and the LOOS (Liberation of Oil Off Sand) test (see Example 8) and the "sand packed slim tube or core flood test".

Inoculation of an Oil Well for Enhanced Oil Recovery

The following steps are taken to inoculate an oil well/reservoir:

a) Inoculating the microbial consortium in a bioreactor containing an anaerobic minimal salts medium, the target crude oil and an appropriate electron acceptor (e.g., nitrate herein).

b) Incubating the microbial consortium of step (a) at a temperature similar to the target well to obtain a seed population of the microbial consortium (e.g., 30° C., or in the range of room temperature, +/−5° C. in this disclosure).

c) Inoculating the seed microbial consortium of step (b) under anaerobic condition into anaerobic reservoir injection water.

d) Injecting the biological mixture of step (c) in to the reservoir, followed by injection water with dissolved electron acceptor to push the consortium mixture into the reservoir subterranean matrix, allowing the microbial consortium to grow and propagate resulting in dissociation and release of the crude oil from the reservoir matrix.

Inoculation of a Hydrocarbon-Contaminated Environmental Site for In Situ Bioremediation The following steps are taken to inoculate a hydrocarbon-contaminated environmental site:

a) Inoculating the microbial consortium in a bioreactor containing an anaerobic minimal salts medium, the target crude oil and an appropriate electron acceptor (e.g., nitrate in this disclosure).

b) Incubating the microbial consortium of step (a) at a temperature similar to the target site to obtain a seed population of the microbial consortium (e.g., 30° C., or in the range of room temperature, +/−5° C. in this disclosure).

c) Inoculating the seed microbial consortium of step (b) under anaerobic condition into contaminated site's subsurface.

d) Injecting the biological mixture of step (c) in to the subsurface, followed by injection water with dissolved electron acceptor to push the consortium mixture into the subterranean matrix, allowing the microbial consortium to grow and propagate resulting in degradation of the hydrocarbon contaminants.

Benefits of Enhancing Oil Recovery or In Situ Bioremediation Using Enriched Steady State Microbial Consortium In this application, methods are disclosed to provide an enriched steady state consortium of microbial population, under denitrifying conditions, using a chemostat bioreactor. The enriched steady state consortium population anaerobically degrades crude oil components under reservoir conditions or environmental conditions to modify the physiochemical properties of the crude oil and/or the reservoir environmental matrix, resulting in enhanced recovery of the crude oil. Furthermore, modifying the hydrocarbons of a hydrocarbon-contaminated environmental site by this consortium, results in its in situ bioremediation. The ideal consortium would be developed and enriched from an indigenous microbial population.

An additional benefit of the application of the present microbial consortium may be in the prevention of the damage to the oil pipeline and oil recovery hardware. Corrosion of the oil pipeline and other oil recovery hardware may be defined as the destructive attack on metals by some microbial, chemical or electrochemical mechanisms. Microbially induced corrosion in oil pipelines is known (EP3543361 B and U.S. Pat. No. 4,879,240A) and is caused by a variety of microorganisms including, but not limited to, aerobic bacteria, anaerobic bacteria, acid forming bacteria, slime formers, and sulfate reducing bacteria (SRB). In an anaerobic environment, corrosion is most commonly attributed to the growth of dissimilatory SRB. This group of bacteria is responsible for possibly 50% of all instances of corrosion. The control of microbial corrosion in oil recovery operations generally incorporates both physical or mechanical and chemical treatments.

The use of nitrate as a means of controlling the activity of SRB and removing hydrogen sulfide from oil pipeline and other oil recovery hardware is well documented (The stimulation of nitrate-reducing bacteria (nrb) in oilfield systems to control sulfate-reducing bacteria (srb), microbiologically influenced corrosion (mic) and reservoir souring an introductory review, published by the Energy Institute, London, 2003). Because nitrate is a better electron acceptor than sulfide, nrb have a competitive advantage over srb. Nitrate produces a higher growth yield than sulfide reduction does. Application of denitrifying microorganisms for enhancing oil recovery, therefore, may provide a cost effective, efficient and environmentally acceptable means of controlling SRB and remediating hydrogen sulfide contaminated systems, avoiding the use of expensive and environmentally unacceptable organic biocides. The use of the POG1 consortium therefore, may not only be beneficial to oil recovery, it may also prevent costly damage to the oil pipeline and other oil recovery hardware.

While aerobic in situ bioremediation of crude oil or its hydrocarbon components is in many cases it is impractical because of the anoxic nature of the natural environments contaminated with hydrocarbons, they may be bioremediated using by anaerobic microorganisms. Theoretically, the differences in energy release from the organic carbon oxidation by the different electron acceptors will be the controlling factor for the different anaerobic redox environments developing around the carbon source. Anaerobic oxidation of hydrocarbon compounds occurs under specific redox conditions for each electron acceptor, which include nitrate, iron (III), manganese (IV), sulfate, carbon dioxide, nitrite, ferric ion, sulfur, sulfate, selenate, arsenate, carbon dioxide and organic electron acceptors that include the chloroethenes, fumarate, malate, pyruvate, acetylaldehyde oxaloacetate and similar unsaturated hydrocarbon compounds. The rate of degradation in these redox zones is relevant to the abundance of the relevant microbes, the availability of the hydrocarbon via diffusion, the kinetics and energetics of the initial hydrocarbon-activating reaction which is dependant on the redox potential of the contaminated area.

Denitrifying bacteria provide an excellent choice for in situ bioremediation, because they grow rapidly under anaerobic conditions and yield substantial cell mass. In addition, denitrifying microorganisms from the genera *Thauera*, *Azoarcus* and *Dechloromonas* have been shown to breakdown hydrocarbons such as benzene, toluene, ethylbenzene, and xylenes (BTEX), which are constituents of crude oil (see above for references). In situ bioremediation remains potentially the most cost-effective cleanup technology for removing these compounds from contaminated sites. Application of the POG1 consortium may provide a custom bacterial culture that may be used to remediate crude oil, BTEX and other related hydrocarbon contaminated sites. Bioremediation may take place when the steady state consortium cells are exposed to hydrocarbons and convert them into products such as carbon dioxide, water, and oxygen or growth of the steady state consortium cells may allow for the release of high molecular weight hydrocarbons to the surface for subsequent removal by physical clean up methods. In some embodiments, the steady state consortium may be incubated in the environment to be bioremediated without any added co-substrate, or other carbon or energy source. The bioremediation process may be monitored by periodically taking samples of the contaminated environment, extracting the hydrocarbons, and analyzing the extract using methods known to one skilled in the art. Contaminated substrates that may be treated with the steady state consortium include, but are not limited to, beach sand, harbor dredge spoils, sediments, wastewater, sea water, soil, sand, sludge, air, and refinery wastes.

In another embodiment, the contaminated target may be an oil pipeline or refinery equipment. Hydrocarbon incrustation and sludge build-up are significant causes of decreased pipeline performance and can eventually lead to failure of the pipeline. Because of the ability of the steady state consortium to release hydrocarbons, its application to an oil pipeline containing incrusted hydrocarbons or hydrocarbon-containing sludge may be useful in the removal of the unwanted hydrocarbons from the pipeline.

General Methods

Growth of Microorganisms

Techniques for growth and maintenance of anaerobic cultures are described in "Isolation of Biotechnological Organisms from Nature", (Labeda, D. P. ed. p 117-140, McGraw-Hill Publishers, 1990). Anaerobic growth was measured by nitrate depletion from the growth medium over time. Nitrate was utilized as the primary electron acceptor under the growth conditions used in this invention. The reduction of nitrate to nitrogen has been previously described (Moreno-Vivian, C., et al., J. Bacteriol. 181: 6573-6584, 1999). In some cases, nitrate reduction processes lead to nitrite accumulation, which is subsequently, further reduced to nitrogen.

Accumulation of nitrite is therefore also considered evidence for active growth and metabolism by these microorganisms.

Description of the Chemostat Bioreactor Used in this Disclosure

Figure 3:
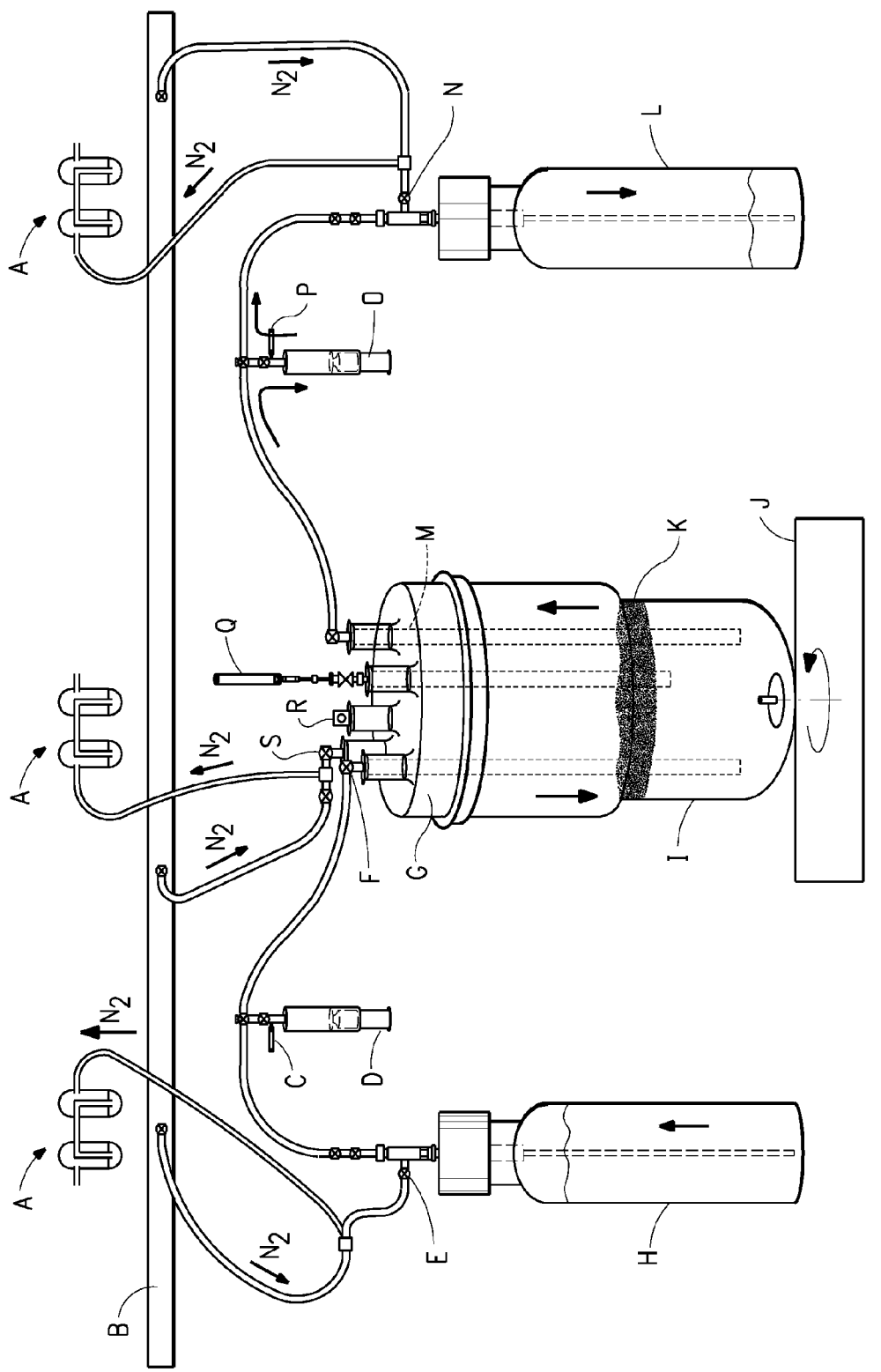

In this disclosure, a chemostat bioreactor was used as a bioreactor to maintain the consortium population in a steady state, using crude oil in excess as the sole energy source and a limiting nitrate supply, as the electron acceptor. FIG. 3 shows a diagram of the chemostat bioreactor used in this disclosure. The chemostat bioreactor was designed and used as a continuous-cultivation system, using a constant feed of medium and nitrate to develop a steady state population designated "POG1 consortium". The chemostat bioreactor was operated under anaerobic conditions, at room temperature, pH 7.4 and one atmosphere pressure, using the targeted crude oil (Milne Pont reservoir, North Slop of Alaska) as the carbon source (primary source of electron donors), and supplying a minimal salts medium (Table 2) containing minimal essential minerals, salts, vitamins and nitrate, as the primary electron acceptor, for growth.

TABLE 2

Composition of the SL10 minimal salts medium - The pH of the medium was adjusted to between 7.4-7.8

| Growth component | Final Concentration | Chemical Source |
| --- | --- | --- |
| Nitrogen | 18.7 µM | $NH_4Cl$ |
| Phosphorus | 3.7 µM | $KH_2PO_4$ |
| Magnesium | 984 µM | $MgCl_2 \cdot 6H_2O$ |
| Calcium | 680 µM | $CaCL_2 \cdot 2H_2O$ |
| Sodium chloride | 172 mM | NaCl |
| Trace metals | | |
| | 670 µM | nitrilotriacetic acid |
| | 15.1 µM | $FeCl_2 \cdot 4H_2O$ |
| | 1.2 µM | $CuCl_2 \cdot 2H_2O$ |
| | 5.1 µM | $MnCL_2 \cdot 4H_2O$ |
| | 12.6 µM | $CoCl_2 \cdot 6H_2O$ |
| | 7.3 µM | $ZnCl_2$ |
| | 1.6 µM | , $H_3BO_3$ |
| | 0.4 µM | $Na_2MoO_4 \cdot 2H_2O$ |
| | 7.6 µM | $NiCl_2 \cdot 6H_2O$ |
| Selenium-tungstate | 22.8 nM | $Na_2SeO_3 \cdot 5H_2O$ |
| | 24.3 nM | $Na_2WO_4 \cdot 2H_2O$ |
| PH buffer/Bicarbonate | 23.8 nM | $NaHCO_3$ |
| vitamins | 100 µg/L | vitamin B12 |
| | 80 µg/L | p-amino-benzoic acid |
| | 20 µg/L | nicotinic acid |
| | 100 µg/L | calcium pantothenate |
| | 300 µg/L | pyridoxine hydrochloride |
| | 200 µg/L | thiamine-HCL·$2H_2O$ |
| | 50 µg/L | alpha-lipoic acid |
| Electron acceptor | 0.4 g/L | $NaNO_3$ |

The chemostat bioreactor was set up in a chemical hood at room temperature (20 to 25° C.). All headspaces were anaerobic, using a blanket of nitrogen and an open-ended nitrogen flow (<1 psi) system, with a reverse double bubbler system, containing 5 mL mineral oil closing off the system from the atmosphere. Both the initial SL10 medium in the bioreactor and in the medium feed reservoir were degassed with an anaerobic mix of carbon dioxide and nitrogen (20/80 on a % basis) for 10 min, the pH checked and then titrated with either $CO_2/N_2$ mix or just $N_2$ until it was pH7.4. The SL10 minimal salts medium (1 L), in the bioreactor, was initially supplemented with 800 ppm nitrate and 400 mL of the targeted crude oil. The bioreactor was inoculated with 50 mL of the $3^{rd}$ generation ($3^{rd}$ gen) parent POG1 from enrichment culture (designated EH50:1) grown on the target crude oil and 1600 ppm nitrate for 1 week and incubated at room temperature while shaking at 100 rpm. A magnetic stirrer at the bottom of the reactor was stirring the culture at 40 to 50 rpm.

The SL10 medium, supplemented with 3800 ppm nitrate, was pumped from the medium reservoir (FIG. 3: G) into the chemostat bioreactor by means of the feed syringe pump (KDS230 Syringe Pump, KD Scientific, Holliston, Mass.) (FIG. 3: D). A sampling port was attached to and inline with the feed syringe pump. A 5 mL Becton-Dickinson (BD) sterile plastic polypropylene syringe (FIG. 3: C) (Becton-Dickinson, Franklin Lakes, N.J.) was attached to the sampling port and had a double function: 1) as a sampling syringe for the input feed and 2) as a 5 psi pressure release valve for the feed syringe pump. The effluent from the chemostat bioreactor was pumped into an effluent reservoir (FIG. 3: L) by means of the effluent syringe pump (supra) (FIG. 3: O). A second sampling port was attached to and inline with the effluent syringe pump. The effluent sampling port also had a 5 mL BD sterile plastic polypropylene syringe (supra) attached (FIG. 3: P). Again, it functioned both as a sampling syringe for effluent and as a 5 psi pressure release valve for the effluent syringe pump.

Obtaining the Environmental Sample

In this disclosure, soil or water samples obtained from anaerobic and microaerophilic (aerobic microorganisms that requires lower levels of oxygen to survive) locations on a hydrocarbon-contaminated site, which had been exposed to tar, creosol and polycyclic aromatic hydrocarbons (PAHs) were used for developing the microbial consortium. Soil samples were taken from locations where PAHs had been shown to be at elevated levels. Soil samples were placed in 500 mL brown bottles, filled to the top, sealed with no air space and, then shipped back to the lab on ice in a cooler. Once in the lab, the samples were placed in a Coy Type B anaerobic chamber (Coy Laboratories, Grass Lake, Mich.), filled with a specific anaerobic gas mixture (oxygen free anaerobic mix of hydrogen, carbon dioxide and nitrogen, 5%, 10% and 85%, respectively) for further processing.

Ion Chromatography

An ICS2000 chromatography unit (Dionex, Banockburn, Ill.) was used to quantitate nitrate and nitrite ions in the growth medium. Ion exchange was accomplished on an AS15 anion exchange column using a gradient of 2 to 50 mM potassium hydroxide. Standard curves were generated and used for calibrating nitrate and nitrite concentrations.

Genomic DNA Extractions from Bacterial Cultures

To extract genomic DNA from liquid bacterial cultures, cells were harvested and concentrated by filtration onto a 0.2 micron Supor® Filter (Pall Corp, Ann Arbor, Mich.) or by centrifugation. An aliquot (2-5 mL) of a bacterial culture was passed through a 0.2 micron, 25 mm filter disk in a removable cartridge holder using either vacuum or syringe pressure. The filters were removed and placed in the following lysis buffer (100 mM Tris-HCL, 50 mM NaCl, 50 mM EDTA, pH8.0) followed by agitation using a Vortex mixer. The following reagents were then added to a final concentration of 2.0 mg/mL lysozyme, 10 mg/mL SDS, and 10 mg/mL Sarkosyl to lyse the cells. After further mixing with a Vortex mixer, 0.1 mg/mL RNase and 0.1 mg/mL Proteinase K were added to remove the RNA and protein contaminants and the mixture was incubated at 37° C. for 1.0-2.0 hr. Post incubation, the filters were removed and samples were extracted twice with an equal volume of a phenol:chloroform:isoamyl:alcohol (25:24:1, v/v/v) and once with chloroform:isoamyl alcohol (24:1, v/v). One-tenth volume of 5.0M NaCl and two volumes of 100% ethanol were added to the aqueous layer and mixed. The tubes were frozen at −20° C. overnight and then centrifuged at 15,000×g for 30 min at room temperature to pellet chromosomal DNA. The pellets were washed once with 70% ethanol, centrifuged at 15,000×g for 10 min, dried, resuspended in 100 µL of de-ionized water and stored at −20° C. An aliquot of the extracted DNA was analyzed on an agarose gel to ascertain the quantity and quality of the extracted DNA.

Population Analysis of the Microorganisms of the Steady State Consortium and Parent Enrichment Cultures Using Cloned 16S rDNA Libraries Primer sets were chosen from Grabowski et al. (FEMS Microbiol. Ecol., 54: 427-443, 2005) to generate 16S rDNA of microbial species in DNA samples prepared from the consortium. The combination of forward primer (SEQ ID NO: 1) and reverse primers (SEQ ID NOs: 2 or 3) were chosen to specifically amplify the bacterial 16S rDNA sequences.

The PCR amplification mix included: 1.0× GoTaq PCR buffer (Promega), 0.25 mM dNTPs, 25 µmol of each primer, in a 50 µL reaction volume. 0.5 µL of GoTaq polymerase (Promega) and 1.0 µL (20 ng) of sample DNA were added. The PCR reaction thermal cycling protocol used was 5.0 min at 95° C. followed by 30 cycles of: 1.5 min at 95° C., 1.5 min at 53° C., 2.5 min at 72° C. and final extension for 8 min at 72° C. in a Perkin Elmer 9600 thermal-cycler (Waltham, Mass.). This protocol was also used with cells from either purified colonies or mixed species from enrichment cultures.

The 1400 base pair amplification products for a given DNA pool were visualized on 0.8% agarose gels. The PCR reaction mix was used directly for cloning into pPCR-TOPO4 vector using the TOPO TA cloning system (Invitrogen) as recommended by the manufacturer. DNA was transformed into TOP10 chemically competent cells selecting for ampicillin resistance. Individual colonies (~48-96 colonies) were selected and grown in microtiter plates for sequence analysis.

Plasmid Template Preparation

Large-scale automated template purification systems used Solid Phase Reversible Immobilization (SPR1, Agencourt, Beverly, Mass.) (DeAngelis, M. M., et al., Nucleic Acid Res., 23: 4742-4743, 1995). The SPRI® technology uses carboxylate-coated, iron-core, paramagnetic particles to capture DNA of a desired fragment length based on tuned buffering conditions. Once the desired DNA is captured on the particles, they can be magnetically concentrated and separated so that contaminants can be washed away.

The plasmid templates were purified using a streamlined SprintPrep™ SPR1 protocol (Agencourt). This procedure harvests plasmid DNA directly from lysed bacterial cultures by trapping both plasmid and genomic DNA to the functionalized bead particles and selectively eluting only the plasmid DNA. Briefly, the purification procedure involves addition of alkaline lysis buffer (containing RNase A) to the bacterial culture, addition of alcohol based precipitation reagent including paramagnetic particles, separation of the magnetic particles using custom ring based magnetic separator plates, 5× washing of beads with 70% ETOH and elution of the plasmid DNA with water.

rDNA Sequencing, Clone Assembly and Phylogenetic DNA Analysis

DNA templates were sequenced in a 384-well format using BigDye® Version 3.1 reactions on ABI3730 instruments (Applied Biosystems, Foster City, Calif.). Thermal cycling was performed using a 384-well thermal-cycler. Sequencing reactions were purified using Agencourt's CleanSeq® dye-terminator removal kit as recommended by the manufacturer. The reactions were analyzed with a model ABI3730XL capillary sequencer using an extended run module developed at Agencourt. All sequence analyses and calls were processed using Phred base calling software (Ewing et al., Genome Res., 8: 175-185, 1998) and constantly monitored against quality metrics.

Assembly of rDNA Clones

A file for each rDNA clone was generated. The assembly of the sequence data generated for the rDNA clones was performed by the PHRAP assembly program (Ewing, et al., supra). Proprietary scripts generate consensus sequence and consensus quality files for greater than one overlapping sequence read.

Analysis of rDNA Sequences

Each assembled sequence was compared to the NCBI (rDNA database; ~260,000 rDNA sequences) using the BLAST algorithm program (Altschul, supra). The BLAST hits were used to group the sequences into homology clusters with ≥90% identity to the same NCBI rDNA fragment. The homology clusters were used to calculate proportions of particular species in any sample. Because amplification and cloning protocols were identical for analysis of each sample, the proportions could be compared from sample to sample. This allowed comparisons of population differences in samples taken for different enrichment selections and or at different sampling times for the same enrichment consortium culture.

Using Fingerprint Profiles to Characterize the Genetic Diversity of Complex Microbial Populations For characterizing microbial communities, DGGE fingerprint profiling (as described above) has been applied to identify and characterize the genetic diversity of complex microbial communities. Targeting the variable sequence regions found in the 16S rRNA gene of microorganisms, Muyzer, G., et al (supra) PCR amplified DNA sequence of the V3 region of 16S rRNA genes in a mixed population. As stated above, the region is flanked by two universal conserved primer regions one at 341 to 357 and the other at 518 to 534. A 40-bp GC-rich clamp in the 5' end of one of the forward PCR primers, which included: universal bacterial primer 357, universal archaeal primers, 341F1, 341F2, (SEQ ID NOs: 5, 7 and 9) were designed as dG•UB 357, dG•UA 341F1 and dG•UA 341F2, respectively (SEQ ID NOs: 6, 8 and 10). As described above, the rDNA PCR products were electrophoresed on a linear gradient of denaturant ~30-60% (urea/formamide) which is parallel to the gel's electric field. DGGE gels were cast and electrophoresed using a D Gene™: Denaturing Electrophoresis System from BIORAD (Hercules, Calif.) following manufacturer's suggested protocols. rDNA samples were electrophoresed at a constant temperature of 60° C. for 8-24 hr at an appropriate voltage depending upon the 16S rDNA fragment population being analyzed. The electrophoresis buffer (1XTAE) was preheated to the target temperature in the D GENE chamber prior to electrophoresis. DGGE gels were stained with SYBR® GOLD nucleic acid stain (Invitrogen, Carlsbad, Calif.) for visualization and imaged on a Kodak imaging station 440. Multiple distinguishable bands, which were visualized in the separation pattern, were derived from the different species which constituted the POG1 population. Each band thereby, represented a distinct member of the population. Intensity of each band was most likely representative of the relative abundance of a particular species in the population, after the intensity was corrected for rRNA gene copies in one microbe versus the copies in others. The banding pattern also represented a DGGE profile or fingerprint of the populations. It is possible to identify constituents, which represent only 1% of the total population. Changes in the DGGE fingerprint profile of the population can signal changes in the parameters, e.g., the electron donors and electron acceptors that determine the growth and metabolism of the community as a whole. Thus the method described above provided a unique and powerful tool for conclusive identification of various microbial species within a mixed population.

Microsand Column Oil Release Test

Isolated bacterial strains were examined for their ability to release oil from sand using a microsand column assay to visualize oil release. The microsand column consisted of an inverted glass Pasteur pipette containing the sand (10 to 100 microns) from the Alaskan North Slope oil reservoirs, which had been coated with crude oil and allowed to age for at least one week. Specifically, oil and sand were autoclaved separately to sterilize. Autoclaved sand samples are then transferred to a vacuum oven and dried at 180° C. for a minimum of one week. Sterilized dried sand and oil were then combined ~1:1 v/v in an anaerobic environment. The mixtures were stirred and allowed to age for a minimum of seven days in an anaerobic environment. The barrels of glass Pasteur pipette (5¾ inches) were cut to approximately half height (3 inches) and autoclaved. The cut end of the pipette was plunged into the sand/oil mix and the core filled to about 0.5 inches in height from the bottom of the pipette barrel. Next, the cut-end of the pipette, which contained the oil/sand mixture, was then placed (with the tapered end of the pipette pointing upward) into the 13 mm glass test tube. A test inoculum in four milliliters of minimal salts medium was added to the 13 mm glass tube. The apparatus was sealed inside 23×95 mm glass vials in an anaerobic environment. Oil released from the sand collects in the narrow neck of the Pasteur pipettes or as droplets on the surface of the sand layer. Cultures that enhanced release of oil over background (sterile medium) were presumed to have altered the interaction of the oil with the sand surface, demonstrating the potential to contribute to enhancing oil recovery in a petroleum reservoir.

Gas Chromatography

A flame ionization detector gas chromatography (GC FID) method was developed to analyze the wet sand from the sacrificed slim tubes for residual oil. An empirical relationship was determined based on North Slope sand and the intrinsic pore volume of packed sand, e.g., for 240 g of packed sand there was a pore volume of 64 mL. Weights of the individual sand samples were obtained and the oil on the sand was extracted with a known amount of toluene. A sample of this toluene with extracted oil was then analyzed by GC. The samples were analyzed using an Agilent Model 5890 Gas Chromatograph (Agilent, Wilmington, Del.) fitted with equipped with a flame photoionization detector, a split/splitless injector and capillary column, DB5 column (length 30m× thickness 0.32 mm, film thickness 0.25 µm). An aliquot of 2 µL was injected with an analysis of 42 min. The injector temperature was at 300° C. and the detector temperature kept at 300° C. The carrier gas was helium, flowing at 2 mL/min. The FID detector gases were air and hydrogen flowing at 300 mL/min and 30 mL/min, respectively. A calibration curve was generated and used to determine the amount of oil in toluene on a weight percent basis. The calibration curve used 0.01, 0.1, 1, 5, and 10 wt % dissolved crude oil in toluene.

EXAMPLES

The present disclosure is further defined in the following Examples. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications to the disclosure to adapt it to various usages and conditions.

In the present disclosure, it was intended to develop a steady state consortium of microorganisms, under anaerobic denitrifying conditions, using crude oil as the carbon source would maintain the relative abundance of various microbial species of the consortium hence allowing the consortium's optimal operation under specific environmental conditions for enhanced oil recovery or in situ bioremediation of hydrocarbon-contaminated sites as compared to the ability of a single major species on the consortium as shown below.

Additional abbreviations used in the Examples below are as follows: "hr" means hour(s), "min" means minute(s), "L" means liter(s), "mL" means milliliters, "4" means microliters, "g" means gram, "mg/mL" means milligram per milliliter, "M" means molar, "mM" means millimolar, "mmoles" means millimoles, "µmoles" means micromoles, pmoles means picomole(s), "° C." means degrees Centigrade, "bp" means base pair(s), "rpm" refers to revolutions per minute, "ppm" means part per million, "v/v" means volume for volume, "v/v/v" means volume for volume for volume, "w/v" means weight for volume, "mL/hr" means milliliter per hour, "mL/min" means milliliter per minute, "%" means percent, "g" means gravitational force, "nm" means nano meter, "psi" means per square inch, "sec" means second, "LB" means Luria Broth culture medium, "R2A" means Reasoner's 2A culture medium, "PCR" means polymerase chain reaction and "SDS" means sodium dodecyl sulfate.

Example 1

Enrichment of a Microbial Consortium on Targeted Oil, as the Carbon Source, Under Denitrifying Anaerobic Conditions Development of the Parent POG1 Consortium For the present Example, parent enrichment cultures and a screening protocol were developed to identify microbes capable of growth under anoxic conditions on either crude oil or its components or samples from a hydrocarbon-contaminated site as the sole source of carbon. Nitrate was used as the primary electron acceptor as described herein. Soil samples were diluted at a 1 to 10 w/v ratio (10 g in 100 mL medium) and incubated in the SL10 medium and 250 ppm sodium nitrate as the electron acceptor for 72 hr as described below. These soil suspensions were used as an inoculum into 60 mL serum vials that contained 2:1 v/v of the minimal salts medium (20 mL) and the autoclaved crude oil (10 mL). Inoculations for the enrichment cultures were performed in the Coy anaerobic glove bag as described above. All crude oil used in the present Examples was from Milne Point, Prudhoe Bay on the Alaskan North Slop. The enrichment cultures were maintained anaerobically in the gas tight, septa sealed vials. These cultures were grown with moderate shaking (100 rpm) at ambient temperatures for weeks to months and sampled regularly for nitrate depletion and nitrite accumulation, visible turbidity and visible altered oil viscosity or oil adherence to glass. Cultures were occasionally sampled for analysis of their structure of microbial populations by rDNA sequence typing.

After 10 to 15 days, a biomass had developed in the original enrichment cultures that used crude oil for as the carbon source. Using these enrichments as an inoculum, a new series of enrichment parent subcultures were prepared. These second set of enrichment subcultures were designated "1$^{st}$ generation parent cultures" (1$^{st}$ gen) and were inoculated, capped and sealed in the anaerobic chamber. The 60 mL sub-culture serum vials contained 30 mL of the SL10 minimal salts medium (Table 2) with 250 ppm sodium nitrate and 15 mL autoclaved crude oil. The $1^{st}$ gen subcultures were grown with moderate shaking (100 rpm) at ambient temperatures for several weeks to three months and sampled regularly for nitrate depletion and nitrite accumulation, or in some cases, nitrite depletion. Changes observed included: visible turbidity, biofilms observed on the glass bottles or on the oil aqueous interface, oil-water emulsion, and visible altered oil viscosity or oil adherence to glass. Cultures were intermittently sampled for 16S rDNA phylogenetic typing.

When all available nitrates and produced-nitrites were reduced, the cultures were anaerobically subcultured into fresh medium supplemented with additional 250 ppm of sodium nitrate. Culture sampling was performed as before. After three months of growth and one to three subcultures, the resulting subculture populations were characterized using 16S rDNA typing (see above). The enrichment populations consisted of both facultative and strict anaerobes. These included various species of beta-Proteobacteria, primarily *Thauera* species and other species from: beta-Proteobacteria (Rhodocyclaceae), alpha-Proteobacteria, gamma-Proteobacteria, Deferribacteraceae, Bacteroidetes, Chloroflexi and Firmicutes/Clostridiales phyla (FIG. 1).

Since the individual enrichment populations were similar to each other, they were anaerobically pooled and inoculated into one liter of SL10 medium with 250 ppm sodium nitrate. The inoculated medium was then divided into 250 mL portions and each aliquot was inoculated into one of four 500 mL-serum bottles containing 125 mL of sterile crude oil. All bottles were anaerobically sealed. The cultures were referred to as "second-generation parent cultures" ($2^{nd}$ gen). Enrichments samples (designated EH36:1A, EH36:1B, EH36:1C, EH36:1D) (see Table 5) of the $2^{nd}$ gen cultures, were grown with moderate shaking (100 rpm) at ambient temperatures for several weeks and sampled regularly for nitrate and nitrite depletion. Nitrate was replenished to 250 ppm on four separate occasions. After the fourth depletion of nitrate, a 10 mL aliquot from one of the cultures was anaerobically inoculated and sealed into a 500 mL serum bottle containing 200 mL of SL10 medium with 2400 ppm sodium nitrate and 100 mL sterile crude oil, and designated as "third-generation parent" ($3^{rd}$ gen) (designated EH40:1 and EH44:1). The $2^{nd}$ gen cultures were continued on 250 ppm sodium nitrate, by removing 150 mL of culture and adding back 150 mL of sterile SL 10 minimal salts medium plus nitrate. All consortium cultures were incubated as described above for several weeks and regularly sampled for nitrate and nitrite depletion. After the $3^{rd}$ gen parent cultures had depleted the 2400 ppm sodium nitrate and all of the produced nitrite, all enrichment cultures were replenished with 2400 ppm sodium nitrate. After 190 days, all $2^{nd}$ and $3^{rd}$ gen enrichments had reduced 6600 ppm nitrate. Cultures were then sampled for 16S rDNA phylogenetic typing to characterize their populations (FIG. 2). The members of population profiles of the enrichments were similar to what had been detected in previous enrichments.

Example 2

Monitoring Denitrification and Growth of a Steady State Consortium in a Chemostat Bioreactor Growth of the steady state POG1 consortium in the chemostat was monitored by optical density ($OD_{550}$) and nitrate reduction through taking daily samples for six weeks and then every second to third day for the next nine weeks. The nitrate and nitrite concentrations were determined by ion chromatography as described above. For the first two weeks, nitrate was fed at 14 ppm/day and thereafter at 69 ppm/day. Table 3 shows that equilibrium for nitrate reduction was reached after 9 days, where all of the nitrate, as well as the produced nitrite, were completely reduced. The culture completely reduced its nitrate supply for the next 97 days. Cell density equilibrium was reached after 32 days, two weeks after the nitrate feed had been increased by approximately five fold. The optical densities remained relatively constant for the next 74 days. At 35 to 43 days, the cells started to aggregate together and form biofilms at the oil-aqueous interface and oil water emulsions were observed. These culture characteristics made it difficult to obtain homogenous samples for growth measurements. Between 30 and 32 days into the experiment, the magnetic stirrer had stopped mixing and nitrate reduction was interrupted due to incomplete mixing of the culture in the bioreactor. Once the stirrer was restarted, nitrate was completely reduced within two days and the chemostat returned to equilibrium.

The steady state POG1 consortium consumed 6662 mg or 107.5 mol of nitrate in 106 days before nitrate reduction began to decrease as indicated by the presence of 27 ppm nitrite in the effluent after 106 days. The decreased rate of nitrate reduction seemed to indicate that the target component of the oil was becoming limiting. The denitrification of nitrate and its reduced nitrite to nitrogen is equivalent to 537.3 mmol of electrons consumed in crude oil oxidation (Rabus, R., et al., Arch Microbiol., 163: 96-103, 1995). It follows that the equivalent of 1.23 g of decane (8.6 mmol) was degraded to carbon dioxide. Therefore since 400 g of crude oil had been added to the chemostat bioreactor, theoretically approximately 0.31% of the oil had been dissimilated.

TABLE 3

Monitoring the optical density, nitrate feed and denitrification of the POG1 consortium in the chemostat bioreactor

| | Time (days) | | | | | | | | | | | |
|---|---|---|---|---|---|---|---|---|---|---|---|---|
| | 0 | 4 | 9 | 11 | 18 | 32 | 42 | 57 | 71 | 85 | 91 | 106 |
| $OD_{550}$ nm | .04 | 0.553 | 0.584 | 0.586 | 0.717 | 1.151 | 1.469 | 0.870 | 0.994 | 0.814 | 0.989 | 0.906 |
| Total Nitrate fed | 583.0 | 631.4 | 699.5 | 763.4 | 1045 | 2002 | 2654 | 3448 | 4337 | 5226 | 5636 | 6662 |
| Nitrate in Effluent ppm | 356.1 | 5.7 | 0 | 0 | 0 | 150 | 0 | 0 | 0 | 0 | 0 | 0 |
| Nitrite in Effluent ppm | 0 | 4.7 | 1.4 | 0 | 1 | 26.6 | 0 | 0 | 0 | 0 | 0 | 27.1 |

After 106 days of incubation, biofilm was seen on the glass of the bioreactor at or near the oil/aqueous fraction. The oil and aqueous fractions showed signs of emulsification. To observe emulsification, samples were examined using dark field and bright field phase microscopy at 400× magnification (Zeiss Axioskop 40, Carl Zeiss Micro Imaging, Inc, Thornwood, N.Y.). Microbes adhered to both the glass slide and the cover slip, demonstrating a positive hydrophobic response. This assay is a modified version of a procedure which indirectly measures hydrophobicity through the attachment of microbes to polystyrene plates (Pruthi, V. and Cameotra, S., Biotechnol. Tech., 11: 671-674, 1997). In addition, tiny, emulsified oil droplets (around 3 to 40 micron in diameter) were seen in the aqueous phase. Bacteria were also seen in a biofilm-like attachments to some of these emulsified oil droplets.

An aliquot (1 µL) of the steady state POG1 consortium with an emulsified oil drop was placed on a microscope slide and covered with a 20 mm-square No. 1 coverslip and examined using a phase imaging microscopy under an oil emersion lens at 1000× magnification. Microbes were also found in the oil phase in irregular "pockets" formed around aggregated bacteria.

Normally water droplets that are trapped in oil will take on a near circular shaped form. The aqueous-oil interface was moving toward the bottom of the slide, the bacteria were being captured at the interface within these aggregated hydrophobic forms, which were eventually "pinched-off" and left in the oil phase.

Microbes were also seen aggregated at the aqueous-oil interface. Bacteria are usually attracted to the interface but not in mass; they often stream quickly along the interface in one direction, one bacterium at a time. In this Example, the microbes were attracted to the interface as a non-motile aggregate of 30 to 50 microns wide. These observations demonstrate formation of a hydrophobic aggregate mass that may contribute to the formation of the biofilm at the aqueous-oil interface or with an oil/aqueous emulsion. This structure allows microbes to interact with oil and use some of its components as their carbon source.

The members of population profiles of the steady state were similar to what had been detected in previous enrichments and are shown in Table 4 below. There were 73 unique sequences (SEQ ID NOs: 15-87), which were grouped into seven classes of bacteria, which included alpha-Proteobacteria, beta-Proteobacteria, gamma-Proteobacteria, Deferribacteraceae, Spirochaetes, Bacteroidetes and Firmicutes/Clostridiales and Incertae Sedis. The primary Genera continued to be the beta-Proteobacteria, *Thauera*. *Thauera* strain AL9:8 was the dominant constituent. The diversity among the members of *Thauera/Azoarcus* group (Rhodocyclaceae) is significant since there are 31 unique 16S rDNA sequences in this group whose sequence differences occur in the primary signature regions of the variable regions. Also the *Firmicutes/Clostridiales* group are diverse with 16 unique sequences that include constituents from the *Clostridia, Anaerovorax* and *Finegoldia* genera.

TABLE 4

Unique strains in consortium population based on 16S rDNA sequences

| Class | Genus | Highest Identity species | GenBank Accession No. | SEQ ID NO. |
|---|---|---|---|---|
| Beta-Proteobacteria | *Thauera* | *Thauera* strain AL9:8 | AJ315680 | 15 |
| | *Thauera* | *Thauera aromatica* | U95176 | 23, 24, 25, 26, 27, 28, 31, 32, 33, 34, 35, 36, 37, 38, 39, 40, 41, 67, 68 |
| | | *Thauera* sp. R26885 | AM084104 | 16, 19, 21, 30 |
| | *Azoarcus* | *Azoarcus* sp mXyN2 | X83533 | 17, 18, 22 |
| | | *Azoarcus* sp | AY570623 | 29, 54, 69, 86 |
| Gamma-Proteobacteria | *Azotobacter* | *Azotobacter beijerinckii* | AJ30831 | 20, 44, 46, 57, 70, 71, 72, 73, 74, 84, 85 |
| | *Pseudomonas* | *Pseudomonas putida* | EU930815 | 61, 80, 83 |
| | | *Pseudomonas pseudoalcligenes* | AB109012 | 60, 62 |
| Deferribacteraceae | *Deferribacter* | *Deferribacter desulfuricans* | AB086060 | 56, 77 |
| | *Flexistipes* | *Flexistipes* sp vp180 | AF220344 | 53, 58, 87 |
| Alpha-Proteobacteria | *Ochrobactrum* | *Ochrobactrum* sp mp-57 | AY331579 | 47 |
| | | *Ochrobactrum lupini* | AY457038 | 59 |
| Spirochaetes | *Spirochaeta* | *Spirochaeta* sp MET-_E | AY800103 | 43 |
| Bacteroidetes/ Chloroflexi group | Bacteroides | Uncultured Bacteroides/Cytophaga | DQ238269 | 78 |

TABLE 4-continued

Unique strains in consortium population based on 16S rDNA sequences

| Class | Genus | Highest Identity species | GenBank Accession No. | SEQ ID NO. |
|---|---|---|---|---|
| Firmicutes Clostridiales | Clostridia | Clostridium aceticum | Y181183 | 76, 81 |
|  |  | Clostridium chartatabidium | X71850 | 55, 63, 75 |
|  | Anaerovorax | Anaerovorax sp | EU498382 | 48, 49, 82, |
|  | Finegoldia | Finegoldia magna | NC010376 | 42, 45, 50, 51, 52, 64, 65, 66, 79 |

Example 3

Population Analysis of the Steady State POG1 Consortium and Parent POG1 Cultures Using Cloned 16S rDNA Libraries DNA was extracted as described above from the $3^{rd}$ gen POG1 parent enrichment cultures and from the steady state POG1 chemostat culture samples and used to make cloned 16S rDNA libraries. Briefly, the 1400 base pair 16S rDNA amplification products for a given DNA pool were visualized on 0.8% agarose gels. The PCR reaction mix was used directly for cloning into pPCR-TOPO4 vector using the TOPO TA cloning system (Invitrogen) following the manufacturer's recommended protocol. DNA was transformed into TOP10 chemically competent cells selecting for ampicillin resistance. Individual colonies (~48-96 colonies) were selected, grown in microtiter plates, prepared and submitted for sequence analysis as described above.

Results of 16S rDNA Sequence Analysis

An overall 16S profile was compiled for $1^{st}$ gen, $2^{nd}$ gen and $3^{rd}$ gen parent POG1 cultures described herein. 16S rDNA profiles were also prepared from samples taken at several different time points from the ongoing steady state POG1 chemostat culture. A minimum of 48 16S rDNA clones for each enrichment and/or steady state time sample were sent to Agencourt for sequencing. The 16S rDNA sequence obtained was subsequently blasted (BLASTn) against the NCBI database. Sequences were grouped into homology clusters with at 90% identity to the same NCBI rDNA fragment. The homology clusters obtained for all parent POG1 cultures and steady state culture were used to calculate the proportions of particular bacteria in any sample. The populations' results obtained from selected parent enrichment cultures verses steady state is shown FIG. 4.

Analysis indicated that 50-90% of the total 16S rDNAs sequenced belonged to the taxonomic class of beta-Proteobacteria, family Rhodocyclaceae. Members of the beta-Proteobacteria phylum subclass, *Thauera* in particular, were the most abundant microorganism in the steady state POG1 consortium at any given time. Strains of *Thauera* have been shown to grow on oil and or oil constituents under anaerobic conditions without the need for additional nutrient supplementation (Anders et. al. Int. J. Syst. Evol. Microbiol. 45: 327-333, 1995).

Sequences belonging to the phyla Bacteroides, Firmicutes/Clostridiales (low G+C gram-positive bacteria), Deferribacteres and Spirochaetes represented between 4-23% of the microbial population and were consistently represented in the POG1 consortium steady state samples and its parent enrichments. The sample size of cloned 16S rDNAs (n=47) for steady state POG1 samples most likely under report the incidences of these organisms in the microbial population. Sequences affiliated with members of the gamma-Proteobacteria, Pseudomonadales, were also represented at a consistently low level in steady state POG1 time samples. This is in contrast to 16S rDNA profiles obtained for several of the initial parent enrichments of this consortium, which did not contain Pseudomonadales 16S rDNA sequences indicating that members of this phylotype may not be critical to steady state POG1 function in MEOR or in-situ bioremediation.

Lastly, a low level of sequences (≤3%) associated with phylotypes representing the *Chloroflexi*, Synergistes, delta-Proteobacteria, and alpha-Proteobacteria were frequently detected in the POG1 parent enrichment cultures.

In summary, the distribution of 16S rDNA sequences described for the steady state POG1 culture as well as the POG1 parent enrichment cultures describes the composition of organisms that define the steady state POG1 consortium. This selected composition of microorganisms may enhance the oil recovery and may be effective in in-situ bioremediation of the hydrocarbon-contaminated sites.

Example 4

Partially Prophetic

Analysis of Microbial Community by DGGE

The distribution of individual microbial populations in the steady state POG1 consortium's community was analyzed using the 16S rDNA variable region analysis by DGGE. DNA for DGGE community fingerprinting was isolated from samples taken from the steady state POG1 consortium crude oil chemostat over the course of two months. PCR amplified fragments were generated using primers dG.UB357 and U518R for bacteria (SEQ ID NOs: 6 and 4) and dG.UA341F1 and F2 with U518R for Archaea (SEQ ID NOs: 8, 10 and 4). This produced an approximately 200 bp sequence from the V3 region of the bacterial and archaeal 16S rDNA which were then analyzed by DGGE. In addition, PCR amplified fragments for the V4/V5 region of the bacterial and archaeal 16S rDNA sequences were also generated producing fragments of approximately 400 bp generated using primers dG.U519F and UB 936R for bacteria (SEQ ID NOs: 12 and 14) and dG.U519F and UA 9958R for Archaea (SEQ ID NOs: 12 and 15). These PCR fragments were separated by length and nucleotide sequence using DGGE.

Denaturing gradient gel electrophoresis for fingerprint profiling was performed using a Bio-Rad DGGE DCode System (Bio-Rad Laboratories, Hercules, Calif.). Fingerprint profiles of the amplified rRNA gene fragments were resolved by electrophoresis at 60° C. at 35 V for 16 hr on 8% (w/v) denaturing polyacrylamide gels containing from 30% to 60% denaturant concentration gradient (w/v, 7M urea and 40% formamide in 1×TAE (50×TAE: 2M Tris-Acetate, 50 mM EDTA, pH 8.0)). FIG. 5 is an example of a community DGGE profile of the V4/V5 region from time zero to 52 days. The profiles of the steady state POG1 consortium test samples (days, 0, 4, 28, 44, 52) on the left side appear to have stabilized after 28 days. The controls, on the right half of the gel, include the parent POG1 startup inoculum EH50:1 and a *Thauera* strain AL9:8. Also included as controls were two strains isolated from the Alaskan North Slop production oil, strain LH4: 15 (*Pseudomonas stutzeri*) and strain AL1:7 (*Ochrobactrum* sp., from the Brucellaceae family), respectively. The last two strains were chosen as controls to see if the steady state POG1 population included microorganisms that have been seen as major constituents of an oil field population. The major band in all consortium profiles (A) correlated with the band observed for *Thauera* strain AL9:8.

The second band, (B), which correlates with strain LH4:15, appears to decrease as a major constituent of the population in profiles from day 4 through day 52. The third band (C), which correlates with strain AL1:7 is less dense and is a constituent of the population in profiles for zero through 28 days. However, this band disappears in the later stages of denitrification. Bands D through L are also detectable as minor constituent bands of the population in all samples.

The following steps are prophetic: To identify these steady state POG1 profile bands, previously identified 16S rDNA clones representing constituents from the steady state POG1 consortium, may be applied to DGGE analysis to identify individual DGGE bands as was done to identify to bands A through C in FIG. 5. The V4/V5 region from cloned constituent 16S rDNAs may be used to analyze and identify the remaining bands D through L of the steady state POG1 DGGE profile. The results should closely correlate with the profile bands with major constituents of the consortium identified in the earlier 16S rDNA profile in FIG. 5. Table 4 in Example 2 lists the isolated 16S rDNA clones, obtained from POG1 16S rDNA population profile studies. The clones used to obtain these sequences may be used to generate PCR produces using the DGGE PCR products to identify and correlate the individual bands (A-L) of the DGGE 16S V4/V5 rDNA. Table 4 also includes the associated NCBI rDNA database Accession number ID obtained for these reference clones. These clones represent the major groups of bacteria comprising the POG1 consortium, which include beta-Proteobacteria, primarily *Thauera aromatica* species (Rhodocyclaceae), and from Pseudomonadales, Bacteroidaceae, Clostridiaceae, Incertae Sedis., Spirochete, Spirochaetaceaes., Deferribacterales Brucellaceae and Chloroflexaceae. PCR amplified fragments for the V4/V5 region of the microbial 16S rDNA may then be generated from both the cloned rDNA (plasmid DNA) that were identified as POG1 constituents and genomic DNA from correlated POG1 samplings as well as POG1 cultures started form frozen culture stocks. Miniprep DNA from POG1 16S rDNA clones may be prepared using a Qiagen Miniprep Kit (Valencia, Calif.) following the manufacturer's protocol. PCR amplified fragments from the V4/V5 region of approximately 400 bp may be generated using primers dG.U519F and UB 936R for bacteria (SEQ ID NOs: 12 and 14). Amplified fragments may be separated by length and nucleotide sequence using DGGE as described above.

Example 5

Partially Prophetic

Long-Term Storage and Recovery of the Consortium for Field Inoculations

An important criterion for the application of any consortium is its viability and function following its long term storage. An aliquot (20 mL) of the steady state POG1 consortium was taken during the steady state growth in the chemostat. The 16S rDNA community sequence and a DGGE fingerprint profiles were performed to define the composition of the community at the sampling time point. The anaerobic sample was placed in a 15-20% glycerol mix (e.g., 150 µL of sterile degassed glycerol into 650 µL of the sample) in the Coy anaerobic chamber, dispensed into sterile 2.0 mL cryogenic polypropylene tubes and treated as described above. The tubes were quickly frozen on dry ice and stored in a −70° C. freezer until needed.

To test the viability of the steady state POG1 freezer culture or to use it as an inoculum, a cryogenic tube was removed from a −70° C. freezer and thawed on wet ice in an anaerobic chamber. An aliquot (50 µL) of the sample was used to start a seed culture for a larger inoculum for the chemostat bioreactor. The seed culture was inoculated into 20 mL of SL10 minimal medium supplemented with 300 ppm nitrate and 10 mL of the autoclaved-targeted crude oil in a 60 mL sterile serum bottle. The anaerobic bottle was sealed with a septum, incubated outside the anaerobic chamber at room temperature (20° C. to 25° C.) while shaking at 100 rpm on an orbital shaker. Culture turbidity, which is indicative of growth of the constituents of the consortium, was visually observed.

The following steps are prophetic: In addition, with a revived consortium, reduction of nitrate to nitrite is expected to occur after three days. When nitrate concentration reaches about 50 ppm or less, a sample may be taken for isolating the microbial community's DNA for 16S rDNA typing and DGGE fingerprint profiling. It would be expected that the DGGE profile and the 16S rDNA typing of the freezer seed culture would be similar to the profiles obtained for the steady state POG1 consortium. If the freezer culture were stable as expected, a seed culture may be prepared as an anaerobic inoculum for the chemostat bioreactor for nitrate assimilation analysis. The revived frozen consortium may also be used in an oil release sandpack or core flood assay. Furthermore, the revived frozen consortium may be used a reservoir growth-injection tank, which is a vessel next to the oil well for holding the culture prior to injection or it can be used for growth of the culture prior to injecting the culture it the oil well. In addition, it could be used as a seed culture for inoculating the initial culture that might be used for in situ bioremediation of the hydrocarbon-contaminated sites.

Example 6

Oil Release Sandpack or Core Flood Assay

The application of the steady state POG1 consortium to a sandpack saturated with oil to evaluate its use in MEOR and as a denitrifying consortium, growing in pipelines as possible method to impede the effects of SRB strains producing corrosion in pipelines or refinery pipes. This was accomplished using the sandpack technique in an in-house developed Teflon® shrink-wrapped sandpack apparatus that simulates packed sand of sandstone.

The process described herein was used for making two column sets, a "control" set and a "test" set, which was inoculated with the steady state POG1 consortium to test its efficacy to release oil from the sand column. Using a 1.1 inches thick, and 7 inches long Teflon heat shrink tube, an aluminum inlet fitting with Viton® O-ring was attached to one end of the tube using a heat gun. North Slope sand was added to the column which was vibrated with an engraver to pack down the sand and release trapped air. A second aluminum inlet fitting with Viton® O-ring was attached to the other end of the tube and sealed with heat a gun. The sandpack was then put in an oven at 275° C. for 7 min to evenly heat and shrink the wrap. The sandpack was removed and allowed to cool to room temperature. A second Teflon® heat shrink tube was installed over the original pack and heated in the oven as described above. After the column had cooled, a hose clamp was attached on the pack on the outer wrap over the O-ring and then tightened.

Both column sets (two columns in each set) were then flooded horizontally (at 60 mL/hr) with four pore volumes of "Brine" (sterile, anaerobic SL 10 medium, supplemented with 250 ppm nitrate and 3 mM phosphate buffer, pH 7.4) by means of a syringe pump and a 60 mL sterile plastic polypropylene syringe. Both sets of sandpacks were then flooded with anaerobic autoclaved crude oil to irreducible water saturation, which was predetermined to be two pore volumes. The oil was flooded, at a rate of 0.4 mL/hr, using a 10 mL sterile syringe and a syringe pump. The crude oil was aged on the sand by shutting-in the columns for seven days. One column set was anaerobically inoculated with one half of a pore volume at 0.4 mL/hr with a sample of the consortium removed anaerobically from the chemostat. Simultaneously a control inoculation using anaerobic "Brine" was also loaded on the control column set using the same procedure. The inocula were shut-in for incubation with the oil for seven days and the columns were then flooded with four pore volumes of anaerobic sterile "Brine" at 0.4 mL/hr.

At the conclusion of the production flood, the 7 inches long slim tubes were sacrificed into 5× one-inch sections labeled A-E. One inch was skipped at the beginning and at the exit of the slim tube to avoid edge effects during analysis. Section "A" came from the front end of the column. Sections A, C, and E were analyzed for residual oil saturation on the sand. The amount of oil on the wet sand from the sacrificed slim tubes for residual oil was measured by GC as described above. This value was multiplied by the total amount of toluene used to extract the oil resulting in the total amount of oil on the sand. The value obtained was then divided by the total sample weight to yield the percent of oil with respect to the total sample weight. The weight percent of oil of the sample was then multiplied by the ratio of the empirically derived characteristic of packed North Slope sand (total weight of sample after being flooded with brine divided by total sand weight, 1.27). This relationship is equal to the amount of oil on dry sand. This value was then multiplied by the ratio of the weight of the North Slope sand to the weight of the fluid trapped in the pore space of the sand, 3.75. The resulting value reflected the residual oil left on the sand in units of g of oil/g of total fluid in the pore space. As shown in Table 5, residual oil left on the column, in fractions A and C of the test column, were less than the controls confirming that the columns inoculated with the POG1 consortium released more oil than those that were not inoculated.

TABLE 5

Residual oil left on sand along the tube length after flooding with anaerobic sterile "Brine"

| Column Fraction | Average Percent Residual Oil on Sand | | |
|---|---|---|---|
| Assay Column | A | C | E |
| Test columns | 23.2% | 22.2% | 18.5% |
| Control columns | 27.3% | 22.3% | 18.2% |

Example 7

Ability of the Parent POG1 Consortium to Enhance Oil Release and Grow Using Oil as the Carbon Source The parent POG1 consortium cultures were examined for their ability to release oil from sand in a visual oil release assay using the microsand column described above. This Example was used evaluate the consortium for enhanced oil recovery and also as a denitrifying culture in pipelines as possible method to impede the effects of SRB strains producing corrosion in pipelines or refinery pipes, using oil as the carbon source. Inocula from early parallel enrichment cultures of the $2^{nd}$ gen parent POG1 consortium e.g., EH36:1A, EH36:1B, EH36:1C, EH36:1D each with ~250 ppm nitrate and one $3^{rd}$ gen culture (EH40:1) with high nitrate concentration (~1600 ppm) were tested in this assay. All enrichment cultures were grown anaerobically in the SL10 minimal salts medium (Table 2) using ACO oil as the carbon source and nitrate as the electron acceptor until turbidity was observed. All operations for preparation of the microsand columns, inoculation and growth were done in an anaerobic chamber using sterile techniques. A 4.0 mL aliquot of each inoculum was added to the 13 mm glass tubes either directly or diluted 1:2 with the minimal salts medium. The microsand columns (filled with oil-saturated sand as described above) were placed in each glass tube, immersed in the medium/cell inoculum with the tapered neck of the Pasteur pipettes pointing up. The outer vials were sealed in the anaerobic Coy chamber and allowed to incubate at ambient temperatures for the next several weeks. Each column was periodically checked for oil release. Cultures that enhanced release of oil over background (sterile medium) were presumed to have altered the interaction of the oil with the sand surface.

Oil released from the sand was visualized by the released oil collecting in the tapered neck of the Pasteur pipettes or forming droplets on the surface of the sand layer (FIG. 6). Oil release was observed for some of the POG1 parent enrichment cultures as rapidly as only 3 hr after inoculation. Oil release was also observed with the pure *Thauera* strain AL9:8, isolated from the $1^{st}$ gen POG1 parent enrichment cultures. Microsand columns were then observed over the course of several weeks. An increase in the initial amount of oil released was observed after 3 months of incubation. Uninoculated controls did not show visual release of oil over the course of the experiment. Triton® X-100 (Rohm & Haas Co), a non-ionic surfactant was used as a positive assay for the release of oil from sand. Table 6 lists the enrichment cultures tested and the observations of oil release after 7 days and 3 months incubation at ambient temperatures. These results indicated that the parent POG1 consortium interacted with oil-wet sands at the water/oil/sand interface and induced oil release from the sand's surface. Results described in Example 6 and 7 clearly underline the ability of the POG1 steady state consortium in the release of oil from sand. In addition, it is anticipated that this consortium may be used in applications such as for cleaning oil or refinery pipelines.

TABLE 6

Release of oil from microsand columns by enrichment cultures the steady state POG1 consortium

| Inoculum ID | dilution | Oil release T = 7 days | Oil release T = 3 months |
|---|---|---|---|
| Controls | | | |
| 1.0% Triton | no | +++ | ++++ |
| 1.0% Triton | ½ | ++ | +++ |
| NIC (medium) | no | − | − |
| Parent Environmental Enrichment Cultures | | | |
| EH36:1A | no | − | + |
| EH36:1B | no | + | ++ |
| EH36:1C | no | − | − |
| EH36:1C | ½ | + | + |
| EH36:1D | no | + | + |
| EH40:1 | no | − | +/− |
| EH40:1 | ½ | + | + |
| *Thauera* strain | | | |
| AL9:8 | no | + | ++ |

1. Microsand columns were scored for oil release on a scale of 1 to 5 (+) in order of increased oil release; (−) = no release of oil, 5 = complete release of oil from oil coated sand, as judged visually.

Example 8

The Ability of the Steady State Consortium to Release Oil from Sand Particles

In order to screen the enrichment cultures for the ability to release oil from the nonporous silica medium, a microtiter plate assay was developed to measure the ability of the microbes to release oil/sand from oil-saturated North Slope sand and evaluate its use in growing a denitrifying culture in pipelines as a possible method to impede the effects of SRB strains producing corrosion in pipelines or refinery pipes. The assay is referred to as the LOOS test (Liberation of Oil Off Sand).

A microtiter plate assay was developed to measure the ability of the enrichment cultures and the consortium to release oil/sand from the oil-saturated Alaskan North Slope sand. North Slope sand was autoclaved and then dried under vacuum at 160° C. for 48 hr and 20 g of this dried sand was then mixed with 5 mL of autoclaved, degassed crude oil obtained from Milne point, North Slope. The oil-coated sand was then allowed to adsorb to the sand and age anaerobically at room temperature for at least a week. Microtiter plate assays were set up in the Coy anaerobic chamber. An aliquot of the undiluted steady state POG1 consortium (20 mL) was added into the wells of a 12-well microtiter plate. The POG1 was grown anaerobically in SL10 minimal medium with 2000 ppm sodium nitrate and North Slope crude oil. The control wells contained 2 mL of the SL10/2000 ppm $NaNO_3$ medium alone. Approximately 40 mg of oil-coated sand was then added to the center of each well. Samples were then monitored over time for the release and accumulation of "free" sand collecting in the bottom of the wells. Approximate diameters (in millimeters) of the accumulated total sand released were measured daily. A score of 3 mm and above indicated the microbes' potential to release oil from a nonporous silica medium such as sand.

Table 7 shows the relative sand release by the steady state POG1 consortium over a period of four weeks. After about 15 days, a 4 mm zone of released sand was observed in the bottom of the wells containing the steady state POG1 consortium. No release was observed for the medium alone. The results indicate that the steady state POG1 consortium may be used to release oil from nonporous silicate substrates. The consortium may be also used to grow this denitrifying culture in pipelines as a possible method to impede the effects of SRB strains producing corrosion in pipelines or refinery pipes.

TABLE 7

Relative sand release by the steady state POG1 consortium over a period of four weeks (Values 2 or greater represent significant oil release)

| Sample | Day 1 | Day 6 | Day 16 | Day 24 |
|---|---|---|---|---|
| Steady state POG1 Consortium in SL10 medium | 0 | 2 | 4 | 4 |
| SL10 medium alone (control) | 0 | 0 | 0 | 0 |

Example 9

Emulsification of Crude Oil by the $3^{rd}$ Generation Parent Consortium

Microorganisms isolated from the crude oil reservoir sample, refinery environmental samples or environmental samples, containing crude oil or its components, have been shown to form a stable emulsion when grown on crude oil or at least low molecular weight organic acids (LMWOA), e.g., succinate, propionate, lactate, acetate and formate, as a carbon source. The purpose of this Example was to demonstrate the ability of microorganisms, either as isolated species or as a consortium, to form a stable emulsion in the crude oil organic phase.

To test the ability of the $3^{rd}$ gen POG1 consortium to develop an oil-water phase emulsion, a test system was developed using pure strains isolated from sample exposed to crude oil or its organic components. The $3^{rd}$ gen POG1 consortium was anaerobically grown in 32 mL SL10 medium with 1600 ppm $NaNO_3$ and 16 mL autoclaved crude oil (ACO). One sample contained only ACO as the carbon source. The other test samples contained 0.2% of one of the following LMWOAs e.g., succinate, propionate, lactate or acetate. Each emulsion test set contained one vial that had been inoculated with the parent consortium and the second vial that was the control. These were all sealed anaerobically and incubated for two weeks at room temperature. All inoculated samples had completely reduced the nitrate to nitrite after two weeks. An aliquot (2 mL) was removed from each vial and centrifuged at 14,000 rpm for 5 min in a Thermo 5519 microcentrifuge (Thermo Fisher Scientific Inc., Waltham, Mass.). The supernatant was added to a 4 mL Wheaton 225142 sample vial (Wheaton Science Products, Millville, N.J.) containing 1 mL of 2,2,4,4,6,8,8-heptamethyl-nonane (HMN) (Sigma-Aldrich, St Louis, Mo.) and a straight chain liquid organic solvent as the organic phase. The vials were securely fastened in a test tube-rack. The test tube-rack was placed on the lab bench, twelve inches away from the front of a Canon Powershot A530 digital camera, which was set to its macro picture function. A control picture was taken of the 10 vials to record their two liquid-phases in their initial state containing 2 mL of aqueous phase and 1 mL of organic phase. The vials and their contents were shaken by rapidly turning the rack head-over-tail 12 times. They were then placed down on the lab bench, at the same position where the control picture had been taken. A picture was taken immediately to record the initial emulsion state of each vial at time zero. To record the dissipation or stability over time of the emulsion formed by mixing the solutions, a picture was taken at 15 sec intervals until 300 sec had elapsed. The digital frames were studied to measure the dissipation of the emulsion. An emulsion was formed in the organic phase in all vials, including those that had not been inoculated with the consortium. The results are scored on a scale of 1 to 5 and shown in Table 8. The emulsion was scored on a scale of zero to five to indicate the thickness of the emulsion phase at the organic-water interface, where five was the finest and thickest emulsion. The emulsion became more coarse and thinner at the interface as the number decreased to one. A completely dissipated emulsion was scored zero. The non-inoculated controls dissipated either completely or almost completely within the first 15 seconds. An exception was observed with the control sample containing 0.2% acetate which remained somewhat stable for 75 sec before it completely dissipated. Cultures that had only ACO, crude oil plus acetate and ACO plus lactate were stable beyond 5 min and were actually stable for one hour. The inoculated sample containing lactate formed the most stable emulsion in thickness and fineness in comparison with all other samples. Succinate fed cultures did not form a stable emulsion, and propionate fed cultures formed a stable emulsion that was short lived, less than three minutes. These results indicate that several microorganisms within the consortium could emulsify crude oil and that this ability could be enhanced using low molecular weight organic acids supplements such as lactate and acetate.

Example 10

Comparison of Growth of the POG1 Consortium and the Pure Strain *Thauera* AL9:8 on Targeted Oil Under Anaerobic Denitrifying Conditions Growth rates of the POG1 consortium and *Thauera* strain AL9:8 in oil enrichments under anaerobic denitrifying conditions were compared. *Thauera* strain AL9:8 represents the major microbial constituent of the POG1 consortium. Equivalent inocula of about $10^6$ cells of the consortium and the purified strain were used to inoculate 60 mL serum vials containing a 1:2 ratio of minimal salts medium to autoclaved crude oil under anaerobic conditions. SL10 medium (20 mL) (Table 2) with added nitrate (final concentration of 1100 to 1200 ppm) and 10.0 mL of autoclaved crude oil was used. The medium and crude oil had been deoxygenated by sparging with a mixture of nitrogen and carbon dioxide followed by autoclaving. All manipulations of bacteria were done in an anaerobic chamber. Samples were inoculated in triplicates, were incubated at ambient temperatures for several days and monitored for nitrate and nitrite levels for visible turbidity and gross visible changes to the integrity of the oil phase. POG1 inoculated vials consistently reduced nitrate at a faster rate than did pure cultures of *Thauera* strain AL9:8. Table 9 summarizes the results of the average nitrate reduction for the triplicate cultures of POG1 consortium verses pure cultures of *Thauera* strain AL9:8.

TABLE 8

Modification of the autoclaved crude oil by the $3^{rd}$ gen microorganisms in the presence of various low molecular weight organic acids

| Carbon source | Time (Min) | | | | | | | | | | | | | |
|---|---|---|---|---|---|---|---|---|---|---|---|---|---|---|
| | 0 | 15 | 30 | 45 | 60 | 75 | 90 | 105 | 120 | 150 | 180 | 210 | 240 | 300 |
| ACO + Inoculum | 5 | 3 | 2 | 2 | 2 | 2 | 2 | 2 | 2 | 1 | 1 | 1 | 1 | 1 |
| ACO only | 5 | 1 | 1 | 0 | 0 | 0 | 0 | 0 | 0 | 0 | 0 | 0 | 0 | 0 |
| ACO + Acetate + Inoculum | 5 | 5 | 3 | 3 | 3 | 3 | 3 | 3 | 3 | 1 | 1 | 1 | 1 | 1 |
| ACO + Acetate only | 5 | 5 | 3 | 2 | 2 | 2 | 0 | 0 | 0 | 0 | 0 | 0 | 0 | 0 |
| ACO + Propionate + Inoculum | 5 | 5 | 4 | 3 | 3 | 3 | 2 | 2 | 2 | 1 | 0 | 0 | 0 | 0 |
| ACO + Propionate only | 5 | 1 | 1 | 1 | 1 | 1 | 1 | 1 | 1 | 1 | 0 | 0 | 0 | 0 |
| ACO + Lactate + Inoculum | 5 | 4 | 4 | 4 | 4 | 3 | 3 | 3 | 3 | 3 | 3 | 3 | 3 | 3 |
| ACO + Lactate only | 5 | 0 | 0 | 0 | 0 | 0 | 0 | 0 | 0 | 0 | 0 | 0 | 0 | 0 |
| ACO + Succinate + Inoculum | 5 | 0 | 0 | 0 | 0 | 0 | 0 | 0 | 0 | 0 | 0 | 0 | 0 | 0 |
| ACO + Succinate only | 5 | 0 | 0 | 0 | 0 | 0 | 0 | 0 | 0 | 0 | 0 | 0 | 0 | 0 |

(Values 2 or greater represent significant oil release and reflects the stability of the emulsion formed as described (5 > 4 > 3 > 2 > 1))

TABLE 9

Anaerobic growth in oil enrichments

| Microbial inoculum | Average[1] ppm Nitrate Day 0 | Average[1] ppm Nitrate Day 5 | Average[1] % of Nitrate reduced after 6 days |
|---|---|---|---|
| POG1 consortium | 971 | 117 | 95% |
| Strain AL9:8 | 1323 | 789 | 43% |

[1]Nitrate values are the average of three replicates per microbial test inoculum The POG1 consortium consistently developed biofilms under anaerobic denitrifying conditions in oil enrichments, a phenomenon not observed consistently in oil enrichments of *Thauera* strain AL9:8. Table 10 summarizes the results obtained for a set of oil enrichments cultured anaerobically as above in the SL10 medium and autoclaved crude oil (2:1) ratio. These cultures were initially incubated with ~300 ppm nitrate and then further supplemented with nitrate to a final concentration of 1100-1200 ppm for 6 days. Formation of a stable biofilm was observed on the surface of the glass vial [after 3-5 days]. These results underline the synergistic effect of various components of the POG1 consortium, whose major constituent is *Thauera* strain AL 9:8, on forming a biofilm compared to that formed by *Thauera* strain AL9:8 alone.

The results demonstrate that the selected denitrifying consortium may have a more synergistic affect that contributes to a higher growth rate on nitrate than its primary constituent, *Thauera* strain AL9:8. This may imply that the consortium may have a competitive advantage in the presence of SRB under denitrifying conditions. Additionally, this may support its use as denitrifying culture in pipelines as possible method to impede the effects of SRB strains, which produce corrosion in pipelines or refinery pipes.

TABLE 10

Biofilm formation of microbes in oil enrichments

| Microbial Oil Enrichment | Biofilm Formation |
|---|---|
| POG1 consortium | + |
| POG1 consortium | + |
| POG1 consortium | + |
| POG1 consortium | + |
| POG1 consortium | + |
| Strain AL9:8 | − |
| Strain AL9:8 | − |
| Strain AL9:8 | − |
| Strain AL9:8 | − |
| Strain AL9:8 | − |

What is claimed is:

1. A composition for enhancing oil recovery or for in situ bioremediation comprising an isolated consortium of microbial species comprising:
   a) at least one species of the genus *Thauera* having a 16S rDNA nucleic acid molecule that has at least 95% identity to SEQ ID NO: 15;
   b) at least one species having a 16S rDNA nucleic acid molecule that has at least 95% identity to SEQ ID NO: 16; and
   c) at least one species having a 16S rDNA nucleic acid molecule that has at least 95% identity to SEQ ID NO: 17, wherein *Thauera* species comprise at least 60% of the population of the consortium.

2. The composition of claim 1 wherein an *Azoarcus* species is present and comprises at least 1% of the population of the consortium.

3. The composition of claim 1 wherein *Thauera* species comprise at least 90% of the population of the consortium.

4. The composition of claim 1 wherein *Thauera* species comprise at least 80% of the population of the consortium.

5. The composition of claim 4 wherein *Thauera* species comprise at least 70% of the population of the consortium.

6. An isolated consortium of microbial species, comprising:
   a) at least one species of the genus *Thauera* having a 16S rDNA nucleic acid molecule that has at least 95% identity to SEQ ID NO: 15;
   b) at least one species having a 16S rDNA nucleic acid molecule that has at least 95% identity to SEQ ID NO: 16; and
   c) at least one species having a 16S rDNA nucleic acid molecule that has at least 95% identity to SEQ ID NO: 17, wherein *Thauera* species comprise at least 60% of the population of the consortium.

* * * * *